(12) United States Patent
Chen et al.

(10) Patent No.: US 9,890,171 B2
(45) Date of Patent: Feb. 13, 2018

(54) ALDOSTERONE SYNTHASE INHIBITORS

(71) Applicant: Boehringer Ingelheim International GmbH, Ingelheim am Rhein (DE)

(72) Inventors: Zhidong Chen, Ridgefield, CT (US); Derek Cogan, Ridgefield, CT (US); Xin Guo, Danbury, CT (US); Daniel Richard Marshall, Norwalk, CT (US); Kenneth Michael Meyers, Seymour, CT (US); Yunlong Zhang, Valhalla, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 15 days.

(21) Appl. No.: 15/532,126

(22) PCT Filed: Dec. 1, 2015

(86) PCT No.: PCT/US2015/063064
§ 371 (c)(1),
(2) Date: Jun. 1, 2017

(87) PCT Pub. No.: WO2016/089800
PCT Pub. Date: Jun. 9, 2016

(65) Prior Publication Data
US 2017/0267688 A1    Sep. 21, 2017

Related U.S. Application Data

(60) Provisional application No. 62/086,218, filed on Dec. 2, 2014.

(51) Int. Cl.
| | | |
|---|---|---|
| *C07D 519/00* | (2006.01) | |
| *A61K 31/437* | (2006.01) | |
| *A61K 31/4375* | (2006.01) | |
| *A61P 9/00* | (2006.01) | |
| *A61K 31/4709* | (2006.01) | |
| *A61K 31/436* | (2006.01) | |
| *A61K 31/4725* | (2006.01) | |
| *C07D 491/052* | (2006.01) | |
| *A61K 31/553* | (2006.01) | |
| *A61K 31/55* | (2006.01) | |
| *A61K 31/4704* | (2006.01) | |

(52) U.S. Cl.
CPC ....... *C07D 491/052* (2013.01); *C07D 519/00* (2013.01)

(58) Field of Classification Search
CPC .......................... C07D 491/052; C07D 519/00
USPC ....................................................... 514/302
See application file for complete search history.

(56) References Cited

U.S. PATENT DOCUMENTS

| | | | | |
|---|---|---|---|---|
| 9,181,272 B2* | 11/2015 | Balestra | ............... | C07D 498/04 |
| 9,334,285 B2* | 5/2016 | Burke | ................ | C07D 491/052 |
| 9,745,289 B2* | 8/2017 | Hornberger | .......... | C07D 405/14 |
| 2012/0316195 A1* | 12/2012 | Allan | .................. | C07D 213/30 514/302 |
| 2013/0143863 A1* | 6/2013 | Aebi | ..................... | C07D 401/04 514/210.18 |
| 2016/0229807 A1* | 8/2016 | Aebi | .................... | C07D 217/18 |

FOREIGN PATENT DOCUMENTS

| | | |
|---|---|---|
| WO | 2013041591 | 3/2013 |
| WO | 2013156423 | 10/2013 |
| WO | 2014179186 A1 | 11/2014 |

OTHER PUBLICATIONS

Martin; Org. Biomol. Chem., 2016, 14, 5992. (Year: 2016).*
Martin; J. Med. Chem. 2015, 58, 8054-8065. (Year: 2015).*
Azizi; Nephrol Dial Transplant 2013, 28, 36-43. (Year: 2013).*
Hu; J. Med. Chem. 2014, 57, 5011-5022. (Year: 2014).*
Banki; PLoS One 2012, 7, e39938. (Year: 2012).*
Andersen; Curr Hypertens Rep,2013, 15, 484-488. (Year: 2013).*
Hargovan; Journal of the Royal Society of Medicine Cardiovascular Disease 2014, 0, 1-9. (Year: 2014).*
Dorrance; F1000 Prime Reports 2014, 6-61. (Year: 2014).*
International Search Report and Written Opinion, Form ISA220, dated Feb. 22, 2016, for PCT/US2015063064.

* cited by examiner

*Primary Examiner* — Daniel R Carcanague
(74) *Attorney, Agent, or Firm* — Marc Began; David L. Kershner

(57) ABSTRACT

The present invention relates to compounds of the formulas (IA) and (IB) and pharmaceutically acceptable salts thereof, wherein A and $R^1$-$R^6$, are as defined herein. The invention also relates to pharmaceutical compositions comprising these compounds, methods of using these compounds in the treatment of various diseases and disorders, processes for preparing these compounds and intermediates useful in these processes.

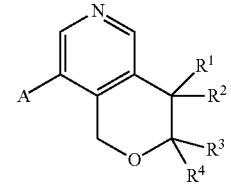

(IA)

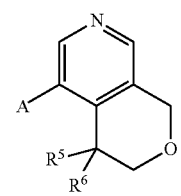

(IB)

11 Claims, No Drawings

ALDOSTERONE SYNTHASE INHIBITORS

FIELD OF THE INVENTION

This invention relates to heteroaryl compounds that are useful as inhibitors of aldosterone synthase (CYP11B2) and are thus useful for treating a variety of diseases that are mediated or sustained by aldosterone activity, including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

BACKGROUND

Aldosterone is a steroid hormone having mineralcorticoid activity. It is produced primarily by the adrenal glomerulosa in response to angiotensin II, adrenocorticotropic hormone and increased serum potassium levels. A primary physiological role of aldosterone in the kidney is to maintain sodium and potassium balance by regulating cation exchange ($Na^+$ reabsorption and $K^+$ secretion) in the distal nephron. However, aldosterone has also been shown to be a pro-inflammatory and profibrotic hormone in blood vessels, heart and kidneys. The effects of aldosterone on gene expression are mediated via binding to the mineralocorticoid receptor (MR) and a canonical nuclear hormone receptor pathway. However, the hormone also elicits rapid, non-genomic responses, including acute regulation of the activity of tubular ion transporters, for example $Na^+/H^+$ exchangers (NHEs), $H^+$-ATPase, ENaC, and $Na^+/K^+$ ATPase (D. W. Good, 2007, Hypertension, 49, 728-739). It is likely that some of these effects are mediated by MR-independent pathways. Conversely, the MR can bind alternative ligands, including deoxycorticosterone, corticosterone, cortisol and progesterone. Thus, inhibition of aldosterone synthesis is predicted to have a pharmacodynamic profile distinct from what is observed with MR antagonists.

Aldosterone is synthesized in the zona glomerulosa of the adrenal glands, where a single enzyme, CYP11B2 (aldosterone synthase), catalyzes the 3-step conversion of 11-deoxycorticosterone (11-DOC) to aldosterone, via corticosterone and 18-hydroxycorticosterone. Adrenal aldosterone synthase activity is regulated by Angiotensin II and K+ levels and unidentified adipocyte-derived mediators. Low levels of aldosterone synthase have also been detected in the heart and CNS, though the physiological relevance is uncertain, perhaps relating to paracrine effects. Systemic aldosterone is believed to derive essentially entirely from the adrenals.

Beyond its role in regulating sodium and potassium balance, aldosterone has been shown to have pro-inflammatory and pro-fibrotic actions in multiple tissues including the kidney, blood vessels and the heart. The harmful effects of inappropriate aldosterone levels on blood pressure and cardiac, renal, cerebral and vascular function and structure, have been widely reported in the literature, including: i) increase in sodium retention through $Na^+/K^+$ ATPase pump induction in distal tubules resulting in volume expansion and high blood pressure, ii) endothelial dysfunction, iii) oxidative stress, iv) renal and cardiac hypertrophy, v) fibroblast proliferation, and, vi) excessive synthesis of extracellular matrix resulting in renal, cardiac and vascular fibrosis.

Benefits of aldosterone blockade/inhibition include reduction of kidney fibrosis and improvement of glomerular filtration rate and albuminuria in models of chronic kidney disease (CKD) and diabetic nephropathy. This is supported by pre-clinical data (for example, Fiebler et al., 2005, Circulation, 111, 3087-3094; Lea et al., 2009, Kidney International, 75, 936-945). Other benefits reported in the literature include decreased blood pressure and end-organ damage (heart, kidney, vessels) in both renin-dependent and salt-sensitive hypertension.

Although many of aldosterone's known effects are mediated through mineralcorticoid receptor (MR) activation, and much of the evidence favoring targeting this pathway comes from experiments with MR antagonists, non-MR mediated effects are reported and knockout mice for MR and aldosterone synthase exhibit different phenotypes (Makhanova et al. 2006, Berger et al. 1998, Funder 2007). These observations further suggest that aldosterone synthase inhibitors may have a different profile and offer advantages compared to MR antagonists.

For example, several aldosterone actions are not inhibited by MR antagonists, including the potentially deleterious effects on the vasculature (increased peripheral vascular resistance), the heart (effects on myocardial re-polarization) and the endocrine system (decreased insulin secretion). Furthermore, MR antagonism leads to an increase in circulating aldosterone, predicted to increase aldosterone signaling via non-MR pathways and, potentially, partially overcoming the MR blockade itself.

Current therapeutic strategies focus on slowing progression and treating conditions underlying diabetic nephropathy: control of blood glucose and control of high blood pressure. Angiotensin converting enzyme (ACE) inhibitors and angiotensin receptor blockers (ARB) have shown renal benefit in diabetic patients. To date, representatives of the ACE inhibitor class and from the ARB class have been approved for the treatment of diabetic nephropathy. These therapies represent limited benefit for the diabetic nephropathy patients.

Although the use of ACE inhibitors and ARBs represents the current standard of care for patients with diabetic nephropathy, patients progressively lose kidney function while on these medications, as seen in the IDNT (E. J. Lewis et al., 2001, N. Engl. J. Med., 345, 851-860) and RENAAL (B. M. Brenner et al., 2001, N. Engl. J. Med., 345, 861-869) studies, which reported a decrease over time in estimated glomerular filtration rate, which is an accurate measure of chronic kidney disease progression in patients treated by these conventional methods. At stage 5 chronic kidney disease, renal replacement therapy is required, in the form of either dialysis or transplant.

Aldosterone synthase inhibition may also be predicted to offer advantages as add-on therapy with ACE inhibitors and ARBs. Notably, 25-50% of patients receiving these agents experience "aldosterone breakthrough" in which aldosterone levels initially lowered by these treatments eventually return to pretreatment levels. This phenomenon would not occur with direct aldosterone synthase inhibition and could enhance efficacy in combination therapy.

There remains a high unmet medical need to treat diabetic nephropathy, to halt or regress disease progression by specifically targeting the underlying pathophysiological mechanisms associated with chronic inflammation and fibrosis, irrespective of the original cause of the disease and when co-administered with current therapies. The studies described above and in the literature provide evidence that inhibitors of aldosterone synthesis will be useful for the treatment of diabetic kidney disease including diabetic nephropathy; non-diabetic kidney disease including glomerulosclerosis, glomerulonephritis, IGA nephropathy, nephritic syndrome and focal segmental glomerulosclerosis (FSGS); cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism; adrenal hyperplasia and primary and secondary hyperaldosteronism.

BRIEF SUMMARY OF THE INVENTION

The present invention provides novel compounds that inhibit aldosterone synthase and thus useful for treating a variety of diseases and disorders that can be alleviated by lowering levels of aldosterone including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In an embodiment of the invention, there are provided compounds of the formulas IA or IB

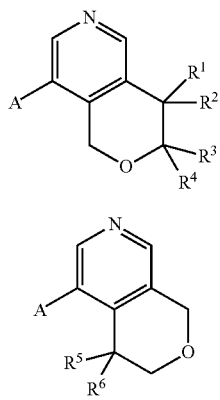

wherein:
A is selected from the group consisting of
benzoimidazolyl, benzo[d]isoxazolyl, benzooxazolyl, benzothiazolyl, benzotriazolyl, chromanyl, chromenyl, cyclohexen-1-yl, 2,3-dihydro-benzo[1,4]dioxinyl, 2,3-dihydro-5H-benzo[e][1,4]dioxepinyl, 3,4-dihydro-2H-benzo[b][1,4]dioxepinyl, 3,4-dihydro-2H-benzo[f][1,4]oxazepin-5-onyl, 2,3-dihydro-benzofuranyl, 4,5-dihydro-1H-indazolyl, 1,3-dihydroindol-2-onyl, 1,3-dihydro-isoindolyl, 3,4-dihydro-2H-isoquinolin-1-onyl, 3,4-dihydro-2H-naphthalen-1-onyl, 3,4-dihydro-2H-[1,8]napthyridinyl, 7,8-dihydro-5H-pyrano[4,3-b]pyridinyl, 6,7-dihydro-[1]pyrindin-5-onyl, 3,4-dihydro-1H-quinolin-2-onyl, imidazo[1,2-a]pyridinyl, imidazo[1,5-a]pyridinyl, indanyl, indazolyl, indolyl, isochromanyl, isoquinolinyl, phenyl, pyrazolyl, pyrrolo[2,3-b]pyridinyl, quinolinyl, 1,3,4,5-tetrahydro-benzo[c]oxepinyl, 4, 5, 6, 7-tetrahydroindazolyl, thiazolyl and [1,2,4]triazolo[4,3-a]pyridinyl;

wherein A is optionally substituted with one to three groups selected from $C_{1-6}$alkyl, $C_{3-5}$cycloalkyl, —OH, oxo, $C_{1-6}$alkoxy, halogen, —$CF_3$, —CN, —C(O)$C_{1-3}$alkyl and —C(O)$NH_2$;
$R^1$ is selected from H and —$C_{1-3}$alkyl;
$R^2$ is selected from —OH, —CN, —$NH_2$, —N($C_{1-3}$alkyl)$_2$, —NHC(O)$C_{1-3}$alkyl, —NHC(O) $C_{3-5}$ cycloalkyl, —$NHSO_2C_{1-3}$alkyl and —NHC(O)$CH_2C$ $(CH_3)_2$ —OH;
$R^3$ is H;
$R^4$ is H; or
$R^3$ and $R^4$ together form a Spiro cyclopropyl group;
$R^5$ is H or —$C_{1-3}$alkyl; and
$R^6$ is —OH;
or a salt thereof.

In another embodiment there are provided compounds of the formula IA according to the embodiment above, wherein A, $R^1$, $R^2R^3$ and $R^4$ are as defined in the embodiment above; or a salt thereof.

In another embodiment there are provided compounds of the formula IB according to the first embodiment, wherein
A is selected from the group consisting of
benzo[d]isoxazol-5-yl, benzotriazol-5-yl, chromen-6- or -7-yl, cyclohexen-1-yl, 4,5-dihydro-1H-indazol-6-yl, 3,4-dihydro-2H-[1,8]napthyridin-6-yl, imidazo[1,5-a]pyridine-6-yl, indan-5-yl, indazol-5- or -6-yl, isochroman-7-yl, 2,3-dihydro-benzo[1,4]dioxin-6-yl, 3,4-dihydro-2H-benzo[b][1,4]dioxepin-7-yl, 2,3-dihydro-5H-benzo[e][1,4]dioxepin-7-yl, 3,4-dihydro-2H-naphthalen-1-on-6- or -7-yl, chroman-6- or -7-yl, 1,3,4,5-tetrahydro-benzo[c]oxepin-8-yl and 4, 5, 6, 7-tetrahydroindazol-6-yl;
$R^5$ is H or —$CH_3$; and
$R^6$ is OH;
or a salt thereof.

In another embodiment there are provided compounds of the formula IA according to the first or second embodiment, wherein
A is selected from the group consisting of
benzoimidazol-5-yl, benzo[d]isoxazol-5-yl, benzooxazol-5-yl, benzothiazol-5-yl, benzotriazol-5-yl, chroman-6- or -7-yl, chromen-6- or -7-yl, cyclohexen-1-yl, 2,3-dihydro-benzo[1,4]dioxin-6-yl, 2,3-dihydro-5H-benzo[e][1,4]dioxepin-7-yl, 3,4-dihydro-2H-benzo[b][1,4]dioxepin-7-yl, 4,5-dihydro-1H-indazol-6-yl, 1,3-dihydroindol-2-on-5-yl, 3,4-dihydro-2H-isoquinolin-1-on-6-yl, 3,4-dihydro-2H-naphthalen-1-on-6- or -7-yl, 3,4-dihydro-2H-[1,8] napthyridin-6-yl, 3,4-dihydro-1H-quinolin-2-on-6-yl, imidazo[1,2-a]pyridine-7-yl, imidazo[1,5-a]pyridine-6-yl, indan-5-yl, indazol-5- or -6-yl, isochroman-7-yl, isoquinolin-6-yl, phenyl, quinolin-3- or -6-yl and 4, 5, 6, 7-tetrahydroindazol-6-yl, indol-5 or 6-yl, 1,3,4,5-tetrahydro-benzo[c]oxepin-8-yl;
wherein A is optionally substituted with one to three groups selected from $C_{1-3}$alkyl, $C_{3-5}$cycloalkyl, —OH, oxo, $C_{1-3}$alkoxy, Cl, F, —$CF_3$, —CN, —C(O)$CH_3$ and —C(O)$NH_2$;
$R^1$ is selected from H and —$CH_3$;
$R^2$ is selected from —OH, —CN, —$NH_2$, —N($CH_3$)$_2$, —NHC(O)$C_{1-3}$alkyl, —NHC(O)cyclopropyl, —$NHSO_2C_{1-3}$ alkyl and —NHC(O)$CH_2C(CH_3)_2$—OH;
or a salt thereof.

In another embodiment there are provided compounds of the formula IA according to the first, second or fourth embodiment, wherein
A is selected from the group consisting of
benzo[d]isoxazol-5-yl, benzotriazol-5-yl, chromen-6- or -7-yl, cyclohexen-1-yl, 4,5-dihydro-1H-indazol-6-yl, 3,4- dihydro-2H-[1,8]napthyridin-6-yl, imidazo[1,5-a]pyridine-6-yl, indan-5-yl, indazol-5- or -6-yl, isochroman-7-yl, 2,3-dihydro-benzo[1,4]dioxin-6-yl, 3,4-dihydro-2H-benzo[b][1,4]dioxepin-7-yl, 2,3-dihydro-5H-benzo[e][1,4]dioxepin-7-yl, 3,4-dihydro-2H-naphthalen-1-on-6- or -7-yl, chroman-6- or -7-yl, 1,3,4,5-tetrahydro-benzo[c]oxepin-8-yl and 4, 5, 6, 7-tetrahydroindazol-6-yl;

wherein A is optionally substituted with one to three groups selected from $C_{1-3}$alkyl, $C_{3-5}$cycloalkyl, —OH, oxo, $C_{1-3}$alkoxy, Cl, F, —CF$_3$, —CN, —C(O)CH$_3$ and —C(O)NH$_2$; and $R^2$ is selected from —OH, —CN, —NHC(O)$C_{1-3}$alkyl, —NHC(O)cyclopropyl, —NHSO$_2$C$_{1-3}$alkyl and —NHC(O)CH$_2$C(CH$_3$)$_2$—OH;

or a salt thereof.

In another aspect of the invention, there is provided a compound of the general formula I or a pharmaceutically acceptable salt thereof for use in a therapeutic method as described hereinbefore and hereinafter.

Table 1 shows representative compounds of the invention which can be made by the methods described in the general synthetic schemes, the examples, and known methods in the art.

TABLE 1

| Cpd No | STRUCTURE | Name |
|---|---|---|
| 1 | 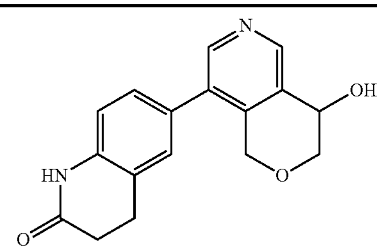 | 6-(4-Hydroxy-3,4-dihydro-1H-pyrano[4,3-c]pyridin-8-yl)-3,4-dihydro-1H-quinolin-2-one, Enantiomer II |
| 2 | 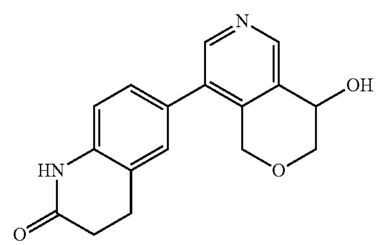 [SMILES: O=C1CCc2cc(-c3cncc4c3COCC4O)ccc2N1] | 6-(4-Hydroxy-3,4-dihydro-1H-pyrano[4,3-c]pyridin-8-yl)-3,4-dihydro-1H-quinolin-2-one, Enantiomer I |
| 3 | 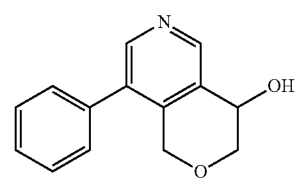 [SMILES: OC1COCc2c(-c3ccccc3)cncc21] | 8-Phenyl-3,4-dihydro-1H-pyrano[4,3-c]pyridin-4-ol, Enantiomer I |
| 4 | 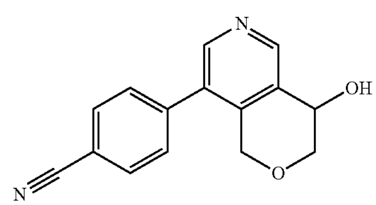 [SMILES: N#Cc1ccc(-c2cncc3c2COCC3O)cc1] | 4-(4-Hydroxy-3,4-dihydro-1H-pyrano[4,3-c]pyridin-8-yl)-benzonitrile, Enantiomer I |
| 5 | 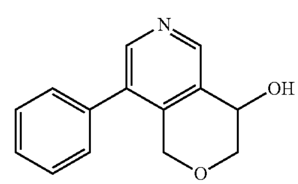 [SMILES: OC1COCc2c(-c3ccccc3)cncc21] | 8-Phenyl-3,4-dihydro-1H-pyrano[4,3-c]pyridin-4-ol, Enantiomer II |
| 6 | 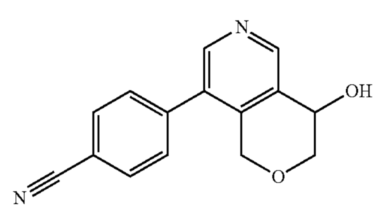 [SMILES: N#Cc1ccc(-c2cncc3c2COCC3O)cc1] | 4-(4-Hydroxy-3,4-dihydro-1H-pyrano[4,3-c]pyridin-8-yl)-benzonitrile, Enantiomer II |

TABLE 1-continued

| Cpd No | STRUCTURE | Name |
|---|---|---|
| 7 | 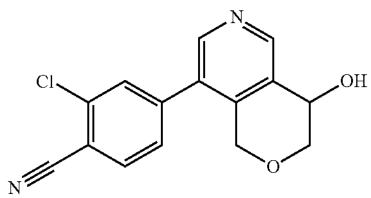 [SMILES: N#Cc1ccc(-c2cncc3c2COCC3O)cc1Cl] | 2-Chloro-4-(4-hydroxy-3,4-dihydro-1H-pyrano[4,3-c]pyridin-8-yl)-benzonitrile, Enantiomer I |
| 8 | 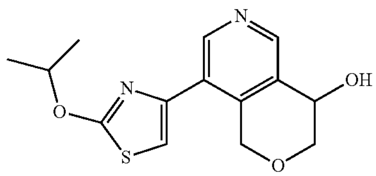 [SMILES: CC(C)Oc1nc(-c2cncc3c2COCC3O)cs1] | 8-(2-Isopropoxy-thiazol-4-yl)-3,4-dihydro-1H-pyrano[4,3-c]pyridin-4-ol, Enantiomer I |
| 9 | 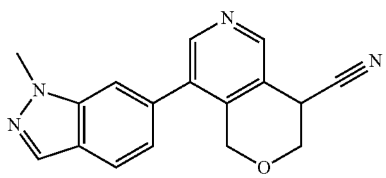 [SMILES: Cn1ncc2ccc(-c3cncc4c3COCC4C#N)cc21] | 8-(1-Methyl-1H-indazol-6-yl)-3,4-dihydro-1H-pyrano[4,3-c]pyridine-4-carbonitrile |
| 10 | 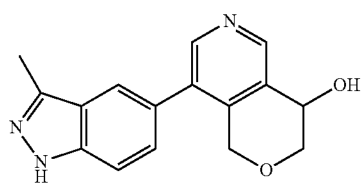 [SMILES: Cc1n[nH]c2ccc(-c3cncc4c3COCC4O)cc12] | 8-(3-Methyl-1H-indazol-5-yl)-3,4-dihydro-1H-pyrano[4,3-c]pyridin-4-ol, Enantiomer I |
| 11 | 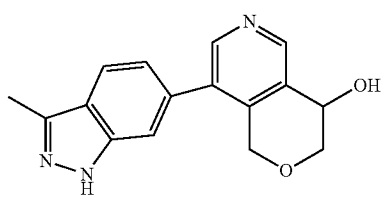 [SMILES: Cc1n[nH]c2cc(-c3cncc4c3COCC4O)ccc12] | 8-(3-Methyl-1H-indazol-6-yl)-3,4-dihydro-1H-pyrano[4,3-c]pyridin-4-ol, Enantiomer I |
| 12 | 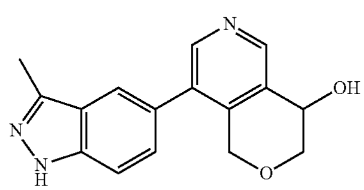 [SMILES: Cc1n[nH]c2ccc(-c3cncc4c3COCC4O)cc12] | 8-(3-Methyl-1H-indazol-5-yl)-3,4-dihydro-1H-pyrano[4,3-c]pyridin-4-ol, Enantiomer II |
| 13 | 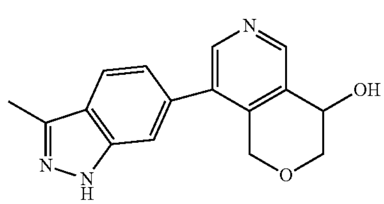 [SMILES: Cc1n[nH]c2cc(-c3cncc4c3COCC4O)ccc12] | 8-(3-Methyl-1H-indazol-6-yl)-3,4-dihydro-1H-pyrano[4,3-c]pyridin-4-ol, Enantiomer II |
| 14 | 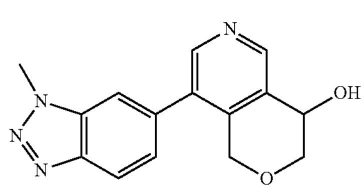 [SMILES: Cn1nnc2ccc(-c3cncc4c3COCC4O)cc21] | 8-(3-Methyl-3H-benzotriazol-5-yl)-3,4-dihydro-1H-pyrano[4,3-c]pyridin-4-ol, Enantiomer II |

TABLE 1-continued

| Cpd No | STRUCTURE | Name |
|---|---|---|
| 15 | 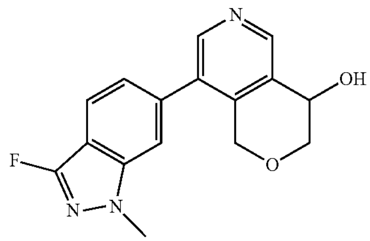 [SMILES: Cn1nc(F)c2ccc(-c3cncc4c3COCC4O)cc21] | 8-(3-Fluoro-1-methyl-1H-indazol-6-yl)-3,4-dihydro-1H-pyrano[4,3-c]pyridin-4-ol, Enantiomer II |
| 16 | 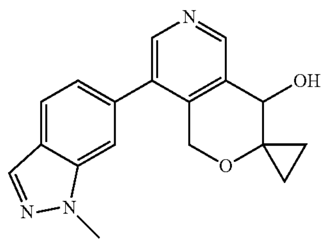 [SMILES: Cn1ncc2ccc(-c3cncc4c3COC3(CC3)C4O)cc21] | 8-(1-methylindazol-6-yl)spiro[1,4-dihydropyrano[4,3-c]pyridine-3,1'-cyclopropane]-4-ol, Enantiomer I |
| 17 | 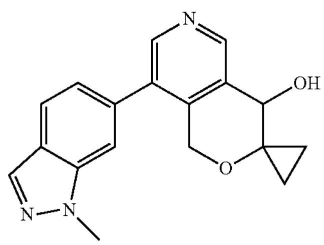 [SMILES: Cn1ncc2ccc(-c3cncc4c3COC3(CC3)C4O)cc21] | 8-(1-methylindazol-6-yl)spiro[1,4-dihydropyrano[4,3-c]pyridine-3,1'-cyclopropane]-4-ol, Enantiomer II |
| 18 | 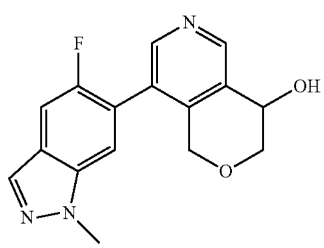 [SMILES: Cn1ncc2cc(F)c(-c3cncc4c3COCC4O)cc21] | 8-(5-Fluoro-1-methyl-1H-indazol-6-yl)-3,4-dihydro-1H-pyrano[4,3-c]pyridin-4-ol, Enantiomer II |
| 19 | 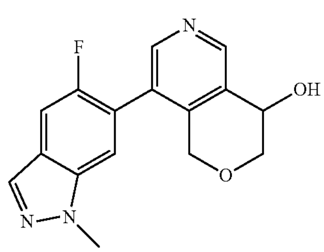 [SMILES: Cn1ncc2cc(F)c(-c3cncc4c3COCC4O)cc21] | 8-(5-Fluoro-1-methyl-1H-indazol-6-yl)-3,4-dihydro-1H-pyrano[4,3-c]pyridin-4-ol, Enantiomer I |
| 20 | 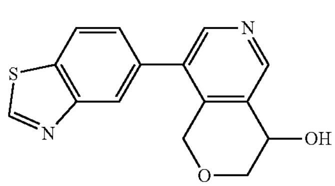 [SMILES: OC1COCc2c(-c3ccc4scnc4c3)cncc21] | 8-Benzothiazol-5-yl-3,4-dihydro-1H-pyrano[4,3-c]pyridin-4-ol, Enantiomer I |

TABLE 1-continued

| Cpd No | STRUCTURE | Name |
|---|---|---|
| 21 | 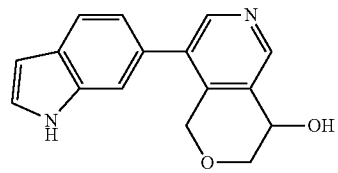 [SMILES: OC1COCc2c(-c3ccc4cc[nH]c4c3)cncc21] | 8-(1H-Indol-6-yl)-3,4-dihydro-1H-pyrano[4,3-c]pyridin-4-ol, Enantiomer I |
| 22 | 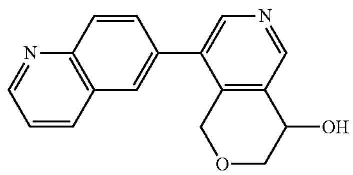 [SMILES: OC1COCc2c(-c3ccc4ncccc4c3)cncc21] | 8-Quinolin-6-yl-3,4-dihydro-1H-pyrano[4,3-c]pyridin-4-ol, Enantiomer I |
| 23 | 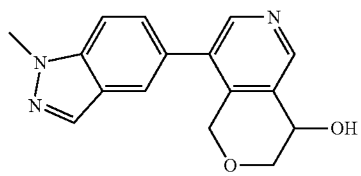 [SMILES: Cn1ncc2cc(-c3cncc4c3COCC4O)ccc21] | 8-(1-Methyl-1H-indazol-5-yl)-3,4-dihydro-1H-pyrano[4,3-c]pyridin-4-ol, Enantiomer I |
| 24 | 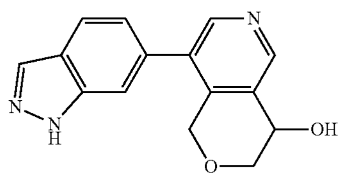 [SMILES: OC1COCc2c(-c3ccc4cn[nH]c4c3)cncc21] | 8-(1H-Indazol-6-yl)-3,4-dihydro-1H-pyrano[4,3-c]pyridin-4-ol, Enantiomer I |
| 25 | 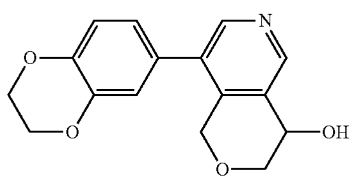 [SMILES: OC1COCc2c(-c3ccc4c(c3)OCCO4)cncc21] | 8-(2,3-Dihydro-benzo[1,4]dioxin-6-yl)-3,4-dihydro-1H-pyrano[4,3-c]pyridin-4-ol, Enantiomer I |
| 26 | 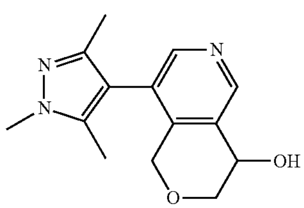 [SMILES: Cc1nn(C)c(C)c1-c1cncc2c1COCC2O] | 8-(1,3,5-Trimethyl-1H-pyrazol-4-yl)-3,4-dihydro-1H-pyrano[4,3-c]pyridin-4-ol, Enantiomer I |
| 27 | 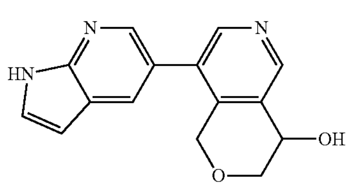 [SMILES: OC1COCc2c(-c3cnc4[nH]ccc4c3)cncc21] | 8-(1H-Pyrrolo[2,3-b]pyridin-5-yl)-3,4-dihydro-1H-pyrano[4,3-c]pyridin-4-ol, Enantiomer I |
| 28 | 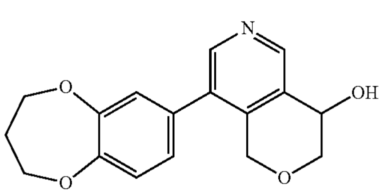 [SMILES: OC1COCc2c(-c3ccc4c(c3)OCCCO4)cncc21] | 8-(3,4-Dihydro-2H-benzo[b][1,4]dioxepin-7-yl)-3,4-dihydro-1H-pyrano[4,3-c]pyridin-4-ol, Enantiomer I |

TABLE 1-continued

| Cpd No | STRUCTURE | Name |
|---|---|---|
| 29 | 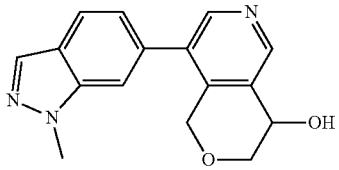 | 8-(1-Methyl-1H-indazol-6-yl)-3,4-dihydro-1H-pyrano[4,3-c]pyridin-4-ol, Enantiomer I |
| 30 | 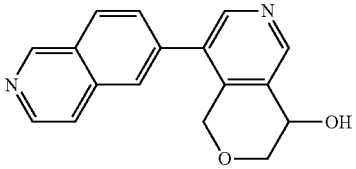 [SMILES: OC1COCc2c(-c3ccc4cnccc4c3)cncc21] | 8-Isoquinolin-6-yl-3,4-dihydro-1H-pyrano[4,3-c]pyridin-4-ol, Enantiomer I |
| 31 | 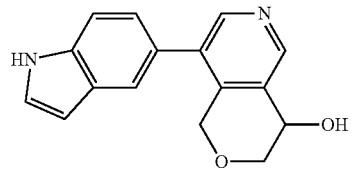 | 8-(1H-Indol-5-yl)-3,4-dihydro-1H-pyrano[4,3-c]pyridin-4-ol, Enantiomer I |
| 32 | 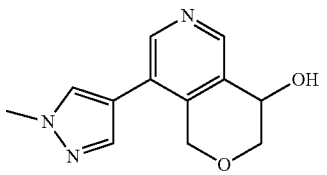 [SMILES: Cn1cc(-c2cncc3c2COCC3O)cn1] | 8-(1-Methyl-1H-pyrazol-4-yl)-3,4-dihydro-1H-pyrano[4,3-c]pyridin-4-ol, Enantiomer II |
| 33 | 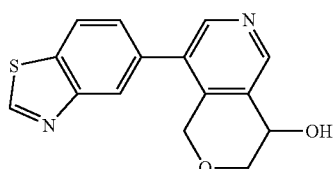 | 8-Benzothiazol-5-yl-3,4-dihydro-1H-pyrano[4,3-c]pyridin-4-ol, Enantiomer II |
| 34 | 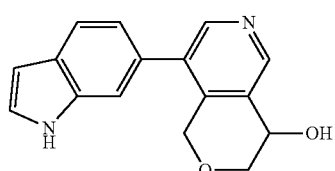 | 8-(1H-Indol-6-yl)-3,4-dihydro-1H-pyrano[4,3-c]pyridin-4-ol, Enantiomer II |
| 35 | 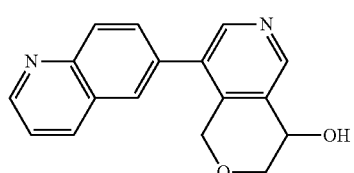 | 8-Quinolin-6-yl-3,4-dihydro-1H-pyrano[4,3-c]pyridin-4-ol, Enantiomer II |
| 36 | 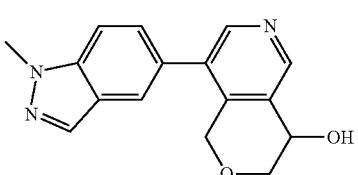 | 8-(1-Methyl-1H-indazol-5-yl)-3,4-dihydro-1H-pyrano[4,3-c]pyridin-4-ol, Enantiomer II |

TABLE 1-continued

| Cpd No | STRUCTURE | Name |
|---|---|---|
| 37 | 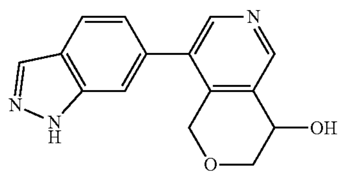 [SMILES: OC1COCc2c(-c3ccc4cn[nH]c4c3)cncc21] | 8-(1H-Indazol-6-yl)-3,4-dihydro-1H-pyrano[4,3-c]pyridin-4-ol, Enantiomer II |
| 38 | 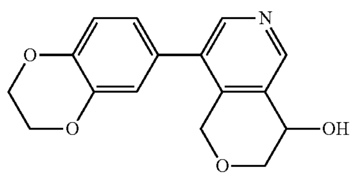 [SMILES: OC1COCc2c(-c3ccc4c(c3)OCCO4)cncc21] | 8-(2,3-Dihydro-benzo[1,4]dioxin-6-yl)-3,4-dihydro-1H-pyrano[4,3-c]pyridin-4-ol, Enantiomer II |
| 39 | 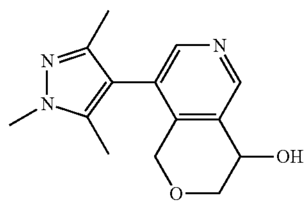 [SMILES: Cc1nn(C)c(C)c1-c1cncc2c1COCC2O] | 8-(1,3,5-Trimethyl-1H-pyrazol-4-yl)-3,4-dihydro-1H-pyrano[4,3-c]pyridin-4-ol, Enantiomer II |
| 40 | 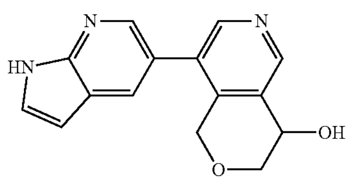 [SMILES: OC1COCc2c(-c3cnc4[nH]ccc4c3)cncc21] | 8-(1H-Pyrrolo[2,3-b]pyridin-5-yl)-3,4-dihydro-1H-pyrano[4,3-c]pyridin-4-ol, Enantiomer II |
| 41 | 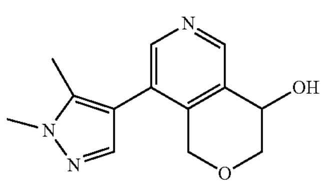 [SMILES: Cc1c(-c2cncc3c2COCC3O)cnn1C] | 8-(1,5-Dimethyl-1H-pyrazol-4-yl)-3,4-dihydro-1H-pyrano[4,3-c]pyridin-4-ol, Enantiomer II |
| 42 | 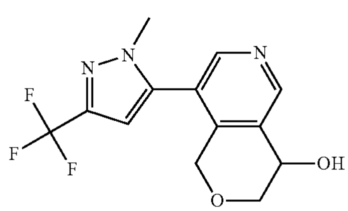 [SMILES: Cn1nc(C(F)(F)F)cc1-c1cncc2c1COCC2O] | 8-(2-Methyl-5-trifluoromethyl-2H-pyrazol-3-yl)-3,4-dihydro-1H-pyrano[4,3-c]pyridin-4-ol, Enantiomer II |
| 43 | 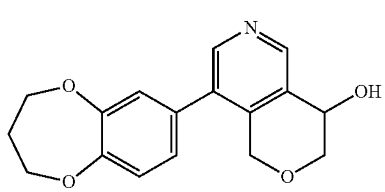 [SMILES: OC1COCc2c(-c3ccc4c(c3)OCCCO4)cncc21] | 8-(3,4-Dihydro-2H-benzo[b][1,4]dioxepin-7-yl)-3,4-dihydro-1H-pyrano[4,3-c]pyridin-4-ol, Enantiomer II |
| 44 | 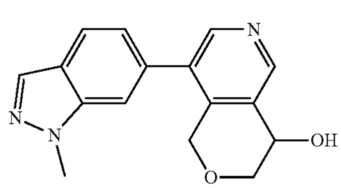 [SMILES: Cn1ncc2ccc(-c3cncc4c3COCC4O)cc21] | 8-(1-Methyl-1H-indazol-6-yl)-3,4-dihydro-1H-pyrano[4,3-c]pyridin-4-ol, Enantiomer II |

TABLE 1-continued

| Cpd No | STRUCTURE | Name |
|---|---|---|
| 45 | 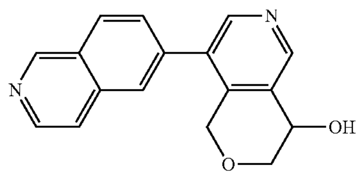 [SMILES: OC1COCc2c(-c3ccc4cnccc4c3)cncc21] | 8-Isoquinolin-6-yl-3,4-dihydro-1H-pyrano[4,3-c]pyridin-4-ol, Enantiomer II |
| 46 | 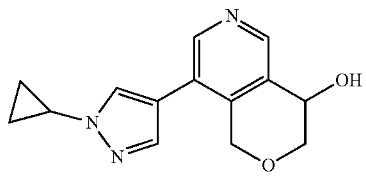 [SMILES: OC1COCc2c(-c3cnn(C4CC4)c3)cncc21] | 8-(1-Cyclopropyl-1H-pyrazol-4-yl)-3,4-dihydro-1H-pyrano[4,3-c]pyridin-4-ol, Enantiomer II |
| 47 | 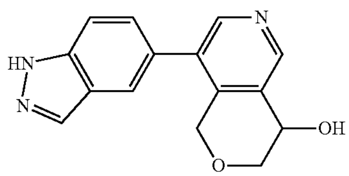 [SMILES: OC1COCc2c(-c3ccc4[nH]ncc4c3)cncc21] | 8-(1H-Indazol-5-yl)-3,4-dihydro-1H-pyrano[4,3-c]pyridin-4-ol, Enantiomer II |
| 48 | 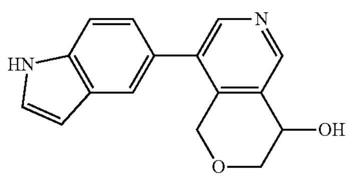 [SMILES: OC1COCc2c(-c3ccc4[nH]ccc4c3)cncc21] | 8-(1H-Indol-5-yl)-3,4-dihydro-1H-pyrano[4,3-c]pyridin-4-ol, Enantiomer II |
| 49 | 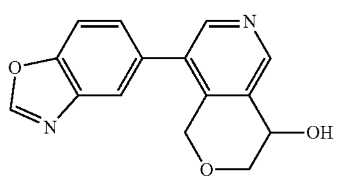 [SMILES: OC1COCc2c(-c3ccc4ocnc4c3)cncc21] | 8-Benzooxazol-5-yl-3,4-dihydro-1H-pyrano[4,3-c]pyridin-4-ol, Enantiomer II |
| 50 | 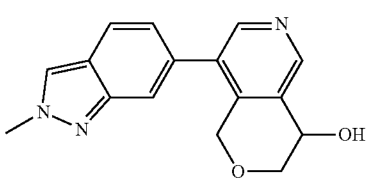 [SMILES: Cn1cc2ccc(-c3cncc4c3COCC4O)cc2n1] | 8-(2-Methyl-2H-indazol-6-yl)-3,4-dihydro-1H-pyrano[4,3-c]pyridin-4-ol, Enantiomer II |
| 51 | 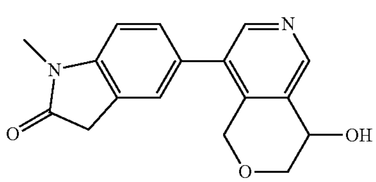 | 5-(4-Hydroxy-3,4-dihydro-1H-pyrano[4,3-c]pyridin-8-yl)-1-methyl-1,3-dihydro-indol-2-one, Enantiomer II |
| 52 | 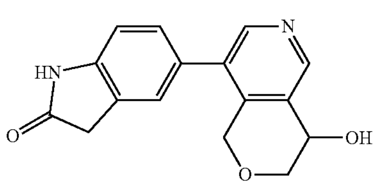 [SMILES: O=C1Cc2cc(-c3cncc4c3COCC4O)ccc2N1] | 5-(4-Hydroxy-3,4-dihydro-1H-pyrano[4,3-c]pyridin-8-yl)-1,3-dihydro-indol-2-one, Enantiomer II |

TABLE 1-continued

| Cpd No | STRUCTURE | Name |
|---|---|---|
| 53 | 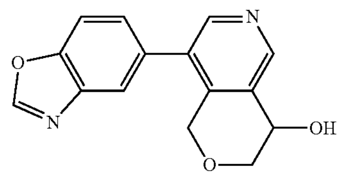 | 8-Benzooxazol-5-yl-3,4-dihydro-1H-pyrano[4,3-c]pyridin-4-ol, Enantiomer I |
| 54 | 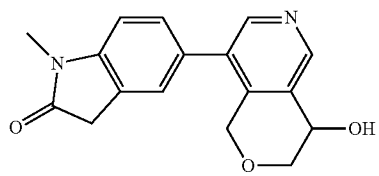 | 5-(4-Hydroxy-3,4-dihydro-1H-pyrano[4,3-c]pyridin-8-yl)-1-methyl-1,3-dihydro-indol-2-one, Enantiomer I |
| 55 | 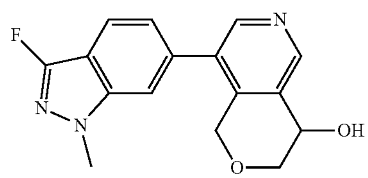 | 8-(3-Fluoro-1-methyl-1H-indazol-6-yl)-3,4-dihydro-1H-pyrano[4,3-c]pyridin-4-ol, Enantiomer I |
| 56 | 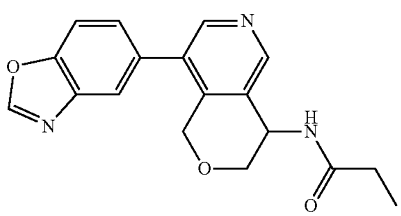 [SMILES: CCC(=O)NC1COCc2c(-c3ccc4ocnc4c3)cncc21] | N-(8-Benzooxazol-5-yl-3,4-dihydro-1H-pyrano[4,3-c]pyridin-4-yl)-propionamide, Enantiomer II |
| 57 | 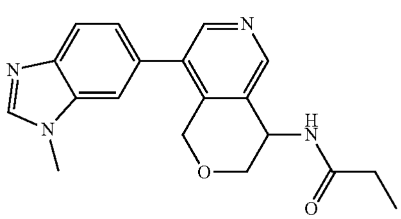 [SMILES: CCC(=O)NC1COCc2c(-c3ccc4ncn(C)c4c3)cncc21] | N-[8-(3-Methyl-3H-benzoimidazol-5-yl)-3,4-dihydro-1H-pyrano[4,3-c]pyridin-4-yl]-propionamide, Enantiomer II |
| 58 | 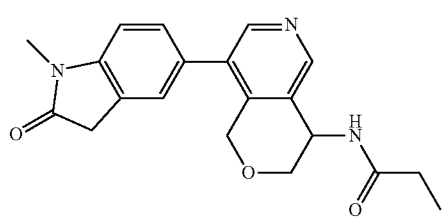 [SMILES: CCC(=O)NC1COCc2c(-c3ccc4c(c3)CC(=O)N4C)cncc21] | N-[8-(1-Methyl-2-oxo-2,3-dihydro-1H-indol-5-yl)-3,4-dihydro-1H-pyrano[4,3-c]pyridin-4-yl]-propionamide, Enantiomer II |
| 59 | 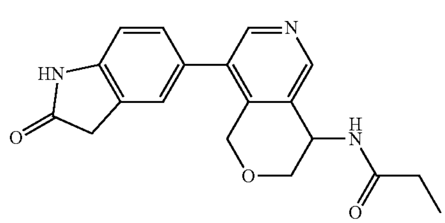 [SMILES: CCC(=O)NC1COCc2c(-c3ccc4c(c3)CC(=O)N4)cncc21] | N-[8-(2-Oxo-2,3-dihydro-1H-indol-5-yl)-3,4-dihydro-1H-pyrano[4,3-c]pyridin-4-yl]-propionamide, Enantiomer II |

TABLE 1-continued

| Cpd No | STRUCTURE | Name |
|---|---|---|
| 60 | 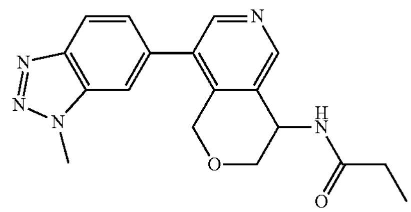 [SMILES: CCC(=O)NC1COCc2c(-c3ccc4nnn(C)c4c3)cncc21] | N-[8-(3-Methyl-3H-benzotriazol-5-yl)-3,4-dihydro-1H-pyrano[4,3-c]pyridin-4-yl]-propionamide, Enantiomer II |
| 61 | 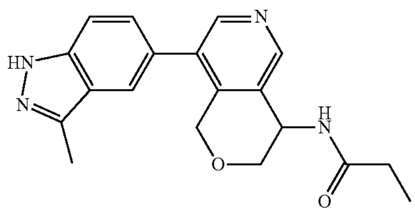 [SMILES: CCC(=O)NC1COCc2c(-c3ccc4[nH]nc(C)c4c3)cncc21] | N-[8-(3-Methyl-1H-indazol-5-yl)-3,4-dihydro-1H-pyrano[4,3-c]pyridin-4-yl]-propionamide, Enantiomer II |
| 62 | 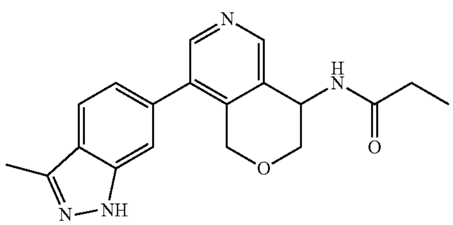 [SMILES: CCC(=O)NC1COCc2c(-c3ccc4c(C)n[nH]c4c3)cncc21] | N-[8-(3-Methyl-1H-indazol-6-yl)-3,4-dihydro-1H-pyrano[4,3-c]pyridin-4-yl]-propionamide, Enantiomer II |
| 63 | 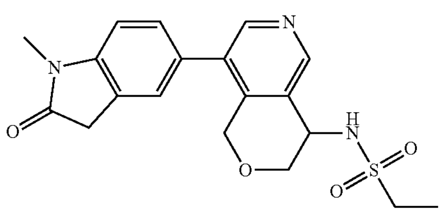 [SMILES: CCS(=O)(=O)NC1COCc2c(-c3ccc4c(c3)CC(=O)N4C)cncc21] | Ethanesulfonic acid [8-(1-methyl-2-oxo-2,3-dihydro-1H-indol-5-yl)-3,4-dihydro-1H-pyrano[4,3-c]pyridin-4-yl]-amide, Enantiomer II |
| 64 | 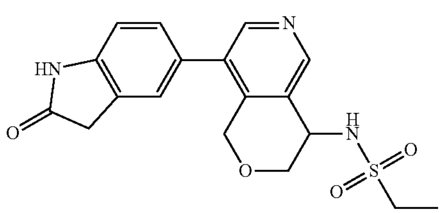 [SMILES: CCS(=O)(=O)NC1COCc2c(-c3ccc4c(c3)CC(=O)N4)cncc21] | Ethanesulfonic acid [8-(2-oxo-2,3-dihydro-1H-indol-5-yl)-3,4-dihydro-1H-pyrano[4,3-c]pyridin-4-yl]-amide, Enantiomer II |
| 65 | 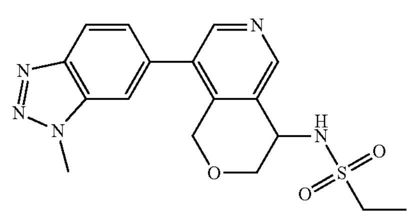 [SMILES: CCS(=O)(=O)NC1COCc2c(-c3ccc4nnn(C)c4c3)cncc21] | Ethanesulfonic acid [8-(3-methyl-3H-benzotriazol-5-yl)-3,4-dihydro-1H-pyrano[4,3-c]pyridin-4-yl]-amide, Enantiomer II |
| 66 | 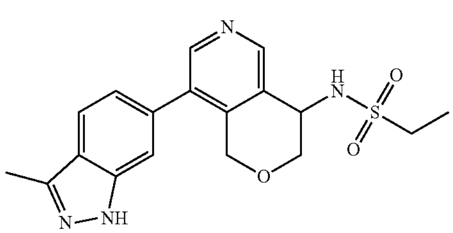 [SMILES: CCS(=O)(=O)NC1COCc2c(-c3ccc4c(C)n[nH]c4c3)cncc21] | Ethanesulfonic acid [8-(3-methyl-1H-indazol-6-yl)-3,4-dihydro-1H-pyrano[4,3-c]pyridin-4-yl]-amide, Enantiomer II |

TABLE 1-continued

| Cpd No | STRUCTURE | Name |
|---|---|---|
| 67 | 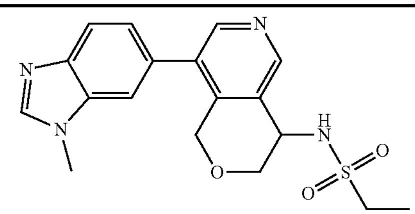 | Ethanesulfonic acid [8-(3-methyl-3H-benzoimidazol-5-yl)-3,4-dihydro-1H-pyrano[4,3-c]pyridin-4-yl]-amide, Enantiomer II |
| 68 | 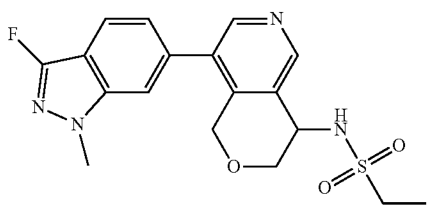 [SMILES: CCS(=O)(=O)NC1COCc2c(-c3ccc4c(F)nn(C)c4c3)cncc21] | Ethanesulfonic acid [8-(3-fluoro-1-methyl-1H-indazol-6-yl)-3,4-dihydro-1H-pyrano[4,3-c]pyridin-4-yl]-amide, Enantiomer II |
| 69 | 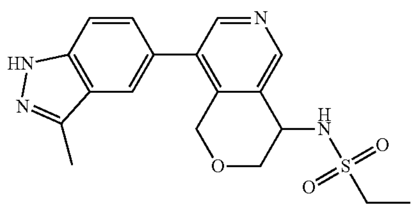 [SMILES: CCS(=O)(=O)NC1COCc2c(-c3ccc4[nH]nc(C)c4c3)cncc21] | Ethanesulfonic acid [8-(3-methyl-1H-indazol-5-yl)-3,4-dihydro-1H-pyrano[4,3-c]pyridin-4-yl]-amide, Enantiomer II |
| 70 | 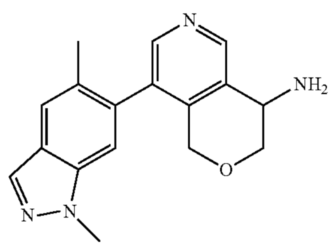 [SMILES: Cc1cc2cnn(C)c2cc1-c1cncc2c1COCC2N] | 8-(1,5-Dimethyl-1H-indazol-6-yl)-3,4-dihydro-1H-pyrano[4,3-c]pyridin-4-ylamine, Enantiomer II |
| 71 | 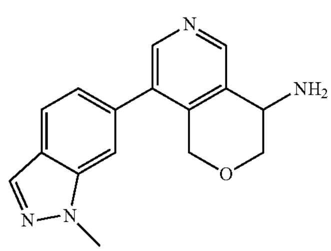 [SMILES: Cn1ncc2ccc(-c3cncc4c3COCC4N)cc21] | 8-(1-Methyl-1H-indazol-6-yl)-3,4-dihydro-1H-pyrano[4,3-c]pyridin-4-ylamine, Enantiomer II |
| 72 | 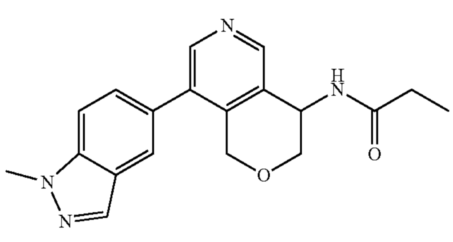 [SMILES: CCC(=O)NC1COCc2c(-c3ccc4c(cnn4C)c3)cncc21] | N-[8-(1-Methyl-1H-indazol-5-yl)-3,4-dihydro-1H-pyrano[4,3-c]pyridin-4-yl]-propionamide, Enantiomer I |
| 73 | 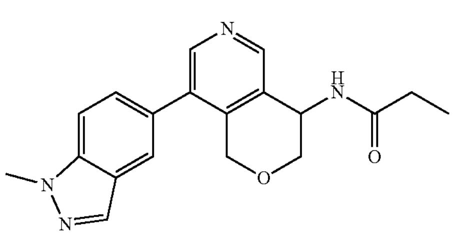 [SMILES: CCC(=O)NC1COCc2c(-c3ccc4c(cnn4C)c3)cncc21] | N-[8-(1-Methyl-1H-indazol-5-yl)-3,4-dihydro-1H-pyrano[4,3-c]pyridin-4-yl]-propionamide, Enantiomer II |

TABLE 1-continued

| Cpd No | STRUCTURE | Name |
|---|---|---|
| 74 | 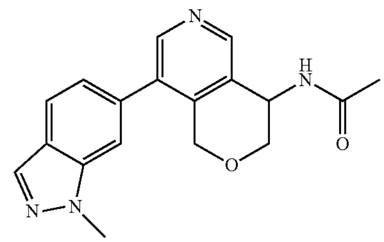 [SMILES: CC(=O)NC1COCc2c(-c3ccc4cnn(C)c4c3)cncc21] | N-[8-(1-Methyl-1H-indazol-6-yl)-3,4-dihydro-1H-pyrano[4,3-c]pyridin-4-yl]-acetamide, Enantiomer II |
| 75 | 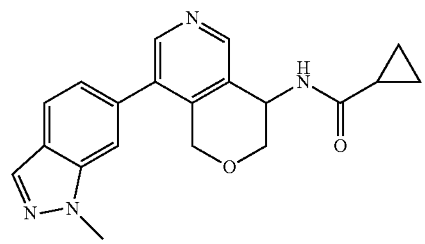 [SMILES: Cn1ncc2ccc(-c3cncc4c3COCC4NC(=O)C3CC3)cc21] | Cyclopropanecarboxylic acid [8-(1-methyl-1H-indazol-6-yl)-3,4-dihydro-1H-pyrano[4,3-c]pyridin-4-yl]-amide, Enantiomer II |
| 76 | 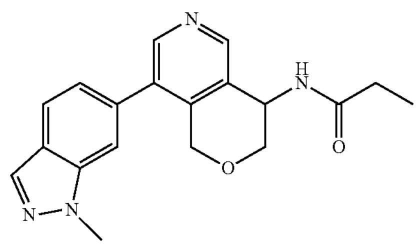 [SMILES: CCC(=O)NC1COCc2c(-c3ccc4cnn(C)c4c3)cncc21] | N-[8-(1-Methyl-1H-indazol-6-yl)-3,4-dihydro-1H-pyrano[4,3-c]pyridin-4-yl]-propionamide, Enantiomer II |
| 77 | 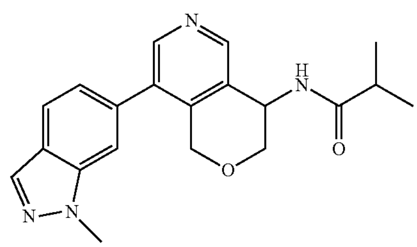 [SMILES: CC(C)C(=O)NC1COCc2c(-c3ccc4cnn(C)c4c3)cncc21] | N-[8-(1-Methyl-1H-indazol-6-yl)-3,4-dihydro-1H-pyrano[4,3-c]pyridin-4-yl]-isobutyramide, Enantiomer II |
| 78 | 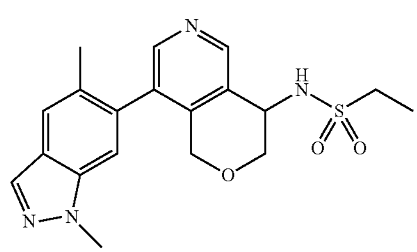 [SMILES: CCS(=O)(=O)NC1COCc2c(-c3cc4c(cnn4C)cc3C)cncc21] | Ethanesulfonic acid [8-(1,5-dimethyl-1H-indazol-6-yl)-3,4-dihydro-1H-pyrano[4,3-c]pyridin-4-yl]-amide, Enantiomer I |
| 79 | 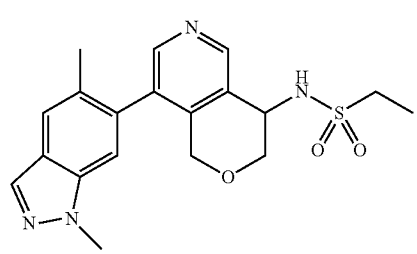 [SMILES: CCS(=O)(=O)NC1COCc2c(-c3cc4c(cnn4C)cc3C)cncc21] | Ethanesulfonic acid [8-(1,5-dimethyl-1H-indazol-6-yl)-3,4-dihydro-1H-pyrano[4,3-c]pyridin-4-yl]-amide, Enantiomer II |

TABLE 1-continued

| Cpd No | STRUCTURE | Name |
|---|---|---|
| 80 | 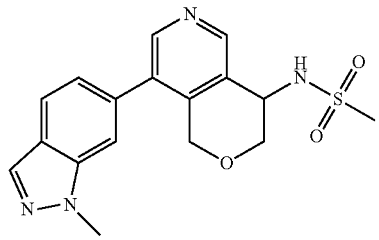 [SMILES: Cn1ncc2ccc(-c3cncc4c3COCC4NS(C)(=O)=O)cc21] | N-[8-(1-Methyl-1H-indazol-6-yl)-3,4-dihydro-1H-pyrano[4,3-c]pyridin-4-yl]-methanesulfonamide, Enantiomer I |
| 81 | 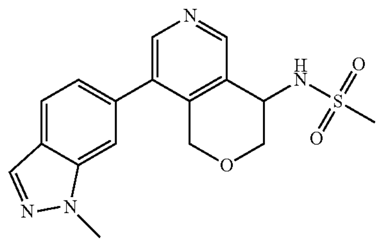 [SMILES: Cn1ncc2ccc(-c3cncc4c3COCC4NS(C)(=O)=O)cc21] | N-[8-(1-Methyl-1H-indazol-6-yl)-3,4-dihydro-1H-pyrano[4,3-c]pyridin-4-yl]-methanesulfonamide, Enantiomer II |
| 82 | 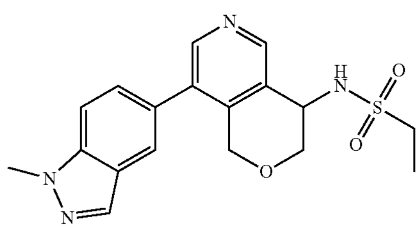 [SMILES: CCS(=O)(=O)NC1COCc2c(-c3ccc4c(cnn4C)c3)cncc21] | Ethanesulfonic acid [8-(1-methyl-1H-indazol-5-yl)-3,4-dihydro-1H-pyrano[4,3-c]pyridin-4-yl]-amide, Enantiomer II |
| 83 | 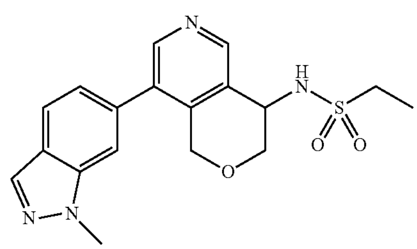 [SMILES: CCS(=O)(=O)NC1COCc2c(-c3ccc4cnn(C)c4c3)cncc21] | Ethanesulfonic acid [8-(1-methyl-1H-indazol-6-yl)-3,4-dihydro-1H-pyrano[4,3-c]pyridin-4-yl]-amide, Enantiomer II |
| 84 | 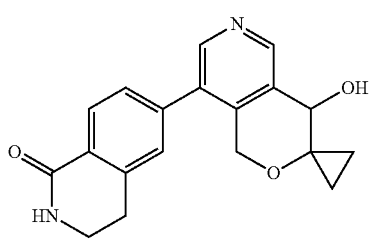 [SMILES: O=C1NCCc2cc(-c3cncc4c3COC3(CC3)C4O)ccc21] | 6-[4-hydroxyspiro[1,4-dihydropyrano[4,3-c]pyridine-3,1'-cyclopropane]-8-yl]-3,4-dihydro-2H-isoquinolin-1-one, Enantiomer I |
| 85 | 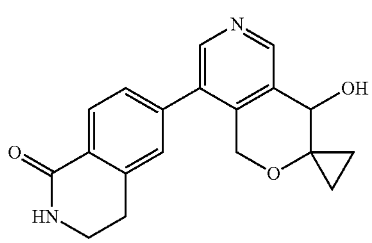 [SMILES: O=C1NCCc2cc(-c3cncc4c3COC3(CC3)C4O)ccc21] | 6-[4-hydroxyspiro[1,4-dihydropyrano[4,3-c]pyridine-3,1'-cyclopropane]-8-yl]-3,4-dihydro-2H-isoquinolin-1-one, Enantiomer II |

TABLE 1-continued

| Cpd No | STRUCTURE | Name |
|---|---|---|
| 86 | 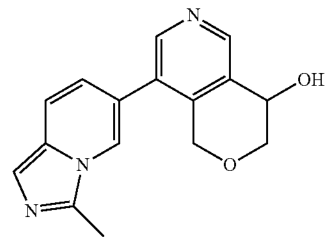 [SMILES: Cc1ncc2ccc(-c3cncc4c3COCC4O)cn12] | 8-(3-Methyl-imidazo[1,5-a]pyridin-6-yl)-3,4-dihydro-1H-pyrano[4,3-c]pyridin-4-ol, Enantiomer I |
| 87 | 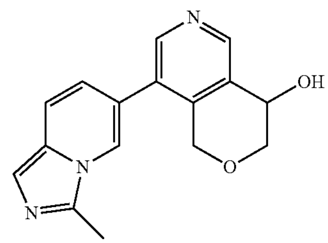 [SMILES: Cc1ncc2ccc(-c3cncc4c3COCC4O)cn12] | 8-(3-Methyl-imidazo[1,5-a]pyridin-6-yl)-3,4-dihydro-1H-pyrano[4,3-c]pyridin-4-ol, Enantiomer II |
| 88 | 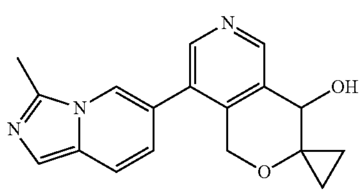 [SMILES: Cc1ncc2ccc(-c3cncc4c3COC3(CC3)C4O)cn12] | 8-(3-methylimidazo[1,5-a]pyridin-6-yl)spiro[1,4-dihydropyrano[4,3-c]pyridine-3,1'-cyclopropane]-4-ol, Enantiomer I |
| 89 | 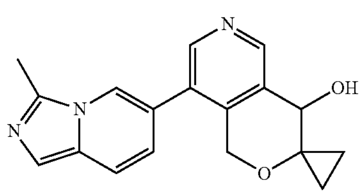 [SMILES: Cc1ncc2ccc(-c3cncc4c3COC3(CC3)C4O)cn12] | 8-(3-methylimidazo[1,5-a]pyridin-6-yl)spiro[1,4-dihydropyrano[4,3-c]pyridine-3,1'-cyclopropane]-4-ol, Enantiomer II |
| 90 | 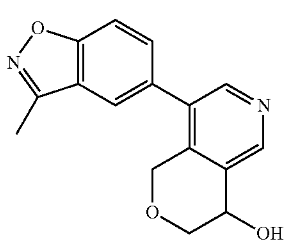 [SMILES: Cc1noc2ccc(-c3cncc4c3COCC4O)cc12] | 8-(3-Methyl-benzo[d]isoxazol-5-yl)-3,4-dihydro-1H-pyrano[4,3-c]pyridin-4-ol, Enantiomer II |
| 91 | 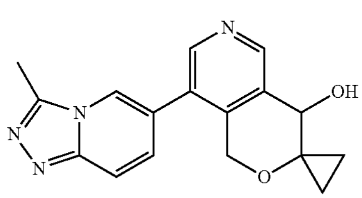 [SMILES: Cc1nnc2ccc(-c3cncc4c3COC3(CC3)C4O)cn12] | 8-(3-methyl-[1,2,4]triazolo[4,3-a]pyridin-6-yl)spiro[1,4-dihydropyrano[4,3-c]pyridine-3,1'-cyclopropane]-4-ol, Enantiomer I |

TABLE 1-continued

| Cpd No | STRUCTURE | Name |
|---|---|---|
| 92 | 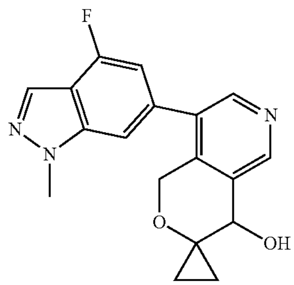 [SMILES: Cn1ncc2c(F)cc(-c3cncc4c3COC3(CC3)C4O)cc21] | 8-(4-fluoro-1-methyl-indazol-6-yl)spiro[1,4-dihydropyrano[4,3-c]pyridine-3,1'-cyclopropane]-4-ol, Enantiomer II |
| 93 | 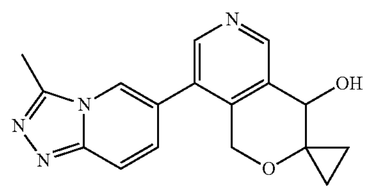 | 8-(3-methyl-[1,2,4]triazolo[4,3-a]pyridin-6-yl)spiro[1,4-dihydropyrano[4,3-c]pyridine-3,1'-cyclopropane]-4-ol, Enantiomer II |
| 94 | 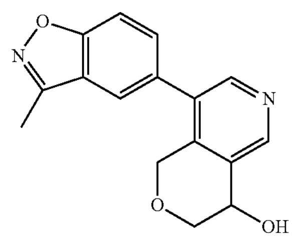 [SMILES: Cc1noc2ccc(-c3cncc4c3COCC4O)cc12] | 8-(3-Methyl-benzo[d]isoxazol-5-yl)-3,4-dihydro-1H-pyrano[4,3-c]pyridin-4-ol, Enantiomer I |
| 95 | 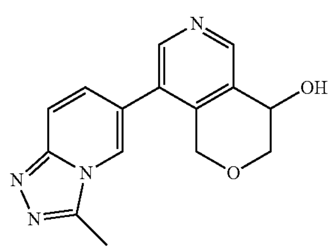 [SMILES: Cc1nnc2ccc(-c3cncc4c3COCC4O)cn12] | 8-(3-Methyl-[1,2,4]triazolo[4,3-a]pyridin-6-yl)-3,4-dihydro-1H-pyrano[4,3-c]pyridin-4-ol, Enantiomer I |
| 96 | 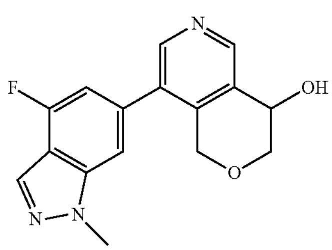 [SMILES: Cn1ncc2c(F)cc(-c3cncc4c3COCC4O)cc21] | 8-(4-Fluoro-1-methyl-1H-indazol-6-yl)-3,4-dihydro-1H-pyrano[4,3-c]pyridin-4-ol, Enantiomer II |
| 97 | 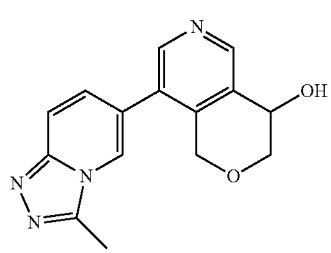 [SMILES: Cc1nnc2ccc(-c3cncc4c3COCC4O)cn12] | 8-(3-Methyl-[1,2,4]triazolo[4,3-a]pyridin-6-yl)-3,4-dihydro-1H-pyrano[4,3-c]pyridin-4-ol, Enantiomer II |

TABLE 1-continued

| Cpd No | STRUCTURE | Name |
|---|---|---|
| 98 | 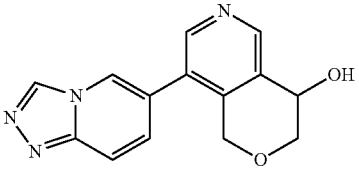 [SMILES: OC1COCc2c(-c3ccc4nncn4c3)cncc21] | 8-[1,2,4]Triazolo[4,3-a]pyridin-6-yl-3,4-dihydro-1H-pyrano[4,3-c]pyridin-4-ol, Enantiomer II |
| 99 | 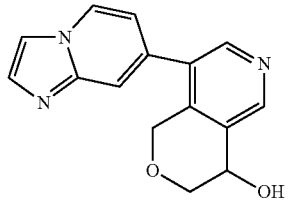 [SMILES: OC1COCc2c(-c3ccn4ccnc4c3)cncc21] | 8-Imidazo[1,2-a]pyridin-7-yl-3,4-dihydro-1H-pyrano[4,3-c]pyridin-4-ol, Enantiomer I |
| 100 | 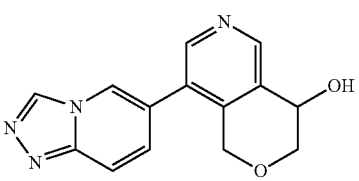 [SMILES: OC1COCc2c(-c3ccc4nncn4c3)cncc21] | 8-[1,2,4]Triazolo[4,3-a]pyridin-6-yl-3,4-dihydro-1H-pyrano[4,3-c]pyridin-4-ol, Enantiomer I |
| 101 | 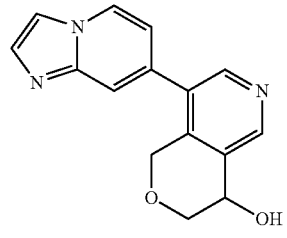 [SMILES: OC1COCc2c(-c3ccn4ccnc4c3)cncc21] | 8-Imidazo[1,2-a]pyridin-7-yl-3,4-dihydro-1H-pyrano[4,3-c]pyridin-4-ol, Enantiomer II |
| 102 | 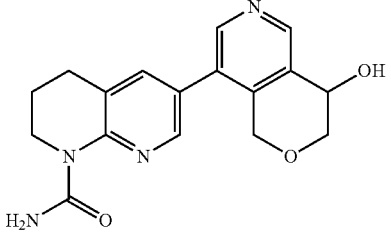 [SMILES: NC(=O)N1CCCc2cc(-c3cncc4c3COCC4O)cnc21] | 6-(4-Hydroxy-3,4-dihydro-1H-pyrano[4,3-c]pyridin-8-yl)-3,4-dihydro-2H-[1,8]naphthyridine-1-carboxylic acid amide |
| 103 | 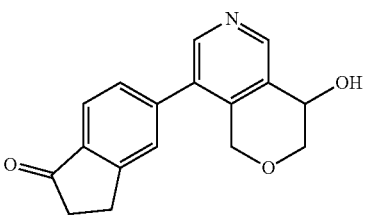 [SMILES: O=C1CCc2cc(-c3cncc4c3COCC4O)ccc21] | 5-(4-Hydroxy-3,4-dihydro-1H-pyrano[4,3-c]pyridin-8-yl)-indan-1-one, Enantiomer II |
| 104 | 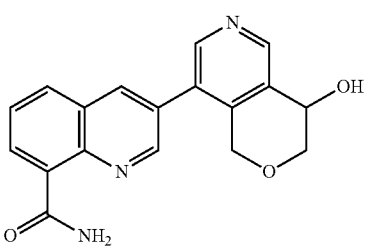 [SMILES: NC(=O)c1cccc2cc(-c3cncc4c3COCC4O)cnc12] | 3-(4-Hydroxy-3,4-dihydro-1H-pyrano[4,3-c]pyridin-8-yl)-quinoline-8-carboxylic acid amide, Enantiomer I |

TABLE 1-continued

| Cpd No | STRUCTURE | Name |
|---|---|---|
| 105 | 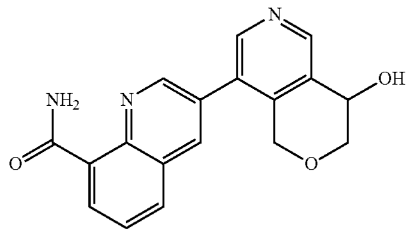 [SMILES: NC(=O)c1cccc2cc(-c3cncc4c3COCC4O)cnc12] | 3-(4-Hydroxy-3,4-dihydro-1H-pyrano[4,3-c]pyridin-8-yl)-quinoline-8-carboxylic acid amide, Enantiomer II |
| 106 | 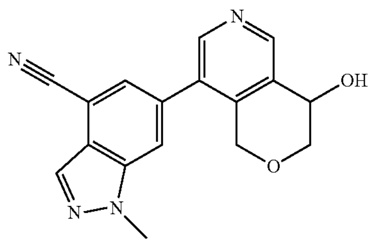 [SMILES: Cn1ncc2c(C#N)cc(-c3cncc4c3COCC4O)cc21] | 6-(4-Hydroxy-3,4-dihydro-1H-pyrano[4,3-c]pyridin-8-yl)-1-methyl-1H-indazole-4-carbonitrile, Enantiomer II |
| 107 | 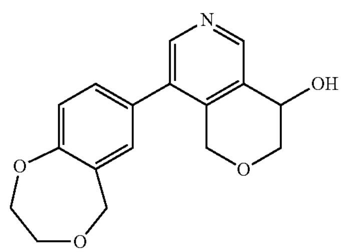 [SMILES: OC1COCc2c(-c3ccc4c(c3)COCCO4)cncc21] | 8-(2,3-Dihydro-5H-benzo[e][1,4]dioxepin-7-yl)-3,4-dihydro-1H-pyrano[4,3-c]pyridin-4-ol, Enantiomer II |
| 108 | 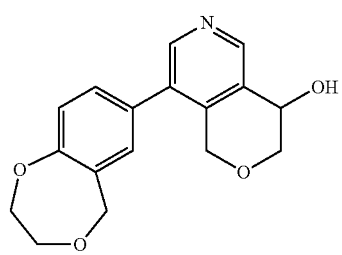 [SMILES: OC1COCc2c(-c3ccc4c(c3)COCCO4)cncc21] | 8-(2,3-Dihydro-5H-benzo[e][1,4]dioxepin-7-yl)-3,4-dihydro-1H-pyrano[4,3-c]pyridin-4-ol, Enantiomer I |
| 109 | 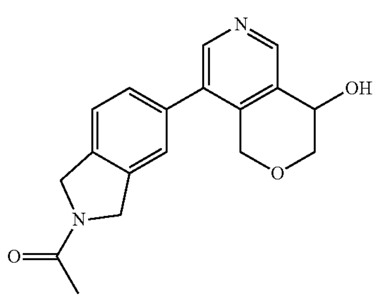 [SMILES: CC(=O)N1Cc2ccc(-c3cncc4c3COCC4O)cc2C1] | 1-[5-(4-Hydroxy-3,4-dihydro-1H-pyrano[4,3-c]pyridin-8-yl)-1,3-dihydro-isoindol-2-yl]-ethanone, Enantiomer II |
| 110 | 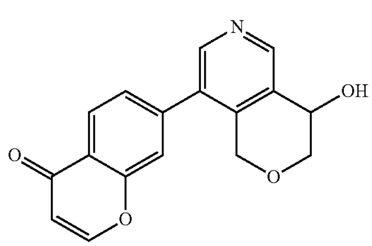 [SMILES: O=c1ccoc2cc(-c3cncc4c3COCC4O)ccc12] | 7-(4-Hydroxy-3,4-dihydro-1H-pyrano[4,3-c]pyridin-8-yl)-chromen-4-one, Enantiomer II |

TABLE 1-continued

| Cpd No | STRUCTURE | Name |
|---|---|---|
| 111 | 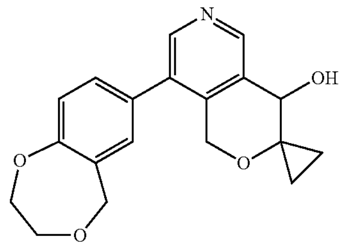 [SMILES: OC1c2cncc(-c3ccc4c(c3)COCCO4)c2COC12CC2] | 8-(3,5-dihydro-2H-1,4-benzo[e][1,4]dioxepin-7-yl)spiro[1,4-dihydropyrano[4,3-c]pyridine-3,1'-cyclopropane]-4-ol, Enantiomer I |
| 112 | 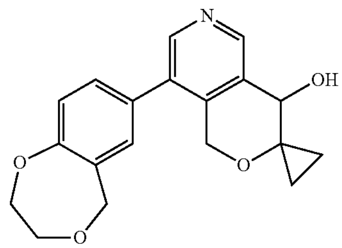 [SMILES: OC1c2cncc(-c3ccc4c(c3)COCCO4)c2COC12CC2] | 8-(3,5-dihydro-2H-1,4-benzo[e][1,4]dioxepin-7-yl)spiro[1,4-dihydropyrano[4,3-c]pyridine-3,1'-cyclopropane]-4-ol, Enantiomer II |
| 113 | 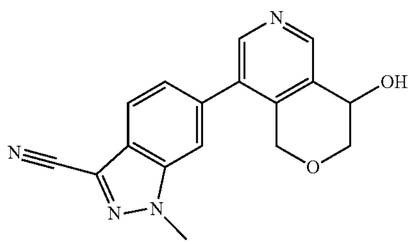 [SMILES: Cn1nc(C#N)c2ccc(-c3cncc4c3COCC4O)cc21] | 6-(4-Hydroxy-3,4-dihydro-1H-pyrano[4,3-c]pyridin-8-yl)-1-methyl-1H-indazole-3-carbonitrile, Enantiomer II |
| 114 | 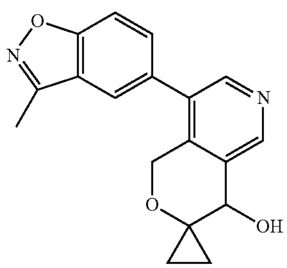 [SMILES: Cc1noc2ccc(-c3cncc4c3COC3(CC3)C4O)cc12] | 8-(3-methyl-1,2-benzoxazol-5-yl)spiro[1,4-dihydropyrano[4,3-c]pyridine-3,1'-cyclopropane]-4-ol, Enantiomer II |
| 115 | 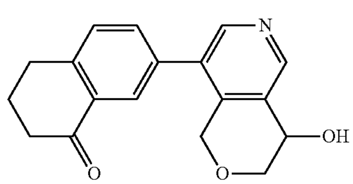 [SMILES: O=C1CCCc2ccc(-c3cncc4c3COCC4O)cc21] | 7-(4-Hydroxy-3,4-dihydro-1H-pyrano[4,3-c]pyridin-8-yl)-3,4-dihydro-2H-naphthalen-1-one, Enantiomer I |
| 116 | 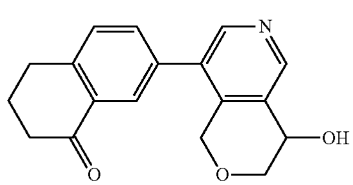 | 7-(4-Hydroxy-3,4-dihydro-1H-pyrano[4,3-c]pyridin-8-yl)-3,4-dihydro-2H-naphthalen-1-one, Enantiomer II |
| 117 | 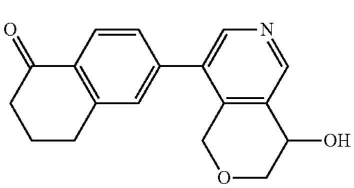 [SMILES: O=C1CCCc2cc(-c3cncc4c3COCC4O)ccc21] | 6-(4-Hydroxy-3,4-dihydro-1H-pyrano[4,3-c]pyridin-8-yl)-3,4-dihydro-2H-naphthalen-1-one, Enantiomer I |

TABLE 1-continued

| Cpd No | STRUCTURE | Name |
|---|---|---|
| 118 | 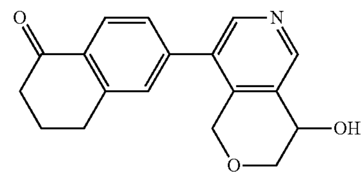 [SMILES: O=C1CCCc2cc(-c3cncc4c3COCC4O)ccc21] | 6-(4-Hydroxy-3,4-dihydro-1H-pyrano[4,3-c]pyridin-8-yl)-3,4-dihydro-2H-naphthalen-1-one, Enantiomer II |
| 119 | 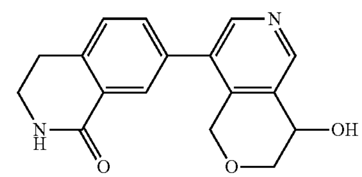 [SMILES: O=C1NCCc2ccc(-c3cncc4c3COCC4O)cc21] | 7-(4-Hydroxy-3,4-dihydro-1H-pyrano[4,3-c]pyridin-8-yl)-3,4-dihydro-2H-isoquinolin-1-one, Enantiomer II |
| 120 | 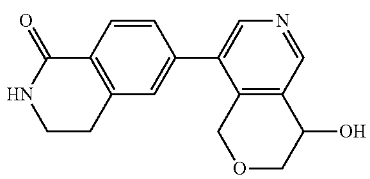 [SMILES: O=C1NCCc2cc(-c3cncc4c3COCC4O)ccc21] | 6-(4-Hydroxy-3,4-dihydro-1H-pyrano[4,3-c]pyridin-8-yl)-3,4-dihydro-2H-isoquinolin-1-one, Enantiomer I |
| 121 | 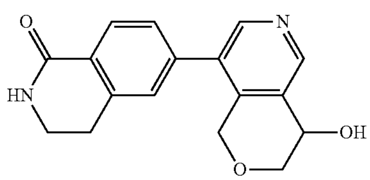 [SMILES: O=C1NCCc2cc(-c3cncc4c3COCC4O)ccc21] | 6-(4-Hydroxy-3,4-dihydro-1H-pyrano[4,3-c]pyridin-8-yl)-3,4-dihydro-2H-isoquinolin-1-one, Enantiomer II |
| 122 | 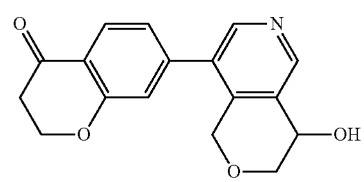 [SMILES: O=C1CCOc2cc(-c3cncc4c3COCC4O)ccc21] | 7-(4-Hydroxy-3,4-dihydro-1H-pyrano[4,3-c]pyridin-8-yl)-chroman-4-one, Enantiomer I |
| 123 | 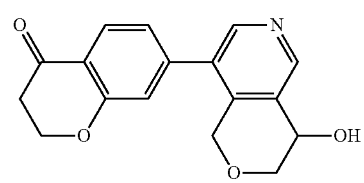 [SMILES: O=C1CCOc2cc(-c3cncc4c3COCC4O)ccc21] | 7-(4-Hydroxy-3,4-dihydro-1H-pyrano[4,3-c]pyridin-8-yl)-chroman-4-one, Enantiomer II |
| 124 | 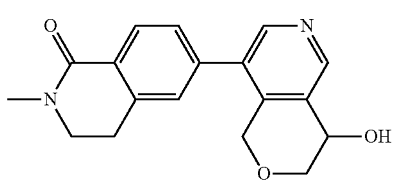 [SMILES: CN1CCc2cc(-c3cncc4c3COCC4O)ccc2C1=O] | 6-(4-Hydroxy-3,4-dihydro-1H-pyrano[4,3-c]pyridin-8-yl)-2-methyl-3,4-dihydro-2H-isoquinolin-1-one, Enantiomer II |
| 125 | 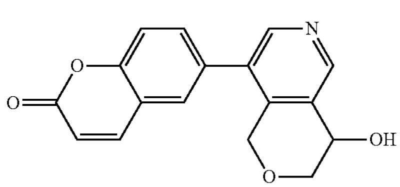 [SMILES: O=c1ccc2cc(-c3cncc4c3COCC4O)ccc2o1] | 6-(4-Hydroxy-3,4-dihydro-1H-pyrano[4,3-c]pyridin-8-yl)-chromen-2-one, Enantiomer I |

TABLE 1-continued

| Cpd No | STRUCTURE | Name |
|---|---|---|
| 126 | 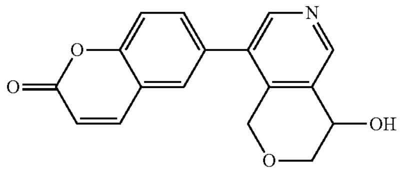 [SMILES: O=c1ccc2cc(-c3cncc4c3COCC4O)ccc2o1] | 6-(4-Hydroxy-3,4-dihydro-1H-pyrano[4,3-c]pyridin-8-yl)-chromen-2-one, Enantiomer II |
| 127 | 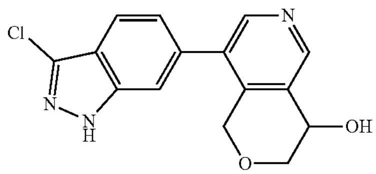 [SMILES: OC1COCc2c(-c3ccc4c(Cl)n[nH]c4c3)cncc21] | 8-(3-Chloro-1H-indazol-6-yl)-3,4-dihydro-1H-pyrano[4,3-c]pyridin-4-ol, Enantiomer II |
| 128 | 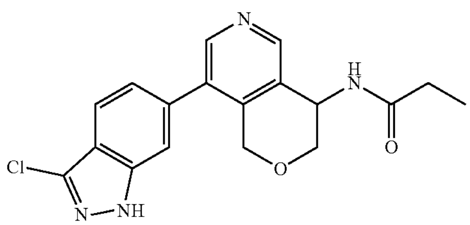 [SMILES: CCC(=O)NC1COCc2c(-c3ccc4c(Cl)n[nH]c4c3)cncc21] | N-[8-(3-Chloro-1H-indazol-6-yl)-3,4-dihydro-1H-pyrano[4,3-c]pyridin-4-yl]-propionamide, Enantiomer II |
| 129 | 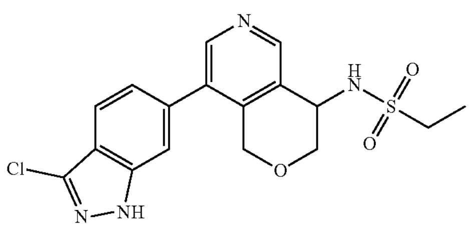 [SMILES: CCS(=O)(=O)NC1COCc2c(-c3ccc4c(Cl)n[nH]c4c3)cncc21] | Ethanesulfonic acid [8-(3-chloro-1H-indazol-6-yl)-3,4-dihydro-1H-pyrano[4,3-c]pyridin-4-yl]-amide, Enantiomer II |
| 130 | 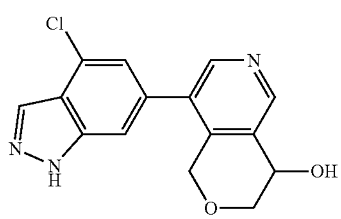 [SMILES: OC1COCc2c(-c3cc(Cl)c4cn[nH]c4c3)cncc21] | 8-(4-Chloro-1H-indazol-6-yl)-3,4-dihydro-1H-pyrano[4,3-c]pyridin-4-ol, Enantiomer I |
| 131 | 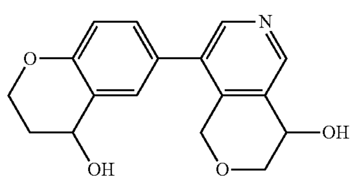 [SMILES: OC1CCOc2ccc(-c3cncc4c3COCC4O)cc21] | 8-(4-Hydroxy-chroman-6-yl)-3,4-dihydro-1H-pyrano[4,3-c]pyridin-4-ol, Stereoisomer I |
| 132 | 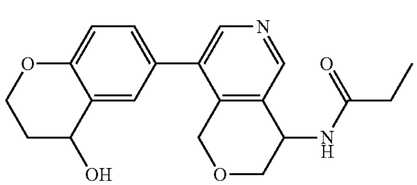 [SMILES: CCC(=O)NC1COCc2c(-c3ccc4c(c3)C(O)CCO4)cncc21] | N-[8-(4-Hydroxy-chroman-6-yl)-3,4-dihydro-1H-pyrano[4,3-c]pyridin-4-yl]-propionamide, Stereoisomer I |

TABLE 1-continued

| Cpd No | STRUCTURE | Name |
|---|---|---|
| 133 | 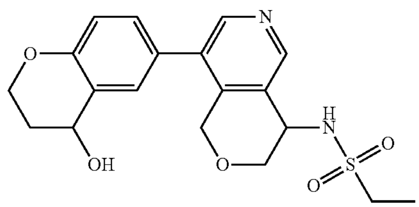 [SMILES: CCS(=O)(=O)NC1COCc2c(-c3ccc4c(c3)C(O)CCO4)cncc21] | Ethanesulfonic acid [8-(4-hydroxy-chroman-6-yl)-3,4-dihydro-1H-pyrano[4,3-c]pyridin-4-yl]-amide, Stereoisomer I |
| 134 | 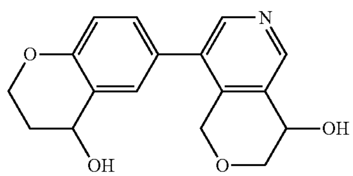 [SMILES: OC1CCOc2ccc(-c3cncc4c3COCC4O)cc21] | 8-(4-Hydroxy-chroman-6-yl)-3,4-dihydro-1H-pyrano[4,3-c]pyridin-4-ol, Stereoisomer II |
| 135 | 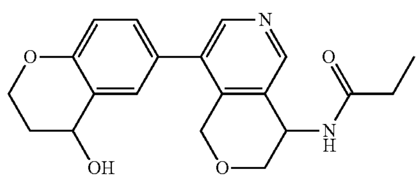 [SMILES: CCC(=O)NC1COCc2c(-c3ccc4c(c3)C(O)CCO4)cncc21] | N-[8-(4-Hydroxy-chroman-6-yl)-3,4-dihydro-1H-pyrano[4,3-c]pyridin-4-yl]-propionamide, Stereoisomer II |
| 136 | 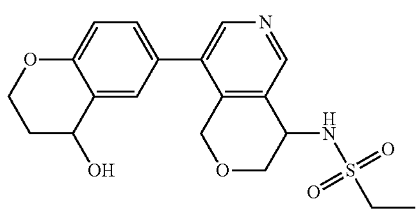 [SMILES: CCS(=O)(=O)NC1COCc2c(-c3ccc4c(c3)C(O)CCO4)cncc21] | Ethanesulfonic acid [8-(4-hydroxy-chroman-6-yl)-3,4-dihydro-1H-pyrano[4,3-c]pyridin-4-yl]-amide, Stereoisomer II |
| 137 | 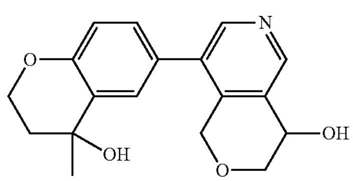 [SMILES: CC1(O)CCOc2ccc(-c3cncc4c3COCC4O)cc21] | 8-(4-Hydroxy-4-methyl-chroman-6-yl)-3,4-dihydro-1H-pyrano[4,3-c]pyridin-4-ol, Stereoisomer I |
| 138 | 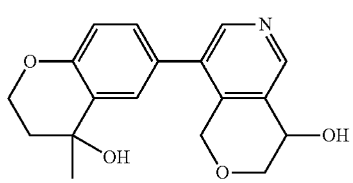 [SMILES: CC1(O)CCOc2ccc(-c3cncc4c3COCC4O)cc21] | 8-(4-Hydroxy-4-methyl-chroman-6-yl)-3,4-dihydro-1H-pyrano[4,3-c]pyridin-4-ol, Stereoisomer II |
| 139 | 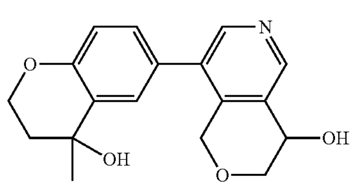 [SMILES: CC1(O)CCOc2ccc(-c3cncc4c3COCC4O)cc21] | 8-(4-Hydroxy-4-methyl-chroman-6-yl)-3,4-dihydro-1H-pyrano[4,3-c]pyridin-4-ol, Stereoisomer III |
| 140 | 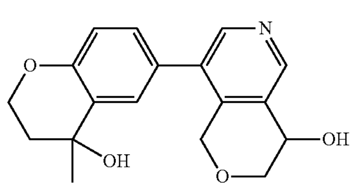 [SMILES: CC1(O)CCOc2ccc(-c3cncc4c3COCC4O)cc21] | 8-(4-Hydroxy-4-methyl-chroman-6-yl)-3,4-dihydro-1H-pyrano[4,3-c]pyridin-4-ol, Stereoisomer IV |

TABLE 1-continued

| Cpd No | STRUCTURE | Name |
|---|---|---|
| 141 | 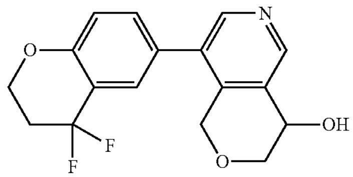 [SMILES: OC1COCc2c(-c3ccc4c(c3)C(F)(F)CCO4)cncc21] | 8-(4,4-Difluoro-chroman-6-yl)-3,4-dihydro-1H-pyrano[4,3-c]pyridin-4-ol, Enantiomer II |
| 142 | 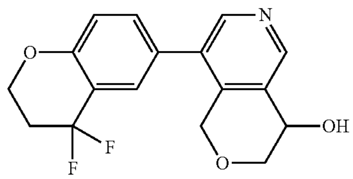 [SMILES: OC1COCc2c(-c3ccc4c(c3)C(F)(F)CCO4)cncc21] | 8-(4,4-Difluoro-chroman-6-yl)-3,4-dihydro-1H-pyrano[4,3-c]pyridin-4-ol, Enantiomer I |
| 143 | 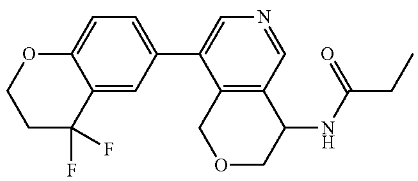 [SMILES: CCC(=O)NC1COCc2c(-c3ccc4c(c3)C(F)(F)CCO4)cncc21] | N-[8-(4,4-Difluoro-chroman-6-yl)-3,4-dihydro-1H-pyrano[4,3-c]pyridin-4-yl]-propionamide, Enantiomer II |
| 144 | 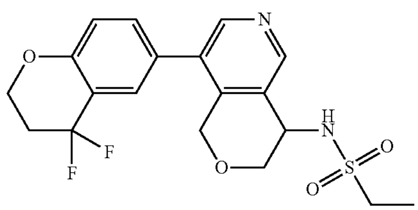 [SMILES: CCS(=O)(=O)NC1COCc2c(-c3ccc4c(c3)C(F)(F)CCO4)cncc21] | Ethanesulfonic acid [8-(4,4-difluoro-chroman-6-yl)-3,4-dihydro-1H-pyrano[4,3-c]pyridin-4-yl]-amide, Enantiomer II |
| 145 | 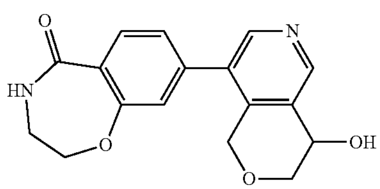 [SMILES: O=C1NCCOc2cc(-c3cncc4c3COCC4O)ccc21] | 8-(4-Hydroxy-3,4-dihydro-1H-pyrano[4,3-c]pyridin-8-yl)-3,4-dihydro-2H-benzo[f][1,4]oxazepin-5-one, Enantiomer II |
| 146 | 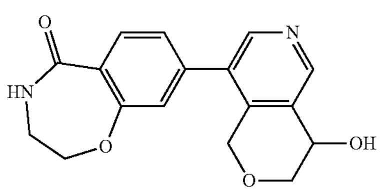 [SMILES: O=C1NCCOc2cc(-c3cncc4c3COCC4O)ccc21] | 8-(4-Hydroxy-3,4-dihydro-1H-pyrano[4,3-c]pyridin-8-yl)-3,4-dihydro-2H-benzo[f][1,4]oxazepin-5-one, Enantiomer I |
| 147 | 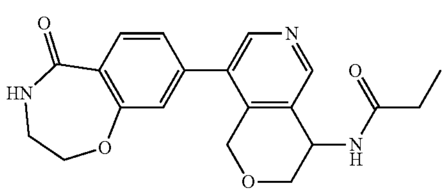 [SMILES: CCC(=O)NC1COCc2c(-c3ccc4c(c3)OCCNC4=O)cncc21] | N-[8-(5-Oxo-2,3,4,5-tetrahydro-benzo[f][1,4]oxazepin-8-yl)-3,4-dihydro-1H-pyrano[4,3-c]pyridin-4-yl]-propionamide, Enantiomer II |
| 148 | 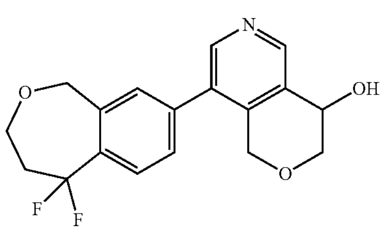 [SMILES: OC1COCc2c(-c3ccc4c(c3)COCCC4(F)F)cncc21] | 8-(5,5-Difluoro-1,3,4,5-tetrahydro-benzo[c]oxepin-8-yl)-3,4-dihydro-1H-pyrano[4,3-c]pyridin-4-ol, Enantiomer II |

TABLE 1-continued

| Cpd No | STRUCTURE | Name |
|---|---|---|
| 149 | 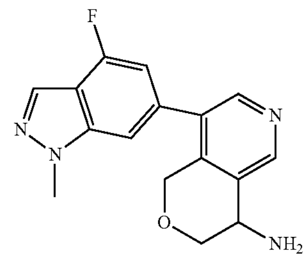 [SMILES: Cn1ncc2c(F)cc(-c3cncc4c3COCC4N)cc21] | 8-(4-Fluoro-1-methyl-1H-indazol-6-yl)-3,4-dihydro-1H-pyrano[4,3-c]pyridin-4-ylamine, Enantiomer II |
| 150 | 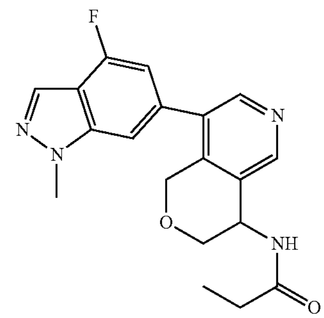 [SMILES: CCC(=O)NC1COCc2c(-c3cc(F)c4cnn(C)c4c3)cncc21] | N-[8-(4-Fluoro-1-methyl-1H-indazol-6-yl)-3,4-dihydro-1H-pyrano[4,3-c]pyridin-4-yl]-propionamide, Enantiomer II |
| 151 | 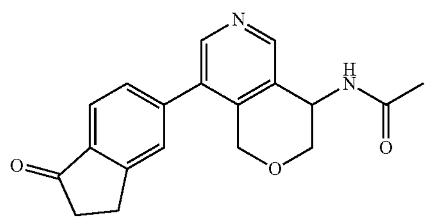 [SMILES: CC(=O)NC1COCc2c(-c3ccc4c(c3)CCC4=O)cncc21] | N-[8-(1-Oxo-indan-5-yl)-3,4-dihydro-1H-pyrano[4,3-c]pyridin-4-yl]-acetamide, Enantiomer I |
| 152 | 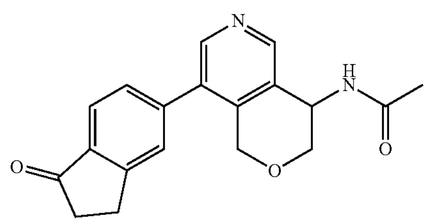 [SMILES: CC(=O)NC1COCc2c(-c3ccc4c(c3)CCC4=O)cncc21] | N-[8-(1-Oxo-indan-5-yl)-3,4-dihydro-1H-pyrano[4,3-c]pyridin-4-yl]-acetamide, Enantiomer II |
| 153 | 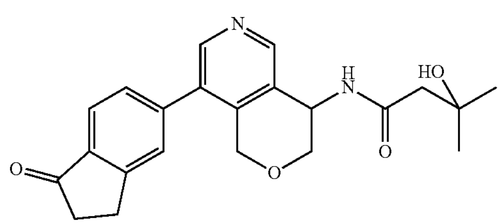 [SMILES: CC(C)(O)CC(=O)NC1COCc2c(-c3ccc4c(c3)CCC4=O)cncc21] | 3-Hydroxy-3-methyl-N-[8-(1-oxo-indan-5-yl)-3,4-dihydro-1H-pyrano[4,3-c]pyridin-4-yl]-butyramide, Enantiomer II |
| 154 | 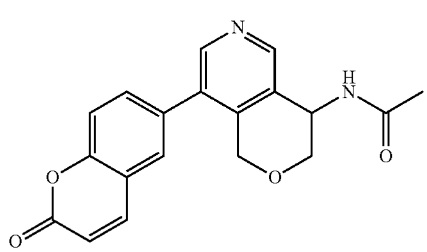 [SMILES: CC(=O)NC1COCc2c(-c3ccc4oc(=O)ccc4c3)cncc21] | N-[8-(2-Oxo-2H-chromen-6-yl)-3,4-dihydro-1H-pyrano[4,3-c]pyridin-4-yl]-acetamide, Enantiomer II |

TABLE 1-continued

| Cpd No | STRUCTURE | Name |
|---|---|---|
| 155 | 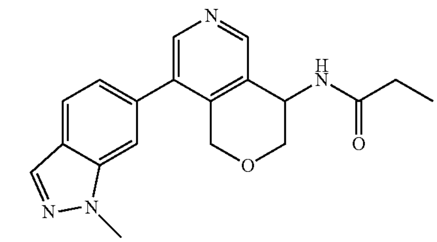 [SMILES: CCC(=O)NC1COCc2c(-c3ccc4cnn(C)c4c3)cncc21] | N-[8-(1-Methyl-1H-indazol-6-yl)-3,4-dihydro-1H-pyrano[4,3-c]pyridin-4-yl]-propionamide, Enantiomer I |
| 156 | 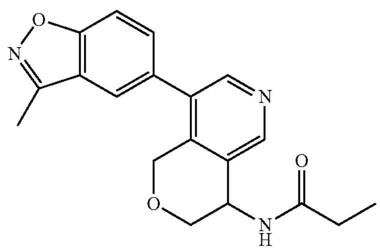 [SMILES: CCC(=O)NC1COCc2c(-c3ccc4onc(C)c4c3)cncc21] | N-[8-(3-Methyl-benzo[d]isoxazol-5-yl)-3,4-dihydro-1H-pyrano[4,3-c]pyridin-4-yl]-propionamide, Enantiomer I |
| 157 | 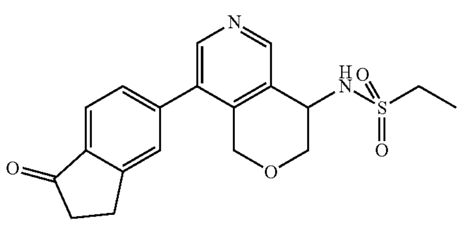 [SMILES: CCS(=O)(=O)NC1COCc2c(-c3ccc4c(c3)CCC4=O)cncc21] | Ethanesulfonic acid [8-(1-oxo-indan-5-yl)-3,4-dihydro-1H-pyrano[4,3-c]pyridin-4-yl]-amide, Enantiomer II |
| 158 | 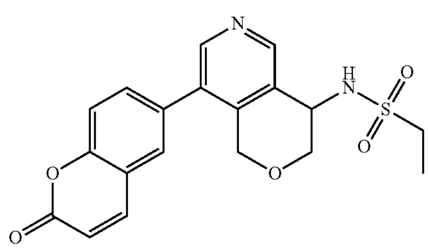 [SMILES: CCS(=O)(=O)NC1COCc2c(-c3ccc4oc(=O)ccc4c3)cncc21] | Ethanesulfonic acid [8-(2-oxo-2H-chromen-6-yl)-3,4-dihydro-1H-pyrano[4,3-c]pyridin-4-yl]-amide, Enantiomer II |
| 159 | 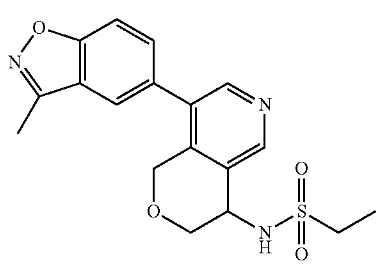 [SMILES: CCS(=O)(=O)NC1COCc2c(-c3ccc4onc(C)c4c3)cncc21] | Ethanesulfonic acid [8-(3-methyl-benzo[d]isoxazol-5-yl)-3,4-dihydro-1H-pyrano[4,3-c]pyridin-4-yl]-amide, Enantiomer I |
| 160 | 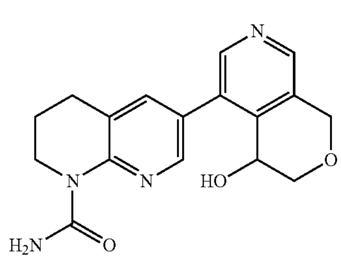 | 6-(4-Hydroxy-3,4-dihydro-1H-pyrano[3,4-c]pyridin-5-yl)-3,4-dihydro-2H-[1,8]naphthyridine-1-carboxylic acid amide |

TABLE 1-continued

| Cpd No | STRUCTURE | Name |
|---|---|---|
| 161 | 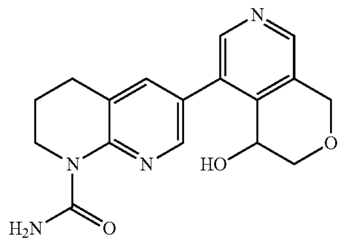 [SMILES: NC(=O)N1CCCc2cc(-c3cncc4c3C(O)COC4)cnc21] | 6-(4-Hydroxy-3,4-dihydro-1H-pyrano[3,4-c]pyridin-5-yl)-3,4-dihydro-2H-[1,8]naphthyridine-1-carboxylic acid amide, Enantiomer I |
| 162 | 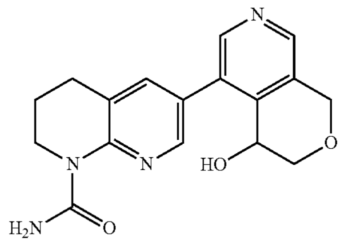 [SMILES: NC(=O)N1CCCc2cc(-c3cncc4c3C(O)COC4)cnc21] | 6-(4-Hydroxy-3,4-dihydro-1H-pyrano[3,4-c]pyridin-5-yl)-3,4-dihydro-2H-[1,8]naphthyridine-1-carboxylic acid amide, Enantiomer II |
| 163 | 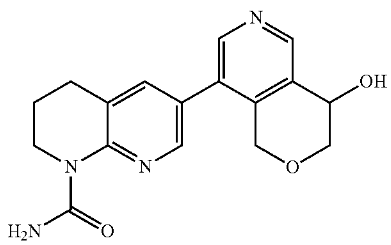 | 6-(4-Hydroxy-3,4-dihydro-1H-pyrano[4,3-c]pyridin-8-yl)-3,4-dihydro-2H-[1,8]naphthyridine-1-carboxylic acid amide, Enantiomer I |
| 164 | 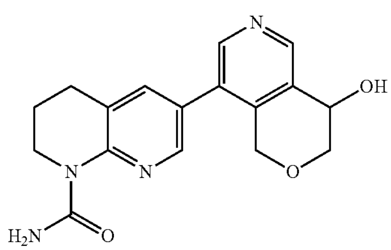 [SMILES: NC(=O)N1CCCc2cc(-c3cncc4c3COCC4O)cnc21] | 6-(4-Hydroxy-3,4-dihydro-1H-pyrano[4,3-c]pyridin-8-yl)-3,4-dihydro-2H-[1,8]naphthyridine-1-carboxylic acid amide, Enantiomer II |
| 165 | 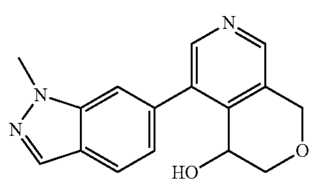 [SMILES: Cn1ncc2ccc(-c3cncc4c3C(O)COC4)cc21] | 5-(1-Methyl-1H-indazol-6-yl)-3,4-dihydro-1H-pyrano[3,4-c]pyridin-4-ol, Enantiomer II |
| 166 | 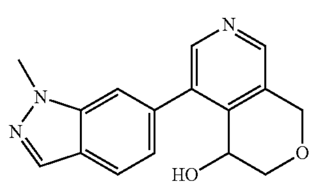 [SMILES: Cn1ncc2ccc(-c3cncc4c3C(O)COC4)cc21] | 5-(1-Methyl-1H-indazol-6-yl)-3,4-dihydro-1H-pyrano[3,4-c]pyridin-4-ol, Enantiomer I |
| 167 | 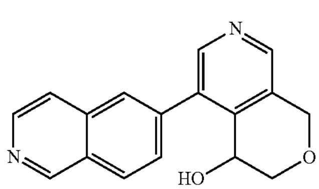 [SMILES: OC1COCc2cncc(-c3ccc4cnccc4c3)c21] | 5-Isoquinolin-6-yl-3,4-dihydro-1H-pyrano[3,4-c]pyridin-4-ol, Enantiomer II |

TABLE 1-continued

| Cpd No | STRUCTURE | Name |
|---|---|---|
| 168 | 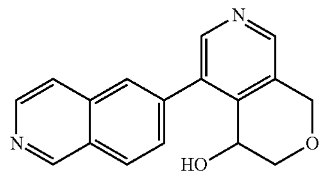 [SMILES: OC1COCc2cncc(-c3ccc4cnccc4c3)c21] | 5-Isoquinolin-6-yl-3,4-dihydro-1H-pyrano[3,4-c]pyridin-4-ol, Enantiomer I |
| 169 | 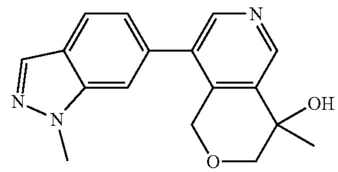 [SMILES: Cn1ncc2ccc(-c3cncc4c3COCC4(C)O)cc21] | 4-Methyl-8-(1-methyl-1H-indazol-6-yl)-3,4-dihydro-1H-pyrano[4,3-c]pyridin-4-ol, Enantiomer II |
| 170 | 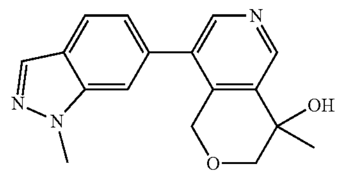 [SMILES: Cn1ncc2ccc(-c3cncc4c3COCC4(C)O)cc21] | 4-Methyl-8-(1-methyl-1H-indazol-6-yl)-3,4-dihydro-1H-pyrano[4,3-c]pyridin-4-ol, Enantiomer I |
| 171 | 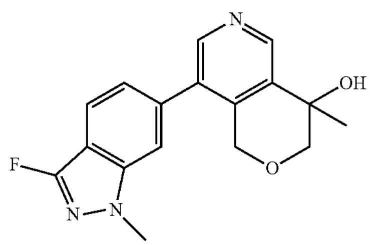 [SMILES: Cn1nc(F)c2ccc(-c3cncc4c3COCC4(C)O)cc21] | 8-(3-Fluoro-1-methyl-1H-indazol-6-yl)-4-methyl-3,4-dihydro-1H-pyrano[4,3-c]pyridin-4-ol, Enantiomer I |
| 172 | 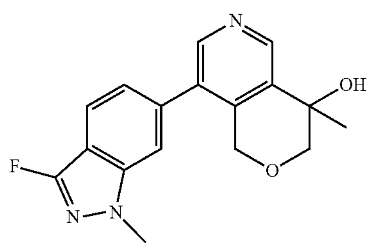 [SMILES: Cn1nc(F)c2ccc(-c3cncc4c3COCC4(C)O)cc21] | 8-(3-Fluoro-1-methyl-1H-indazol-6-yl)-4-methyl-3,4-dihydro-1H-pyrano[4,3-c]pyridin-4-ol, Enantiomer II |
| 173 | 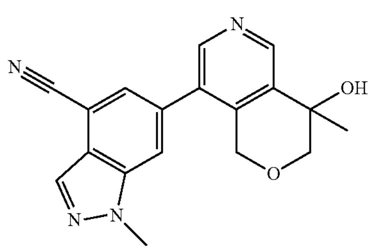 [SMILES: Cn1ncc2c(C#N)cc(-c3cncc4c3COCC4(C)O)cc21] | 6-(4-Hydroxy-4-methyl-3,4-dihydro-1H-pyrano[4,3-c]pyridin-8-yl)-1-methyl-1H-indazole-4-carbonitrile, Enantiomer I |
| 174 | 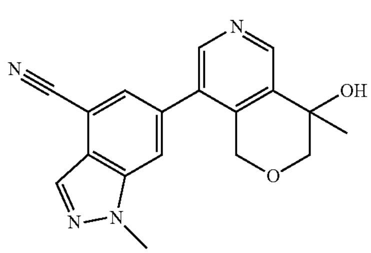 [SMILES: Cn1ncc2c(C#N)cc(-c3cncc4c3COCC4(C)O)cc21] | 6-(4-Hydroxy-4-methyl-3,4-dihydro-1H-pyrano[4,3-c]pyridin-8-yl)-1-methyl-1H-indazole-4-carbonitrile, Enantiomer II |

TABLE 1-continued

| Cpd No | STRUCTURE | Name |
|---|---|---|
| 175 | 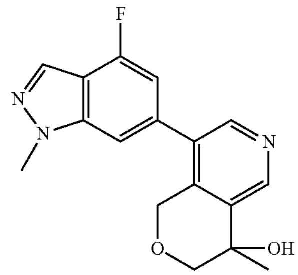 [SMILES: Cn1ncc2c(F)cc(-c3cncc4c3COCC4(C)O)cc21] | 8-(4-Fluoro-1-methyl-1H-indazol-6-yl)-4-methyl-3,4-dihydro-1H-pyrano[4,3-c]pyridin-4-ol, Enantiomer II |
| 176 | 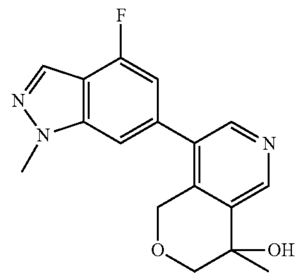 [SMILES: Cn1ncc2c(F)cc(-c3cncc4c3COCC4(C)O)cc21] | 8-(4-Fluoro-1-methyl-1H-indazol-6-yl)-4-methyl-3,4-dihydro-1H-pyrano[4,3-c]pyridin-4-ol, Enantiomer I |
| 177 | 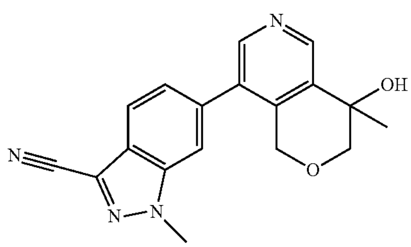 [SMILES: Cn1nc(C#N)c2ccc(-c3cncc4c3COCC4(C)O)cc21] | 6-(4-Hydroxy-4-methyl-3,4-dihydro-1H-pyrano[4,3-c]pyridin-8-yl)-1-methyl-1H-indazole-3-carbonitrile, Enantiomer I |
| 178 | 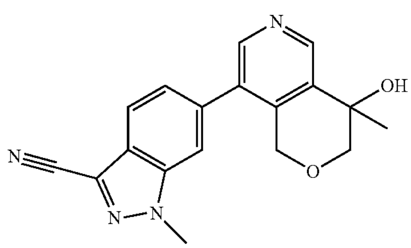 [SMILES: Cn1nc(C#N)c2ccc(-c3cncc4c3COCC4(C)O)cc21] | 6-(4-Hydroxy-4-methyl-3,4-dihydro-1H-pyrano[4,3-c]pyridin-8-yl)-1-methyl-1H-indazole-3-carbonitrile, Enantiomer II |
| 179 | 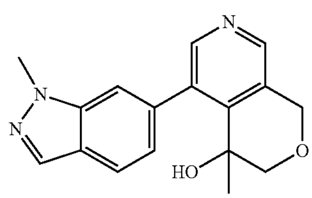 [SMILES: Cn1ncc2ccc(-c3cncc4c3C(C)(O)COC4)cc21] | 4-Methyl-5-(1-methyl-1H-indazol-6-yl)-3,4-dihydro-1H-pyrano[3,4-c]pyridin-4-ol, Enantiomer II |
| 180 | 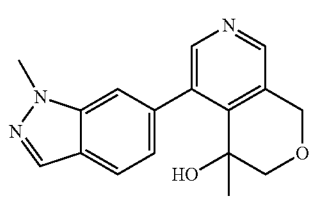 [SMILES: Cn1ncc2ccc(-c3cncc4c3C(C)(O)COC4)cc21] | 4-Methyl-5-(1-methyl-1H-indazol-6-yl)-3,4-dihydro-1H-pyrano[3,4-c]pyridin-4-ol, Enantiomer I |

TABLE 1-continued

| Cpd No | STRUCTURE | Name |
|---|---|---|
| 181 | 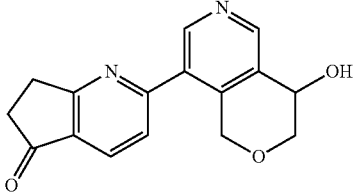 [SMILES: O=C1CCc2nc(-c3cncc4c3COCC4O)ccc21] | 2-(4-Hydroxy-3,4-dihydro-1H-pyrano[4,3-c]pyridin-8-yl)-6,7-dihydro-[1]pyrindin-5-one, Enantiomer I |
| 182 | 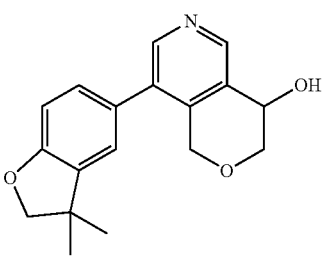 [SMILES: CC1(C)COc2ccc(-c3cncc4c3COCC4O)cc21] | 8-(3,3-Dimethyl-2,3-dihydro-benzofuran-5-yl)-3,4-dihydro-1H-pyrano[4,3-c]pyridin-4-ol, Enantiomer I |
| 183 | 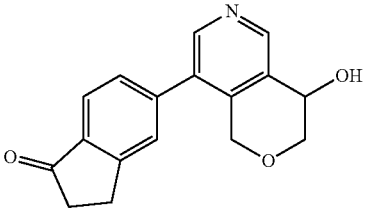 [SMILES: O=C1CCc2cc(-c3cncc4c3COCC4O)ccc21] | 5-(4-Hydroxy-3,4-dihydro-1H-pyrano[4,3-c]pyridin-8-yl)-indan-1-one, Enantiomer I |
| 184 | 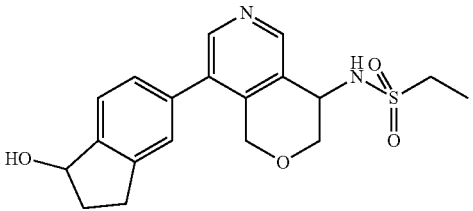 [SMILES: CCS(=O)(=O)NC1COCc2c(-c3ccc4c(c3)CCC4O)cncc21] | Ethanesulfonic acid [8-(1-hydroxy-indan-5-yl)-3,4-dihydro-1H-pyrano[4,3-c]pyridin-4-yl]-amide, mixture of diastereomers |
| 185 | 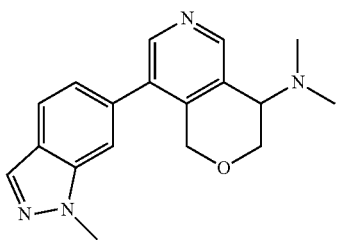 [SMILES: CN(C)C1COCc2c(-c3ccc4cnn(C)c4c3)cncc21] | Dimethyl-[8-(1-methyl-1H-indazol-6-yl)-3,4-dihydro-1H-pyrano[4,3-c]pyridin-4-yl]-amine, Enantiomer II |
| 186 | 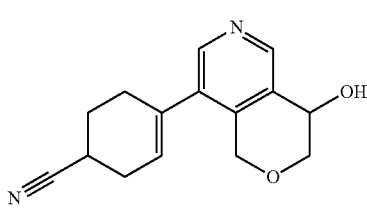 | 4-(4-Hydroxy-3,4-dihydro-1H-pyrano[4,3-c]pyridin-8-yl)-cyclohex-3-enecarbonitrile, Enantiomer I |

TABLE 1-continued

| Cpd No | STRUCTURE | Name |
|---|---|---|
| 187 | 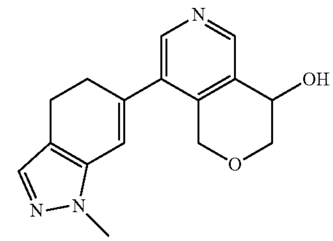 [SMILES: Cn1ncc2c1C=C(c1cncc3c1COCC3O)CC2] | 8-(1-Methyl-4,5-dihydro-1H-indazol-6-yl)-3,4-dihydro-1H-pyrano[4,3-c]pyridin-4-ol, Enantiomer II |
| 188 | 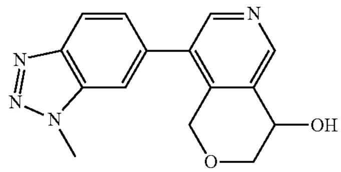 [SMILES: Cn1nnc2ccc(-c3cncc4c3COCC4O)cc21] | 8-(3-Methyl-3H-benzotriazol-5-yl)-3,4-dihydro-1H-pyrano[4,3-c]pyridin-4-ol, Enantiomer I |
| 189 | 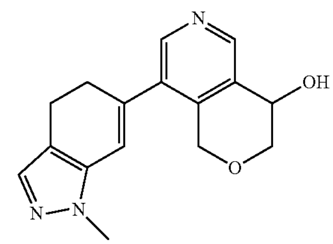 [SMILES: Cn1ncc2c1C=C(c1cncc3c1COCC3O)CC2] | 8-(1-Methyl-4,5-dihydro-1H-indazol-6-yl)-3,4-dihydro-1H-pyrano[4,3-c]pyridin-4-ol, Enantiomer I |
| 190 | 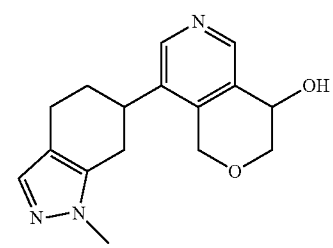 [SMILES: Cn1ncc2c1CC(c1cncc3c1COCC3O)CC2] | 8-(1-Methyl-4,5,6,7-tetrahydro-1H-indazol-6-yl)-3,4-dihydro-1H-pyrano[4,3-c]pyridin-4-ol, Diastereomer I |
| 191 | 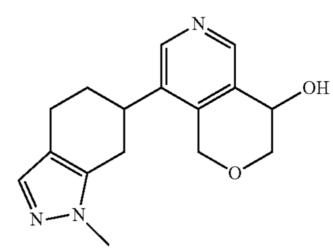 [SMILES: Cn1ncc2c1CC(c1cncc3c1COCC3O)CC2] | 8-(1-Methyl-4,5,6,7-tetrahydro-1H-indazol-6-yl)-3,4-dihydro-1H-pyrano[4,3-c]pyridin-4-ol, Diastereomer II |
| 192 | 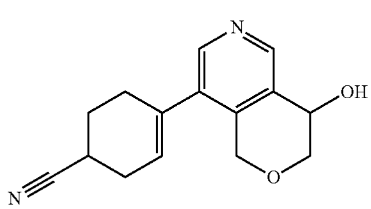 [SMILES: N#CC1CC=C(c2cncc3c2COCC3O)CC1] | 4-(4-Hydroxy-3,4-dihydro-1H-pyrano[4,3-c]pyridin-8-yl)-cyclohex-3-enecarbonitrile, Enantiomer II |

TABLE 1-continued

| Cpd No | STRUCTURE | Name |
|---|---|---|
| 193 | 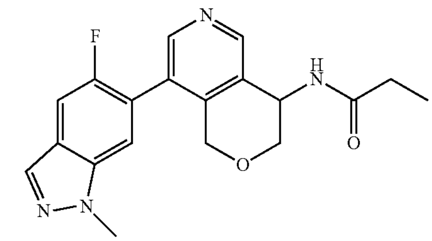 [SMILES: CCC(=O)NC1COCc2c(-c3cc4c(cnn4C)cc3F)cncc21] | N-[8-(5-Fluoro-1-methyl-1H-indazol-6-yl)-3,4-dihydro-1H-pyrano[4,3-c]pyridin-4-yl]-propionamide, Enantiomer II |
| 194 | 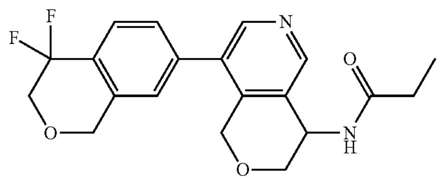 [SMILES: CCC(=O)NC1COCc2c(-c3ccc4c(c3)COCC4(F)F)cncc21] | N-[8-(4,4-Difluoro-isochroman-7-yl)-3,4-dihydro-1H-pyrano[4,3-c]pyridin-4-yl]-propionamide, Enantiomer II |
| 195 | 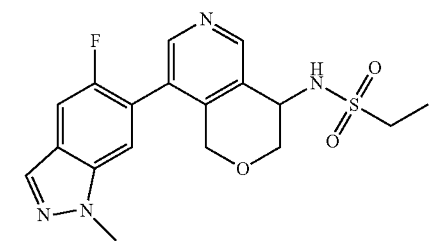 [SMILES: CCS(=O)(=O)NC1COCc2c(-c3cc4c(cnn4C)cc3F)cncc21] | Ethanesulfonic acid [8-(5-fluoro-1-methyl-1H-indazol-6-yl)-3,4-dihydro-1H-pyrano[4,3-c]pyridin-4-yl]-amide, Enantiomer II |
| 196 | 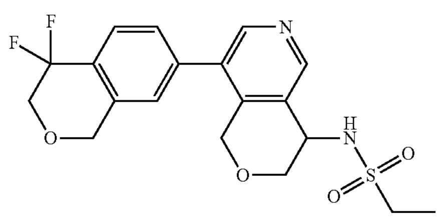 [SMILES: CCS(=O)(=O)NC1COCc2c(-c3ccc4c(c3)COCC4(F)F)cncc21] | Ethanesulfonic acid [8-(4,4-difluoro-isochroman-7-yl)-3,4-dihydro-1H-pyrano[4,3-c]pyridin-4-yl]-amide, Enantiomer II |
| 197 | 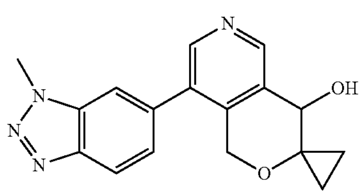 [SMILES: Cn1nnc2ccc(-c3cncc4c3COC3(CC3)C4O)cc21] | 8-(3-methylbenzotriazol-5-yl)spiro[1,4-dihydropyrano[4,3-c]pyridine-3,1'-cyclopropane]-4-ol, Enantiomer I |
| 198 | 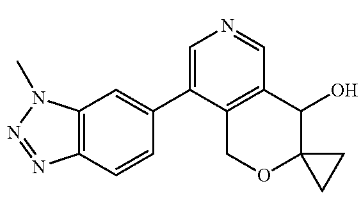 [SMILES: Cn1nnc2ccc(-c3cncc4c3COC3(CC3)C4O)cc21] | 8-(3-methylbenzotriazol-5-yl)spiro[1,4-dihydropyrano[4,3-c]pyridine-3,1'-cyclopropane]-4-ol, Enantiomer II |
| 199 | 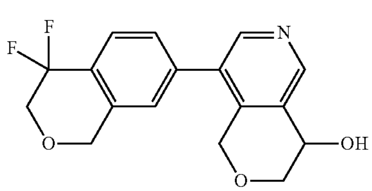 [SMILES: OC1COCc2c(-c3ccc4c(c3)COCC4(F)F)cncc21] | 8-(4,4-Difluoro-isochroman-7-yl)-3,4-dihydro-1H-pyrano[4,3-c]pyridin-4-ol, Enantiomer II |

TABLE 1-continued

| Cpd No | STRUCTURE | Name |
|---|---|---|
| 200 | 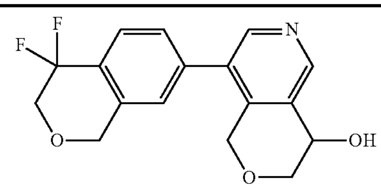 | 8-(4,4-Difluoro-isochroman-7-yl)-3,4-dihydro-1H-pyrano[4,3-c]pyridin-4-ol, Enantiomer I |

In one embodiment, the invention relates to a compound selected from the group consisting of compounds 1-200 depicted in Table 1 above and the pharmaceutically acceptable salts thereof.

In another embodiment, the invention relates to compounds 1, 4-7, 9, 12-18, 22, 29, 30, 33-38, 43-45, 47-49, 51, 52, 55, 56, 60, 61, 65, 68, 69, 71, 73-77, 81, 83, 85, 89, 90, 92, 94, 96, 102-105, 107, 110, 112-114, 116, 118, 121, 123, 125-129, 131-133, 136, 142, 143, 148-150, 152-154, 157, 158, 160-164, 166, 168-172, 175-179, 183, 185-199 depicted in Table 1 above and the pharmaceutically acceptable salts thereof.

In another embodiment, the invention relates to compounds 9, 12-18, 29, 34, 36-38, 43-45, 47, 48, 55, 60, 61, 65, 68, 69, 71, 73-77, 81, 83, 85, 89, 90, 92, 94, 96, 102-105, 107, 110, 112-114, 116, 118, 121, 123, 125-129, 131-133, 136, 142, 143, 148-150, 152-154, 157, 158, 160-164, 166, 168-172, 175-179, 183 and 185-199 depicted in Table 1 above and the pharmaceutically acceptable salts thereof.

In another embodiment, the invention relates to compounds 1-159, 163, 164, 169-178, and 181-199.

In another embodiment, the invention relates to compounds 160-162, 165-168 and 179-180.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates, esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, peroxides or a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $—(CH_2)—$, $—(CH_2—CH_2)—$, $—(CH(CH_3))—$, $—(CH_2—CH_2—CH_2)—$, $—(C(CH_3)_2)—$, $—(CH(CH_2CH_3))—$, $—(CH(CH_3)—CH_2)—$, $—(CH_2—CH(CH_3))—$, $—(CH_2—CH_2—CH_2—CH_2)—$, $—(CH_2—CH_2—CH(CH_3))—$, $—(CH(CH_3)—CH_2—CH_2)—$, $—(CH_2—CH(CH_3)—CH_2)—$, $—(CH_2—C(CH_3)_2)—$, $—(C(CH_3)_2—CH_2)—$, $—(CH(CH_3)—CH(CH_3))—$, $—(CH_2—CH(CH_2CH_3))—$, $—(CH(CH_2CH_3)—CH_2)—$, $—(CH(CH_2CH_2CH_3))—$, $—(CHCH(CH_3)_2)—$ and $—C(CH_3)(CH_2CH_3)—$.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be $—CH_2CHF_2$, $—CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—$R_a$ may be represented as phenyl-S(O)$_m$— when $R_a$ is phenyl and where m is 0, 1 or 2.

General Synthetic Methods and Synthesis of Intermediates

The compounds of the invention may be prepared by the methods and examples presented below and methods known to those of ordinary skill in the art. The methods that are described here are intended as an illustration and for the enablement of the instant invention without restricting the scope of its subject matter, the claimed compounds, and the examples. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC, supercritical fluid chromatography (SFC), and recrystallization.

Intermediate A1: Synthesis of
8-bromo-1H-pyrano[4,3-c]pyridin-4-one

A solution of 3,5-dibromo-pyridine-4-carbaldehyde (300 g, 1.1 mol) in methanol (1.5 L) is cooled down to 0° C. and sodium borohydride (64 g, 1.7 mol) is added. Then the reaction mixture is stirred for 2 hr before ice is added. The solvent is removed and the mixture is extracted with DCM (3×500 mL). The organic layers are combined, dried over Na$_2$SO$_4$ and concentrated to give 280 g of (3,5-dibromo-pyridin-4-yl)-methanol.

A solution of (3,5-dibromo-pyridin-4-yl)-methanol (280 g, 1.0 mol) in THF (1.2 L) is cooled down to 0° C. and 60% NaH in mineral oil (100 g, 2.5 mol) is added. The reaction mixture is stirred for 30 min and allyl bromide (250 g, 2.1 mol) is added. The reaction mixture is warmed up to room temperature for 12 hr before ice is added. The mixture is extracted with EtOAc (2×800 mL) and the organic layers are combined and concentrated to give the crude product. Purification by flash silica column chromatography affords 250 g of 4-allyloxymethyl-3,5-dibromo-pyridine.

To a stirred solution of the 4-allyloxymethyl-3,5-dibromo-pyridine (100 g, 330 mmol) in acetonitrile (600 mL) in a sealed tube are added palladium acetate (22 g, 97 mmol), triethyl amine (33 g, 330 mmol) and triphenylphosphine (26 g, 97 mmol). The tube is sealed and heated at 100° C. for 2 hr. Water is added and the mixture is extracted with EtOAc. The organic layers are combined, dried over Na$_2$SO$_4$ and concentrated to give the crude product. Purification by flash silica column chromatography affords 55 g of 8-bromo-4-methylene-3,4-dihydro-1H-pyrano[4,3-c]pyridine.

To a stirred solution of 8-bromo-4-methylene-3,4-dihydro-1H-pyrano[4,3-c]pyridine (20 g, 88 mmol) in THF (200 mL) and water (200 mL) are added osmium tetraoxide (4.5 g, 18 mmol) and sodium periodate (41 g, 190 mmol). The reaction mixture is heated at 70° C. for 2 hr. After it is cooled down to room temperature, the reaction mixture is filtered through diatomaceous earth and the filtrate is extracted with EtOAc. The combined organic layers are dried over anhydrous Na$_2$SO$_4$ and concentrated to give the crude product. Purification by flash silica column chromatography affords 13 g of the title product.

Intermediate A2, A3 and A4: Syntheses of
8-bromo-3,4-dihydro-1H-pyrano[4,3-c]pyridin-4-ol
and its Enantiomers

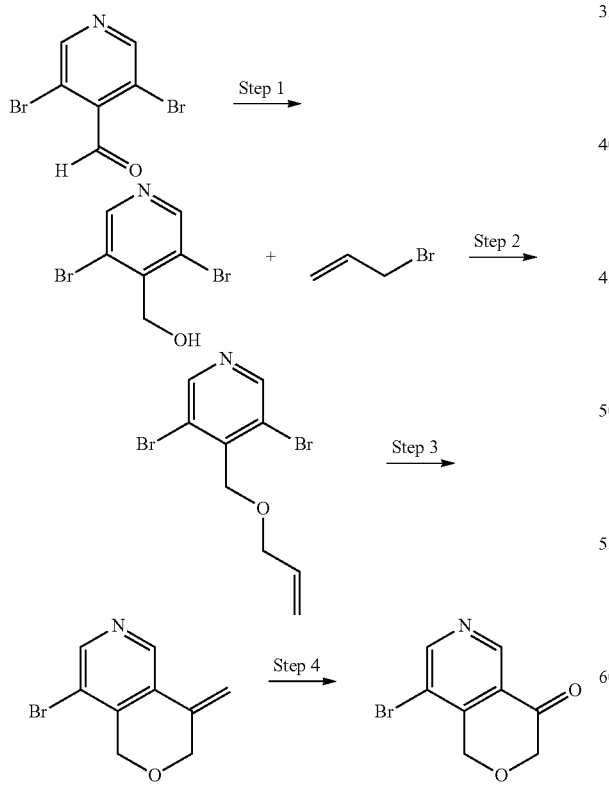

Intermediate A1

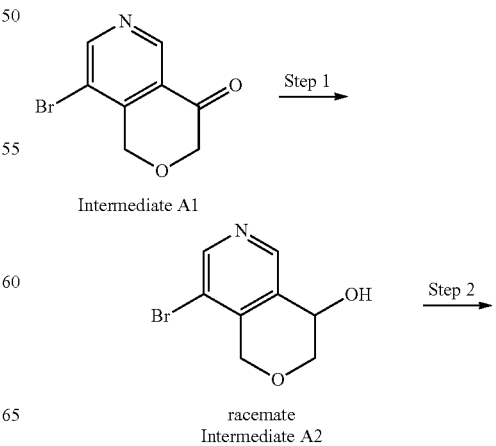

racemate
Intermediate A2

-continued

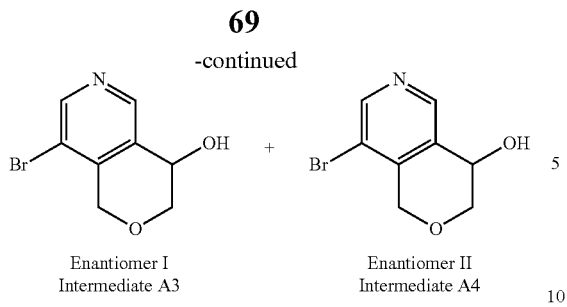

Enantiomer I
Intermediate A3

Enantiomer II
Intermediate A4

Intermediate A1 (10 g, 44 mmol) is dissolved in MeOH (200 mL) and sodium borohydride (5.0 g, 130 mmol) is added. The reaction mixture is stirred at room temperature for 1 hr and the solvent is removed. The residue is diluted with EtOAc (200 mL), washed with water (2×100 mL) and brine (1×100 mL). The organic layer is separated, dried over anhydrous Na$_2$SO$_4$ and concentrated to give 10 g of racemic 8-bromo-3,4-dihydro-1H-pyrano[4,3-c]pyridin-4-ol (Intermediate A2).

Chiral separation of the racemic Intermediate A2 (10 g, 44 mmol) using Supercritical Fluid Chromatography affords 4.0 g of Enantiomer I (Intermediate A3, 3.26 min) and 4.1 g of Enantiomer II (Intermediate A4, 4.34 min). The retention times are measured using the following conditions: Regis RegisPack analytical Column, Mobile phase 10% (1:1:1 MeOH:EtOH:iPA):CO$_2$ @ 3 mL/min, 200 bar, 40° C.

Intermediate A5: Synthesis of 8-bromo-4-methyl-3,4-dihydro-1H-pyrano[4,3-c]pyridin-4-ol

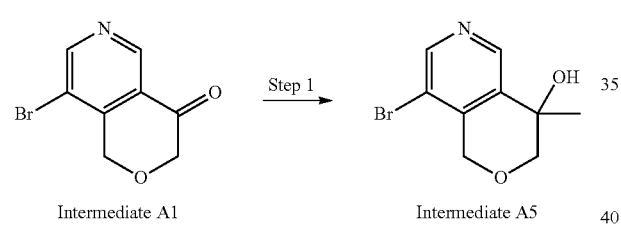

Intermediate A1

Intermediate A5

Intermediate A1 (2.0 g, 8.8 mmol) is dissolved in THF (80 mL) and 3.0 M methyl magnesium bromide ether solution (5.9 mL, 18 mmol) is added. The mixture is stirred for 1 hr before another 1 mL of methyl magnesium bromide ether solution is added. The reaction is stirred for another 30 min and saturated aqueous NH$_4$Cl solution (15 mL) is added along with water (15 mL) and EtOAc (100 mL). The mixture is stirred for 10 min and the aqueous layer is separated and extracted with EtOAc. The organic layers are combined and concentrated to give the crude product. Purification by flash column chromatography affords 1.2 g of the title product.

Intermediate A6: Synthesis of 8-bromo-3,4-dihydro-1H-pyrano[4,3-c]pyridine-4-carbonitrile

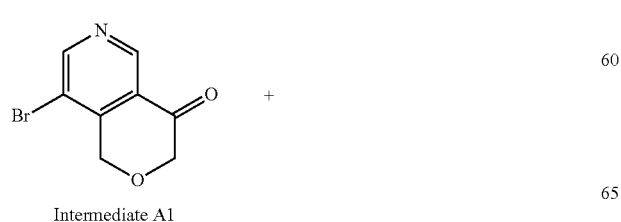

Intermediate A1

-continued

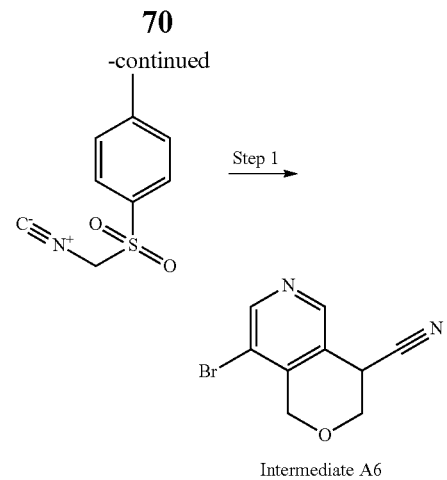

Intermediate A6

Intermediate A1 (7.0 g, 31 mmol) is dissolved in DCM (100 mL), then potassium tert-butoxide (4.1 g, 37 mmol) and 1-isocyanomethanesulfonyl-4-methyl-benzene (6.6 g, 34 mmol) are added at 0° C. The reaction mixture is stirred for 2 hr and it is quenched with ice water. The mixture is extracted with DCM and all the organic layers are combined and concentrated to give the crude product. Purification by flash column chromatography affords 300 mg of the title product.

Intermediate A7 and A8: Syntheses of 8-bromo-spiro[1,4-dihydropyrano[4,3-c]pyridine-3,1'-cyclopropane]-4-ol and its Enantiomers

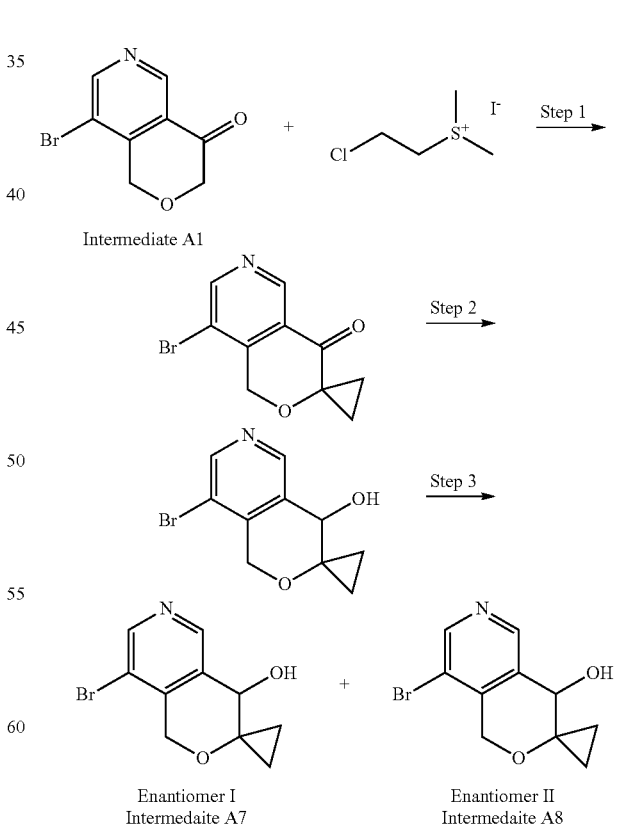

Intermediate A1

Enantiomer I
Intermedaite A7

Enantiomer II
Intermedaite A8

To a stirred solution of methyl 2-chloroethyl sulfide (9.7 g, 88 mmol) in acetonitrile (300 mL) is added methyl iodide (12 g, 88 mmol) at 0° C. and the mixture is warmed to room temperature for 16 hr. Then the mixture is concentrated and the residue is washed with mixture of methanol and diethyl ether (1:3). A solid is formed and it is collected by filtration. The solid is mixed with. Intermediate A1 (10 g, 44 mmol) in tert-butanol (200 mL) and potassium tert-butoxide (9.8 g, 88 mmol) is added. The reaction mixture is heated at 70° C. for 2 hr and then water is added to quench the reaction. The mixture is extracted with EtOAc and the organic layers are combined and concentrated to give the crude product. Purification by flash silica column chromatography affords 3.5 g of 8-bromospiro[1H-pyrano[4,3-c]pyridine-3,1'-cyclopropane]-4-one.

To a stirred solution of 8-bromospiro[1H-pyrano[4,3-c]pyridine-3,1'-cyclopropane]-4-one (3.5 g, 14 mmol) in methanol (70 mL) cooled at 0° C. is added sodium borohydride (0.51 g, 14 mmol) batch wise. The reaction mixture is warmed up to room temperature for 1 hr before the solvent is removed. Ice is added to the residue and the mixture is extracted with EtOAc. The organic layers are combined and concentrated to give the crude product. Purification by flash column chromatography affords 2.7 g of racemic 8-bromo-spiro[1,4-dihydropyrano[4,3-c]pyridine-3,1'-cyclopropane]-4-ol.

Chiral separation of the racemic 8-bromospiro[1,4-dihydropyrano[4,3-c]pyridine-3,1'-cyclopropane]-4-ol (2.7 g, 11 mmol) using Supercritical Fluid Chromatography affords 1.0 g of Enantiomer I (Intermediate A7, 2.43 min) and 1.1 g of Enantiomer II (Intermediate A8, 3.32 min). The retention times are measured using the following conditions: LUX Cellulose-2, 4.6×100 mm Column, Mobile phase 15% (1:1:1 MeOH:EtOH:iPA):CO₂ @ 3 mL/min, 200 bar, 40° C.

Intermediate A9 and A10: Syntheses of (8-bromo-3,4-dihydro-1H-pyrano[4,3-c]pyridin-4-yl)-carbamic Acid Tert-Butyl Ester and its Enantiomers

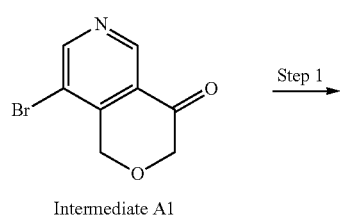

Intermediate A1

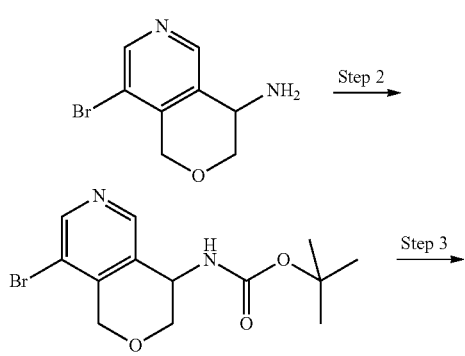

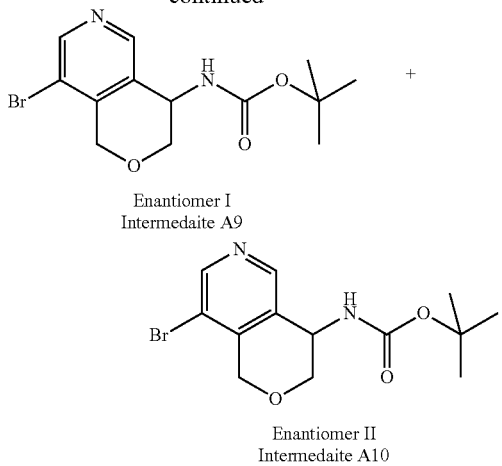

Enantiomer I
Intermedaite A9

Enantiomer II
Intermedaite A10

Intermediate A1 (3.0 g, 13 mmol) and titanium isopropoxide (8.6 mL, 29 mmol) are mixed in 2.0 M ammonia ethanol solution (99 mL, 196 mmol). The mixture is stirred at room temperature for 16 hr, then sodium borohydride (1.0 g, 26 mmol) is added. The reaction is continued for another 3 hr and the solvent is removed to give the crude 8-bromo-3,4-dihydro-1H-pyrano[4,3-c]pyridin-4-ylamine which is used in the next step without purification.

The crude 8-bromo-3,4-dihydro-1H-pyrano[4,3-c]pyridin-4-ylamine (3.0 g, 13 mmol) is dissolved in THF (90 mL) and di-tert-butyl dicarbonate (14 g, 62 mmol) is added. The mixture is stirred for 40 hr and saturated aqueous NH₄Cl solution (10 mL) is added. After stirring the mixture for 10 min, saturated aqueous NaHCO₃ solution (20 mL) is added. The mixture is again stirred for 10 min and a solid is formed. The solid is filtered and the filtrate is extracted with EtOAc (3×150 mL). The organic layers are combined and concentrated to give the crude product. Purification by flash column chromatography affords 2.8 g of the title product (racemate).

Chiral separation of the racemic (8-bromo-3,4-dihydro-1H-pyrano[4,3-c]pyridin-4-yl)-carbamic acid tert-butyl ester (2.8 g, 8.4 mmol) using Supercritical Fluid Chromatography affords 1.2 g of Enantiomer I (Intermediate A9, 1.61 min) and 1.2 g of Enantiomer II (Intermediate A10, 2.50 min). The retention times are measured using the following conditions: RegisPack analytical Column, Mobile phase 10% (1:1:1 MeOH:EtOH:iPA):CO₂ @ 3 mL/min, 200 bar, 40° C.

Intermediate A11: Synthesis of Enantiomerically Pure N-(8-bromo-3,4-dihydro-1H-pyrano[4,3-c]pyridin-4-yl)-propionamide

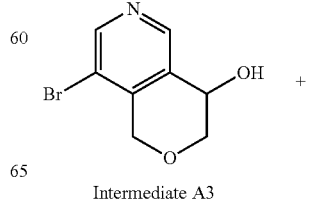

Intermediate A3

-continued

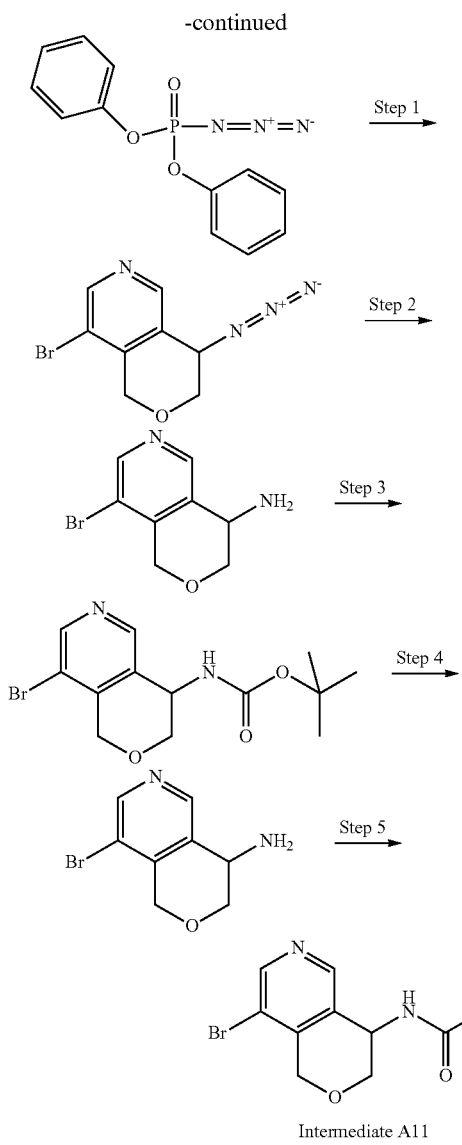

Intermediate A11

Enantiomerically pure Intermediate A3 (4.0 g, 17 mmol) and diphenylphosphoryl azide (4.9 mL, 23 mmol) are dissolved in THF (100 mL) and the reaction mixture is cooled down to 0° C. 1,8-Diazabicyclo[5.4.0]undec-7-ene (3.4 mL, 23 mmol) is added dropwise and the mixture is warmed to room temperature for 1 hr and heated at 45° C. for 3 hr. Then the reaction mixture is cooled down to room temperature and stirred for another 16 hr. The resulting mixture is used in the next step without workup or purification.

Triphenylphosphine (6.0 g, 23 mmol) is added into the reaction mixture obtained from the previous step and the mixture is heated at 60° C. for 2 hr. After it is cooled down to room temperature, water (24 mL) is added and the mixture is heated at 65° C. for 3 hr. After the mixture is cooled down to room temperature, it is used in the next step without workup or purification.

Di-tert-butyl dicarbonate (20 g, 92 mmol) is added into the reaction mixture obtained from the previous step and the resulting mixture is stirred for 16 hr. Then water (300 mL) is added along with 100 mL of EtOAc. The mixture is stirred for 5 min and the aqueous layer is separated and extracted with EtOAc (3×100 mL). All the organic layers are combined and concentrated to give the crude product. Purification by flash column chromatography affords 4.0 g of enantiomerically pure (8-bromo-3,4-dihydro-1H-pyrano[4,3-c]pyridin-4-yl)-carbamic acid tert-butyl ester.

Enantiomerically pure (8-bromo-3,4-dihydro-1H-pyrano[4,3-c]pyridin-4-yl)-carbamic acid tert-butyl ester (4.0 g, 12 mmol) is dissolved in DCM (120 mL) and trifluoroacetic acid (10 mL) is added. The mixture is stirred for 3 hr and saturated aqueous NaHCO₃ solution (20 mL) is added along with 10 mL of water. The mixture is stirred for 10 min and the aqueous layer is separated and extracted with DCM (3×75 mL) and EtOAc (6×75 mL). All the organic layers are combined and concentrated to give 2.8 g of the crude 8-bromo-3,4-dihydro-1H-pyrano[4,3-c]pyridin-4-ylamine which is used without purification.

8-Bromo-3,4-dihydro-1H-pyrano[4,3-c]pyridin-4-ylamine (1.4 g, 6.1 mmol), propionic acid (0.54 mL, 7.3 mmol) and triethyl amine (2.5 mL, 18 mmol) are mixed in acetonitrile (60 mL), then 0-(benzotriazol-1-yl)-N,N,N',N'-tetramethyluronium tetrafluoroborate (2.3 g, 7.3 mmol) is added. The mixture is stirred for 60 hr and all the solvents are removed. The residue is purified by flash column chromatography to give 1.5 g of the title product.

Intermediate A12: Synthesis of Enantiomerically Pure Ethanesulfonic Acid (8-bromo-3,4-dihydro-1H-pyrano[4,3-c]pyridin-4-yl)-amide

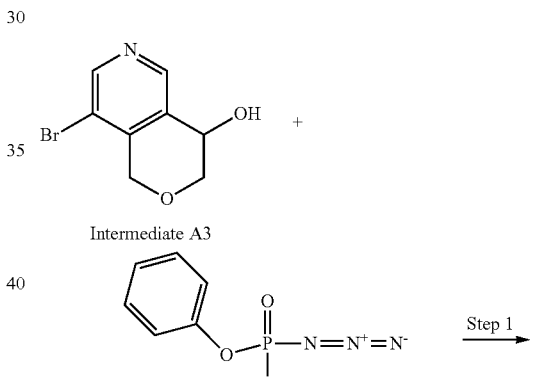

Intermediate A3

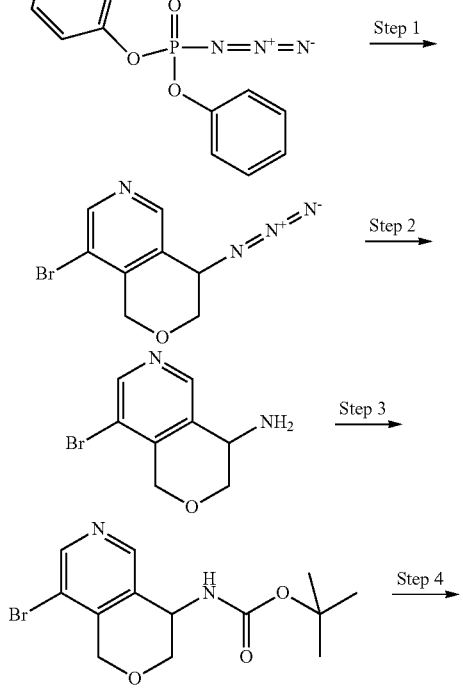

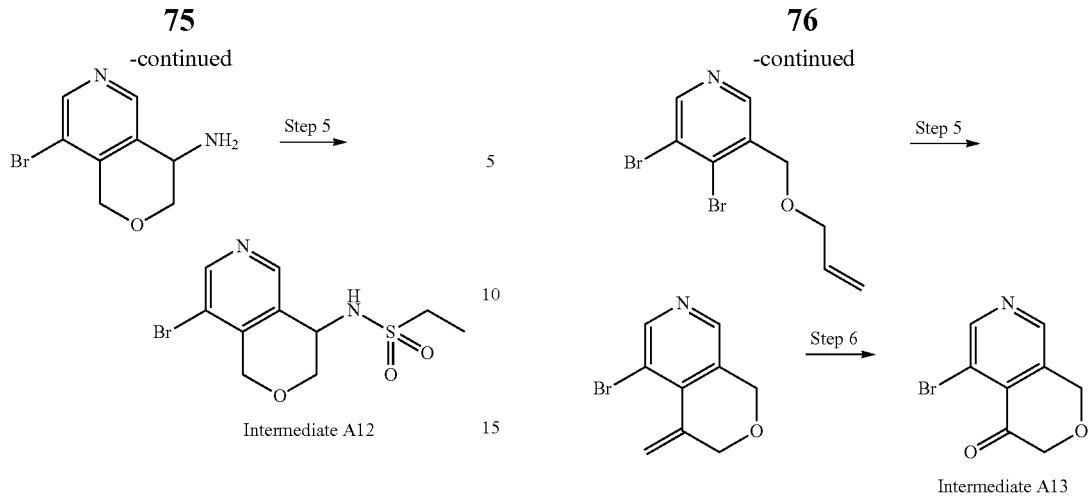

Procedures of Step 1 to Step 4 are described above for Intermediate A11. The crude 8-bromo-3,4-dihydro-1H-pyrano[4,3-c]pyridin-4-ylamine is obtained by following these procedures.

8-Bromo-3,4-dihydro-1H-pyrano[4,3-c]pyridin-4-ylamine (1.4 g, 6.1 mmol) is dissolved in DCM (60 mL) and triethyl amine (0.93 mL, 6.7 mmol) is added. Then ethanesulfonyl chloride (0.63 mL, 6.7 mmol) is added slowly and the mixture is stirred for 35 min. The saturated aqueous NaHCO$_3$ solution (15 mL) is added along with water (15 mL). The mixture is stirred for 10 min and the organic layer is separated. The aqueous layer is extracted with DCM (2×45 mL) and all organic layers are combined and concentrated to give the crude product. Purification by flash column chromatography affords 1.6 g of the title product.

Intermediate A13: Synthesis of
5-bromo-1H-pyrano[3,4-c]pyridin-4-one

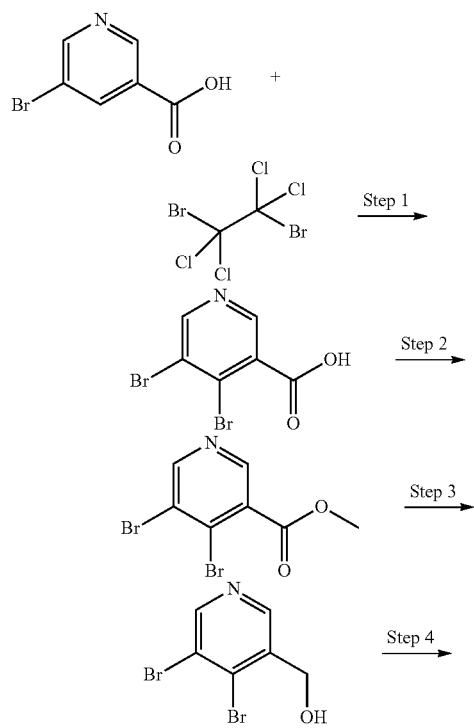

A stirred solution of 5-bromo nicotinic acid (30 g, 150 mmol) in dry THF (500 mL) is cooled down to −70° C. Freshly made lithium diisopropylamide (240 mmol, from 53 mL of diisopropylamine and 150 mL of 1.6 M n-BuLi in THF) is added dropwise and the mixture is stirred for 2.5 hr at −55° C. before it is cooled down to −70° C. 1,2-Dibromo-1,1,2,2-tetrachloro-ethane (50 g, 150 mmol) is added over 30 min and the mixture is stirred for 30 min before it is warmed to −20° C. over 2 hr. Then water (150 mL) is added and the pH of the reaction mixture is adjusted to 3 by adding concentrated HCl. A solid is formed and it is filtered, rinsed with pentane to give 25 g of 4,5-dibromo-nicotinic acid.

To a stirred solution of 4,5-dibromo-nicotinic acid (50 g, 180 mmol) in DMF (300 mL) is added potassium carbonate (49 g, 360 mmol) at 0° C. The mixture is stirred for 15 min and methyl iodide (38 g, 270 mmol) is added at 0° C. Then the reaction mixture is slowly warmed up to room temperature for 12 hr. Icy water is added and a solid is formed. The solid is filtered and dissolved in DCM. The solvent is removed to give the crude product. Purification by flash column chromatography affords 30 g of 4,5-dibromo-nicotinic acid methyl ester.

To a stirred solution of 4,5-dibromo-nicotinic acid methyl ester (30 g, 100 mmol) in methanol (300 mL) cooled at 0° C. is added sodium borohydride (11 g, 290 mmol). The reaction mixture is warmed to room temperature for 1 hr. The solvent is removed and ice is added. The mixture is extracted with EtOAc and the organic layers are combined, dried and concentrated to give 21 g of (4,5-dibromo-pyridin-3-yl)-methanol.

To a stirred solution of (4,5-dibromo-pyridin-3-yl)-methanol (21 g, 79 mmol) in THF (200 mL) cooled at 0° C. is added 60% sodium hydride (3.8 g, 160 mmol). The mixture is stirred for 30 min at 0° C. and allyl bromide (19 g, 160 mmol) is added. Then the reaction is warmed to room temperature for 12 hr. Ice is added and the mixture is extracted with EtOAc. The organic layers are separated, dried and concentrated to give the crude product. Purification by flash column chromatography affords 10 g of 3-allyloxymethyl-4,5-dibromo-pyridine.

To a stirred solution of 3-allyloxymethyl-4,5-dibromo-pyridine (8.0 g, 26 mmol) in acetonitrile 120 mL) are added triethyl amine (7.9 g, 78 mmol), triphenylphosphine (4.1 g, 16 mmol) and palladium acetate (2.3 g, 10 mmol). The mixture is heated at 100° C. for 2 hr before it is cooled down to room temperature. Water is added and the mixture is extracted with EtOAc. The organic layers are combined, dried and concentrated to give the crude product. Purification by flash column chromatography affords 1.2 g of 5-bromo-4-methylene-3,4-dihydro-1H-pyrano[3,4-c]pyridine.

To a stirred solution of 5-bromo-4-methylene-3,4-dihydro-1H-pyrano[3,4-c]pyridine (1.2 g, 5.3 mmol) in THF (20 mL) and water (20 mL) are added sodium periodate (2.5 g, 12 mmol) and osmium tetraoxide (270 mg, 1.1 mmol). The mixture is stirred at room temperature for 2 hr and then the solvent is removed. The residue is extracted with EtOAc and the organic layers are combined, dried and concentrated to give the crude product. Purification by flash column chromatography affords 260 mg of the title product.

Intermediate B1: Synthesis of 3-bromo-quinoline-8-carboxylic Acid Amide

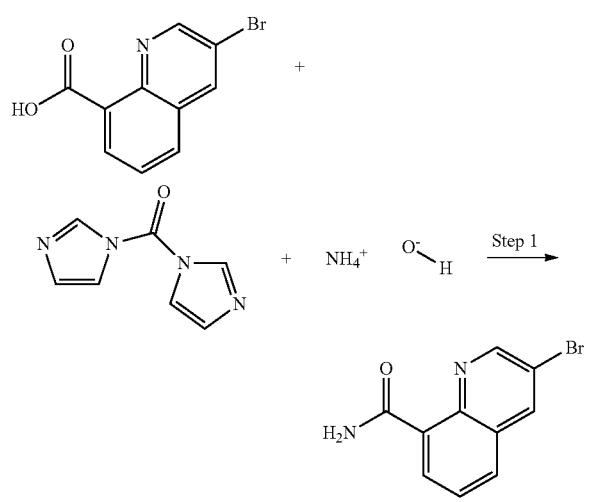

Intermediate B1

3-Bromo-quinoline-8-carboxylic acid (900 mg, 3.6 mmol) is dissolved in DMF (27 mL) and CDI (1.3 g, 7.9 mmol) is added. The mixture is heated at 60° C. for 16 hr before it is cooled down to room temperature. Then 28% ammonium hydroxide aqueous solution (4.5 g, 36 mmol) is added and the mixture is stirred for another 1 hr. The saturated NaHCO₃ aqueous solution (30 mL) is added along with water (30 mL). A white solid is formed and it is filtered, rinsed with more water and dried to give 650 mg of the title product.

Intermediate B2: Synthesis of 1-(5-bromo-1,3-dihydro-isoindol-2-yl)-ethanone

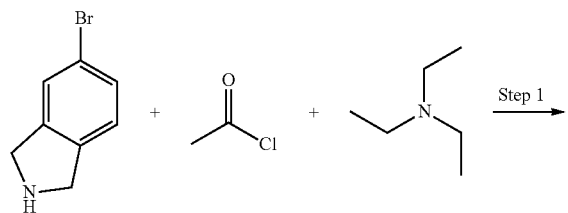

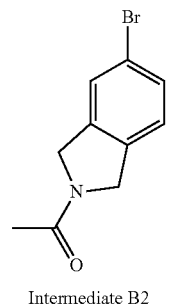

Intermediate B2

5-Bromo-2,3-dihydro-1H-isoindole (1.0 g, 5.0 mmol) is dissolved in DCM (50 mL) and acetyl chloride (7.6 mL, 7.6 mmol) and triethyl amine (1.4 mL, 10 mmol) are added. The mixture is stirred for 1 hr before saturated NaHCO₃ aqueous solution (30 mL) and water (30 mL) are added. The mixture is stirred for 10 min and the organic layer is separated. The aqueous layer is extracted with DCM (2×35 mL) and all the organic layers are combined and concentrated to give the crude product. Purification by flash column chromatography affords 850 mg of the title product.

Intermediate B3: Synthesis of 6-bromo-1-methyl-1H-indazole-3-carbonitrile

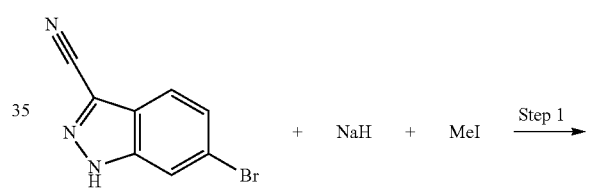

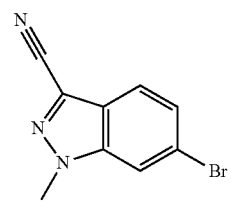

Intermediate B3

6-Bromo-1H-indazole-3-carbonitrile (500 mg, 2.3 mmol) is dissolved in THF (20 mL) and 60% sodium hydride (140 mg, 3.4 mmol) is added. After stirring for 10 min, methyl iodide (0.28 mL, 4.5 mmol) is added and the mixture is stirred for 16 hr. Then saturated NH₄Cl aqueous solution (5 mL) is added along with EtOAc (30 mL) and water (15 mL). The mixture is stirred for 5 min and the aqueous layer is separated and extracted with EtOAc (2×20 mL). All organic layers are combined and concentrated to give the crude product. Purification by flash column chromatography affords 320 mg of the title product.

Intermediate B4: Synthesis of 6-bromo-1-methyl-1H-indazole-4-carbonitrile

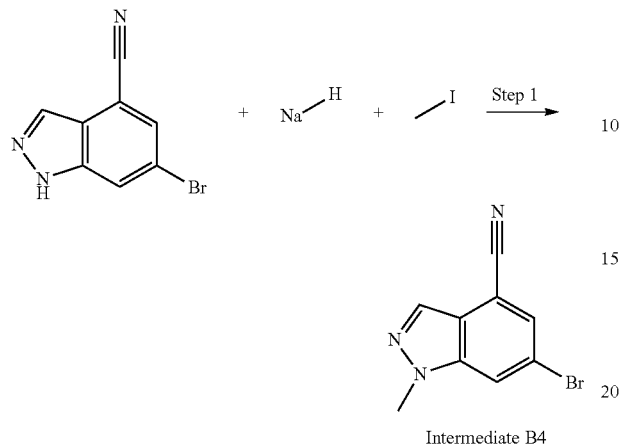

Intermediate B4

6-Bromo-1H-indazole-4-carbonitrile (500 mg, 2.3 mmol) is dissolved in THF (20 mL) and 60% sodium hydride (140 mg, 3.4 mmol) is added. After stirring for 10 min, methyl iodide (0.28 mL, 4.5 mmol) is added and the mixture is stirred for 16 hr. Then saturated NH$_4$Cl aqueous solution (5 mL) is added along with EtOAc (30 mL) and water (15 mL). The mixture is stirred for 5 min and the aqueous layer is separated and extracted with EtOAc (2×20 mL). All organic layers are combined and concentrated to give the crude product. Purification by flash column chromatography affords 290 mg of the title product.

Intermediate B5: Synthesis of 6-bromo-4-fluoro-1-methyl-1H-indazole

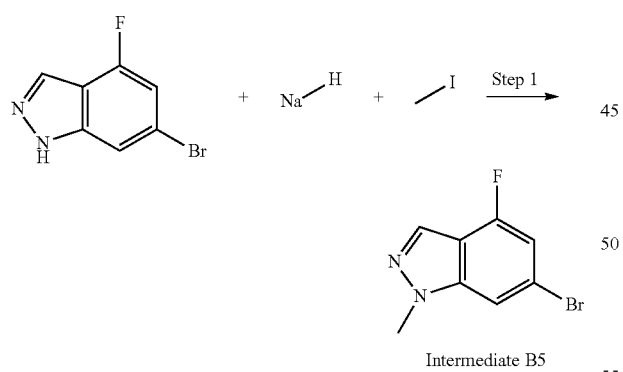

Intermediate B5

6-Bromo-4-fluoro-1H-indazole (2.4 g, 11 mmol) is dissolved in THF (100 mL) and 60% sodium hydride (680 mg, 17 mmol) is added. After stirring for 10 min, methyl iodide (1.4 mL, 23 mmol) is added and the mixture is stirred for 16 hr. Then saturated NH$_4$Cl aqueous solution (25 mL) is added along with EtOAc (50 mL) and water (35 mL). The mixture is stirred for 5 min and the aqueous layer is separated and extracted with EtOAc (2×50 mL). All organic layers are combined and concentrated to give the crude product. Purification by flash column chromatography affords 1.0 g of the title product.

Intermediate B6: Synthesis of 7-bromo-2,3-dihydro-5H-benzo[e][1,4]dioxepine

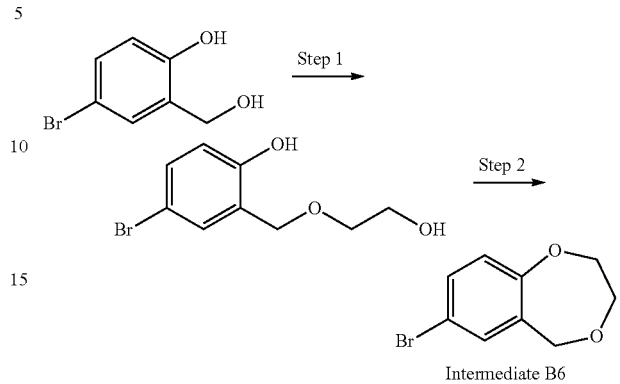

Intermediate B6

To a stirred solution of 4-bromo-2-hydroxymethyl-phenol (10 g, 49 mmol) in ethylene glycol (57 g, 910 mmol) is added p-toluenesulfonic acid (1.0 g, 6.0 mmol) at room temperature. The mixture is heated up to 100° C. for 4 hr. Then ice is used to quench the reaction and the mixture is extracted with EtOAc. The organic layer is separated, dried and concentrated to give the crude product. Purification by flash column chromatography affords 8.0 g of 4-bromo-2-(2-hydroxy-ethoxymethyl)-phenol.

To a stirred solution of 4-bromo-2-(2-hydroxy-ethoxymethyl)-phenol (7.0 g, 28 mmol) in DCM (300 mL) at 0° C. is added triphenylphosphine (11 g, 42 mmol) and diisopropyl azodicarboxylate (6.9 g, 34 mmol). The reaction mixture is slowly warmed to room temperature for 16 hr. Then the reaction is quenched with ice water and extracted with DCM. The organic layer is separated and concentrated to give the crude product. Purification by flash silica column chromatography affords 1.8 g of the title product.

Intermediate B7 and B8: Syntheses of the Enantiomers of 6-bromo-chroman-4-ol

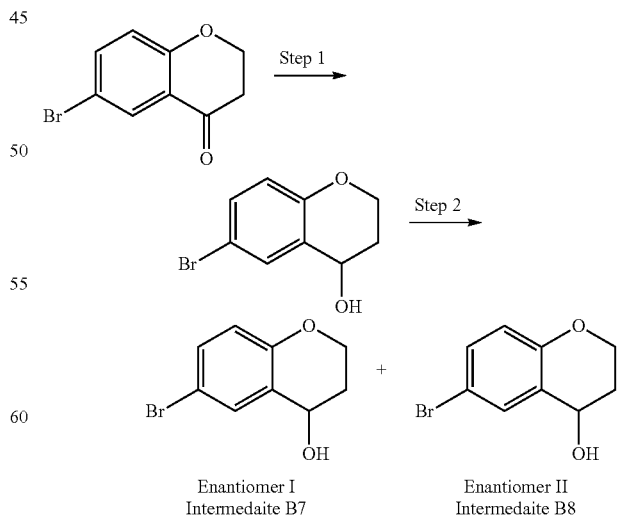

Enantiomer I  Enantiomer II
Intermedaite B7  Intermedaite B8

To a stirred solution of 6-bromo-chroman-4-one (4.0 g, 18 mmol) in methanol (100 mL) at 0° C. is added sodium borohydride (1.0 g, 26 mmol) slowly. The reaction mixture is warmed to room temperature for 2 hr. Then it is cooled down to 0° C. and NaHCO₃ solution is added to quench the reaction. The mixture is warmed to room temperature and extracted with DCM. The organic layer is separated, dried and concentrated to give 3.5 g of racemic 6-bromo-chroman-4-ol.

Chiral separation of the racemic 6-bromo-chroman-4-ol (3.5 g, 15 mmol) using Supercritical Fluid Chromatography affords 1.5 g of Enantiomer I (Intermediate B7, 2.10 min) and 1.5 g of Enantiomer II (Intermediate B8, 2.69 min). The retention times are measured using the following conditions: LUX 5 u Cellulose 3 Analytical Column, Mobile phase 5% (1:1:1 MeOH:EtOH:iPA): CO₂ @ 3 mL/min, 200 bar, 40° C.

Intermediate B9 and B10: Syntheses of the Enantiomers of 6-bromo-4-methyl-chroman-4-ol

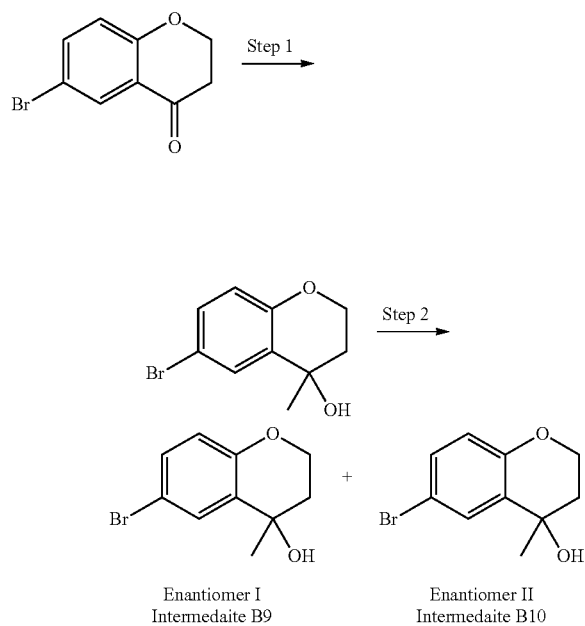

To a stirred solution of 6-bromo-chroman-4-one (6.7 g, 30 mmol) in THF (70 mL) is added cerium(III) chloride (3.6 g, 15 mmol) and the mixture is cooled down to −50° C. Then 3.0 M MeMgI in diethyl ether (30 mL, 90 mmol) is added dropwise and the reaction mixture is warmed to 15° C. in 45 min. The saturated aqueous NH₄Cl solution is added and the mixture is extracted with EtOAc (2×50 mL). The organic layers are combined and concentrated to give the crude product. Purification by flash column chromatography affords 3.5 g of racemic 6-bromo-4-methyl-chroman-4-ol.

Chiral separation of the racemic 6-bromo-4-methyl-chroman-4-ol (3.5 g, 14 mmol) using Supercritical Fluid Chromatography affords 1.0 g of Enantiomer I (Intermediate B9, 1.22 min) and 1.3 g of Enantiomer II (Intermediate B10, 2.15 min). The retention times are measured using the following conditions: LUX Amylose-2 4.6×250 mm Column, Mobile phase 10% (1:1:1 MeOH:EtOH:iPA):CO₂ @ 3 mL/min, 200 bar, 40° C.

Intermediate B11: Synthesis of 6-bromo-4,4-difluoro-chroman

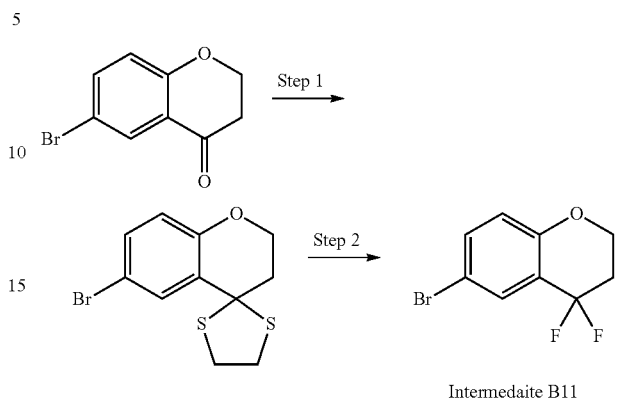

To a stirred solution of 6-bromo-chroman-4-one (5.0 g, 22 mmol) in DCM (100 mL) at 0° C. are added 1,2-ethanedithiol (4.1 g, 44 mmol) and boron trifluoride etherate (1.6 g, 11 mmol). The reaction mixture is stirred at room temperature for 16 hr before it is poured into 1.0 N NaOH solution. The mixture is extracted with DCM and the organic layers are separated, dried and concentrated to give the crude product. Washing the crude product with n-pentane affords 4.1 g of 6'-bromospiro[1,3-dithiolane-2,4'-chromane].

A suspension of N-iodosuccinimide (6.1 g, 27 mmol) in DCM (80 mL) is cooled down to −70° C. Hydrogen fluoride pyridine complex (5.4 g, 54 mmol) is added dropwise. A solution of 6'-bromospiro[1,3-dithiolane-2,4'-chromane] (4.1 g, 14 mmol) in DCM (cooled at −70° C.) is added dropwise and the mixture is stirred at −70° C. for 30 min. Then the reaction solution is poured into a mixture of hexane and DCM and the resulting mixture is filtered through a short pad of silica gel. The filtrate is concentrated to give the crude product. Purification by flash silica column chromatography affords 1.1 g of the title product.

Intermediate B12: Synthesis of 8-bromo-3,4-dihydro-2H-benzo[f][1,4]oxazepin-5-one

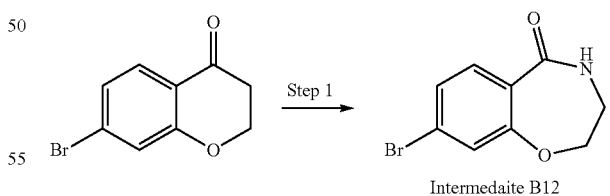

To a stirred solution of 7-bromo-chroman-4-one (1.0 g, 4.4 mmol) in DCM (40 mL) at 0° C. are added sodium azide (430 mg, 6.6 mmol) and methanesulfonic acid (6.3 g, 66 mmol). The reaction mixture is stirred at 0° C. for 4 hr before water is added. The mixture is extracted with DCM and the organic layer is separated and concentrated to give the crude product. Purification by flash silica column chromatography affords 560 mg of the title product.

Intermediate B13: Synthesis of 8-bromo-5,5-difluoro-1,3,4,5-tetrahydro-benzo[c]oxepine

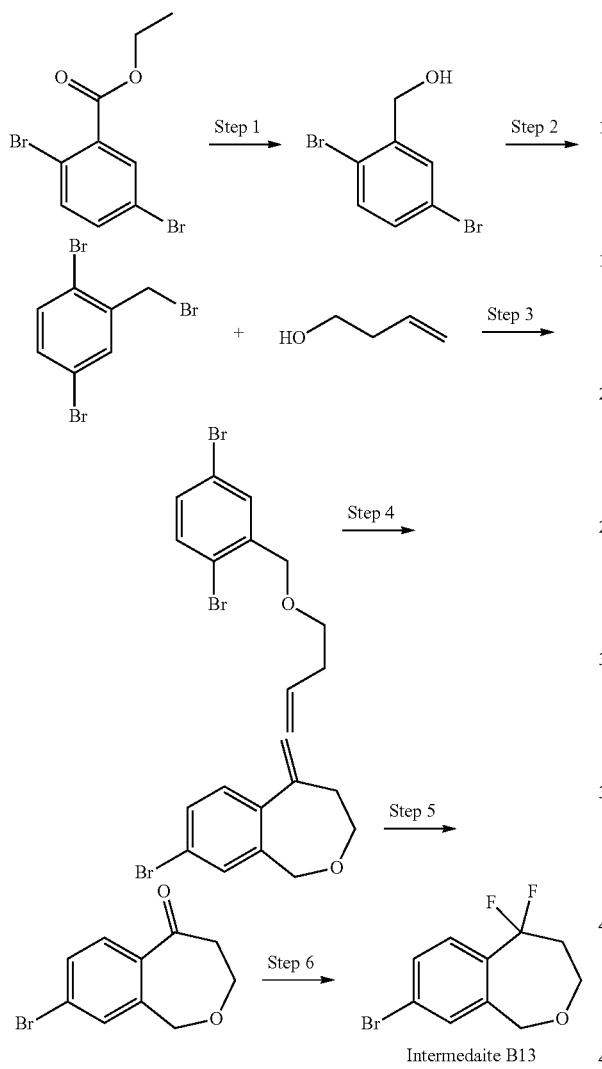

Intermedaite B13

To a stirred solution of 2,5-dibromo-benzoic acid ethyl ester (90 g, 290 mmol) in ethanol (900 mL) at 0° C. is added sodium borohydride (33 g, 880 mmol). The mixture is stirred at room temperature for 12 hr and then refluxed for 20 hr. The solvent is removed and water is added to the residue. The mixture is extracted with EtOAc and the organic layers are combined and concentrated to give the crude product. Purification by flash column chromatography affords 35 g of (2,5-dibromo-phenyl)-methanol.

To a stirred solution of (2,5-dibromo-phenyl)-methanol (40 g, 150 mmol) and triphenylphospine (59 g, 230 mmol) in THF (1000 mL) at 0° C. is added carbon tetrabromide (75 g, 230 mmol) slowly. The reaction mixture is stirred at room temperature for 2 hr and the solvent is removed to give the crude product. Purification by flash column chromatography affords 40 g of 1,4-dibromo-2-bromomethyl-benzene.

To a stirred solution of 3-buten-1-ol (13 g, 180 mmol) in THF (500 mL) at 0° C. is added 60% sodium hydride (7.3 g, 180 mmol). The mixture is stirred for 30 min at 0° C. before 1,4-dibromo-2-bromomethyl-benzene (40 g, 120 mmol) in THF (300 mL) is added. Then the reaction mixture is allowed to warm up to room temperature for 12 hr and ice is added to quench the reaction. The mixture is extracted with EtOAc and the organic layers are combined, dried and concentrated to give the crude product. Purification by flash column chromatography affords 25 g of 1,4-dibromo-2-but-3-enyloxymethyl-benzene.

To a stirred solution of 1,4-dibromo-2-but-3-enyloxymethyl-benzene (25 g, 78 mmol) in acetonitrile (1000 mL) silver carbonate (26 g, 94 mmol) is added. Then tetrakis(triphenylphosphine)palladium(0) (9.0 g, 7.8 mmol) is added after the reaction mixture is purged with argon gas for 10 min. The reaction mixture is heated at 100° C. for 24 hr. The solvent is removed and the residue is extracted with EtOAc. The organic solution is then concentrated to give the crude product. Purification by flash column chromatography affords 10 g of 8-bromo-5-methylene-1,3,4,5-tetrahydro-benzo[c]oxepine.

To a stirred solution of 8-bromo-5-methylene-1,3,4,5-tetrahydro-benzo[c]oxepine (10 g, 42 mmol) in THF/Water (400 mL, 1:1) at 0° C. are added sodium periodate (20 g, 93 mmol) and osmium tetraoxide (2.1 g, 8.2 mmol). The reaction mixture is then warmed up to room temperature for 1 hr before it is diluted with water. The mixture is extracted with EtOAc and the organic layer is separated, washed with brine, dried over anhydrous $Na_2SO_4$ and concentrated to give the crude product. Purification by flash column chromatography affords 4.0 g of 8-bromo-3,4-dihydro-1H-benzo[c]oxepin-5-one.

To a stirred solution of 8-bromo-3,4-dihydro-1H-benzo[c]oxepin-5-one (3.5 g, 15 mmol) in DCM (10 mL) is added diethylaminosulfur trifluoride (9.4 g, 58 mmol). The mixture is refluxed for 14 hr before methanol is added. Then saturated aqueous $NaHCO_3$ solution is added and the organic layer is separated. The aqueous layer is extracted with DCM and all the organic layers are combined, washed with brine, dried over anhydrous $Na_2SO_4$ and concentrated to give the crude product. Purification by flash column chromatography affords 1.7 g of the title product.

Intermediate B14: Synthesis of 3-fluoro-1-methyl-6-(4,4,5,5-tetramethyl-[1,3,2]dioxaborolan-2-yl)-1H-indazole

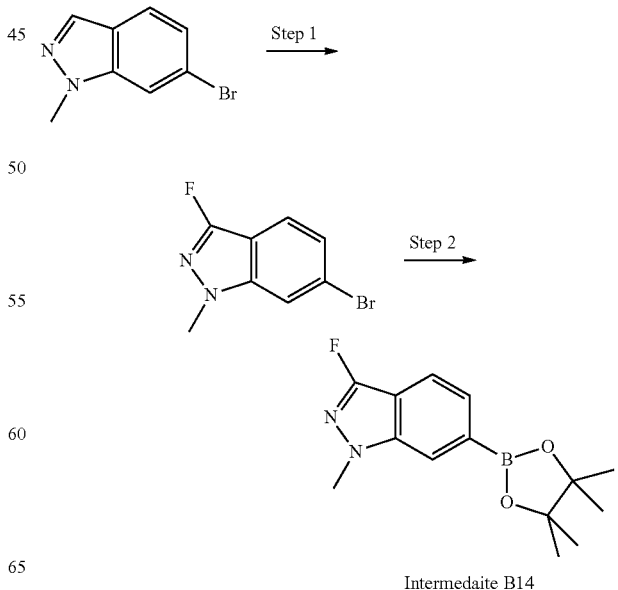

Intermedaite B14

To a stirred solution of 6-bromo-1-methyl-1H-indazole (20 g, 95 mmol) in acetonitrile (300 mL) is added 1-chloromethyl-4-fluoro-1,4-diazoniabicyclo[2.2.2]octane bis(tetrafluoroborate) (42 g, 120 mmol) and the reaction mixture is heated at 90° C. for 2 hr. Water is added and the mixture is extracted with EtOAc. The organic layers are combined, dried over $Na_2SO_4$ and concentrated to give the crude product. Purification by flash column chromatography affords 6.0 g of 6-bromo-3-fluoro-1-methyl-1H-indazole.

To a stirred solution of 6-bromo-3-fluoro-1-methyl-1H-indazole (5.0 g, 22 mmol) in 1,4-dioxane (100 mL) are added bis(pinacolato)diboron (3.5 g, 14 mmol) and potassium acetate (3.5 g, 36 mmol). The mixture is purged with argon gas for 10 min and dichloro[1,1'-bis(diphenylphosphino)ferrocene]palladium(II) (1.0 g, 1.0 mmol) is added. The reaction mixture is heated at 100° C. for 5 hr and water is added. The mixture is extracted with EtOAc and the organic layers are combined and concentrated to give the crude product. Purification by flash column chromatography affords 2.0 g of the title product.

Intermediate B15: Synthesis of 6-bromo-3,4-dihydro-2H-[1,8]naphthyridine-1-carboxylic Acid Amide

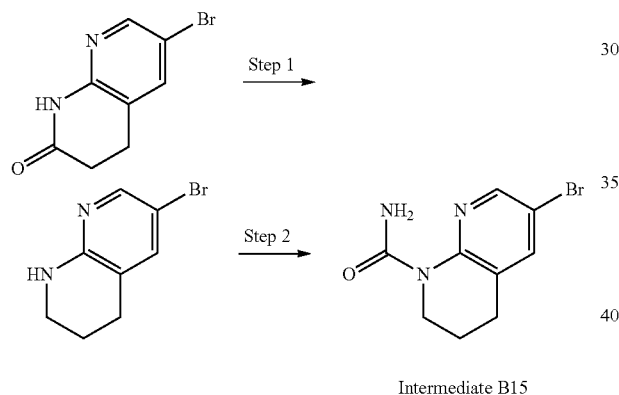

Intermediate B15

To a cooled (0° C.) solution 6-bromo-3,4-dihydro-1H-[1,8]naphthyridin-2-one (10 g, 44 mmol) in THF (500 mL) is added sodium borohydride (8.3 g, 220 mmol) followed by boron trifluoride diethyl ether complex (39 mL, 310 mmol) dropwise. The resulting mixture is allowed to warm to room temperature and it is stirred for 16 hr. The reaction is carefully quenched with the dropwise addition of 1.0 N HCl aqueous solution (15 mL). Once quenched, additional 1.0 N HCl aqueous solution (85 mL) is added and the mixture is stirred at room temperature for 16 hr. The mixture is then concentrated, diluted with water and made basic (pH 8) with the addition of powdered sodium bicarbonate. The mixture is extracted with EtOAc and the combined organic layers are washed with brine, dried over $Na_2SO_4$ and concentrated to give 9.3 g of 6-bromo-1,2,3,4-tetrahydro-[1,8]naphthyridine.

To a cooled (0° C.) solution of 6-bromo-1,2,3,4-tetrahydro-[1,8]naphthyridine (6.4 g, 30 mmol) in DCM (75 mL) is added trichloroacetyl isocyanate (3.8 mL, 32 mmol). After stirring for 1 hr at 0° C., a solution of methanolic KOH (1.0 M, 10 mL) is added. The resulting mixture is allowed to warm up to room temperature and it is stirred for 16 hr. The reaction mixture is concentrated to give the crude product. Purification by flash column chromatography affords 7.4 g of the title product.

Intermediate B16: Synthesis of Trifluoro-Methanesulfonic Acid 4-cyano-cyclohex-1-enyl ester

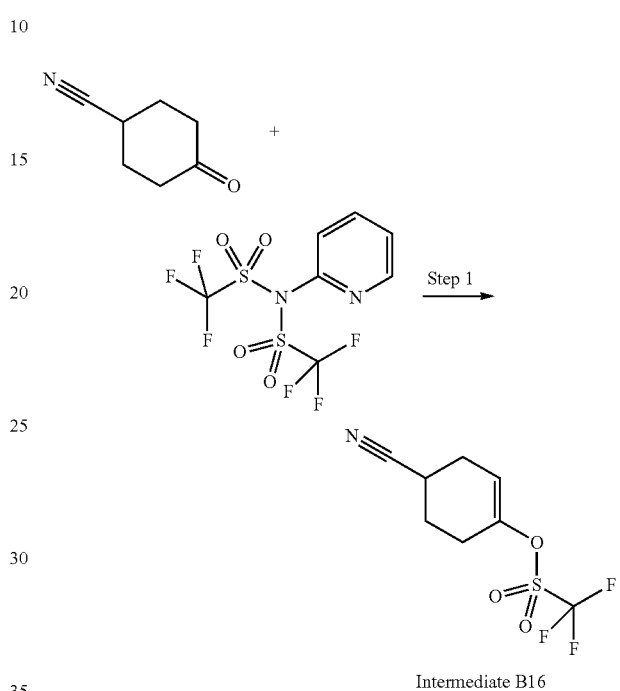

Intermediate B16

4-Oxo-cyclohexanecarbonitrile (2.0 g, 16 mmol) is dissolved in THF (100 mL) and it is cooled down to −78° C. Then 2.0 M lithium diisopropylamide THF solution (9.5 mL, 19 mmol) is added and the mixture is stirred for 30 min at −78° C. 2[N,N-bis(trifluoromethylsulfonyl)amino]pyridine (7.0 g, 20 mmol) is added and the mixture is allowed to warm to room temperature and it is stirred for 16 hr. Then 200 mL of EtOAc is added along with 100 mL of saturated aqueous $NH_4Cl$ solution. The organic layer is separated and washed with 100 mL of water and 100 mL of brine before it is concentrated to give the crude product. Purification by flash column chromatography affords 1.9 g of the title product.

Intermediate B17: Synthesis of Trifluoro-Methanesulfonic Acid 1-methyl-4,5-dihydro-1H-indazol-6-yl ester

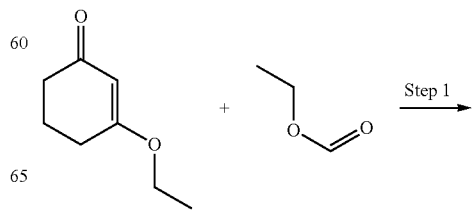

87

-continued

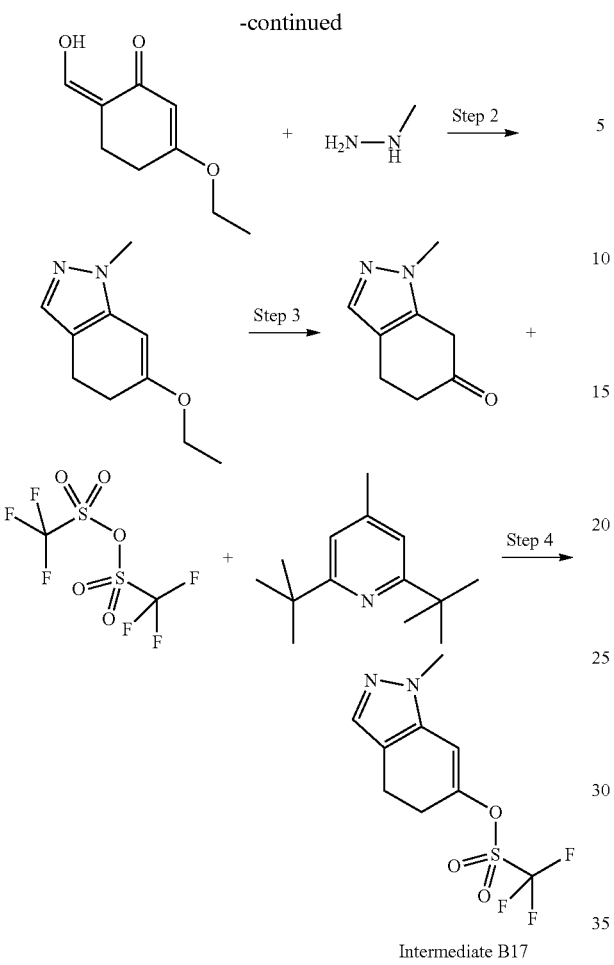

Intermediate B17

To a suspension of 60% NaH (12 g, 290 mmol) in 200 mL of Et₂O is added EtOH (17 mL, 300 mmol) at 4° C. The mixture is stirred for 30 min before 3-ethoxy-cyclohex-2-enone (7.0 g, 50 mmol) is added. The mixture is stirred for 1 hr and it is cooled down to 0° C. Then formic acid ethyl ester (12 mL, 150 mmol) is added and the mixture is stirred for 18 hr. Water (200 mL) is added along with EtOAc (400 mL). The organic layer is removed and the aqueous layer is acidified to pH 4 and buffered with 2 M KHCO₃. Then the aqueous layer is extracted with DCM (2×300 mL) and the DCM layers are dried and concentrated to give 8.3 g of 3-ethoxy-6-[1-hydroxy-meth-(Z)-ylidene]-cyclohex-2-enone.

To the solution of 3-ethoxy-6-[1-hydroxy-meth-(Z)-ylidene]-cyclohex-2-enone (8.3 g, 49 mmol) in EtOH (40 mL) is added methylhydrazine (13 mL, 250 mmol). The mixture is stirred for 16 hr before it is concentrated to give the crude product. Purification by flash column chromatography affords 3.6 g of 6-ethoxy-1-methyl-4,5-dihydro-1H-indazole.

6-Ethoxy-1-methyl-4,5-dihydro-1H-indazole (3.6 g, 20 mmol) is added into the 1.0 N HCl solution (15 mL). The mixture is stirred for 3 hr before it is made basic by the addition of solid NaHCO₃. The mixture is then extracted with DCM (3×120 mL) and all the organic layers are combined, dried over anhydrous MgSO₄ and concentrated to give 2.8 g of 1-methyl-1,4,5,7-tetrahydro-indazol-6-one.

1-Methyl-1,4,5,7-tetrahydro-indazol-6-one (2.5 g, 17 mmol) is dissolved in DCM (200 mL) and the solution is

88 cooled down to 4° C. Then 2,6-di-tert-butyl-4-methyl-pyridine (5.2 g, 25 mmol) is added followed by the addition of trifluoromethanesulfonic anhydride (4.2 mL, 25 mmol). The mixture is allowed to warm to room temperature and stir for 16 hr. EtOAc (400 mL) is added along with water (200 mL). The organic layer is separated, washed with 200 mL of water, 200 mL of saturated NH₄Cl and 200 mL of brine before it is concentrated to give the crude product. Purification by flash column chromatography affords 2.3 g of the title product.

Intermediate B18: Synthesis of 4,4-difluoro-7-(4,4,5,5-tetramethyl-[1,3,2]dioxaborolan-2-yl)-isochroman

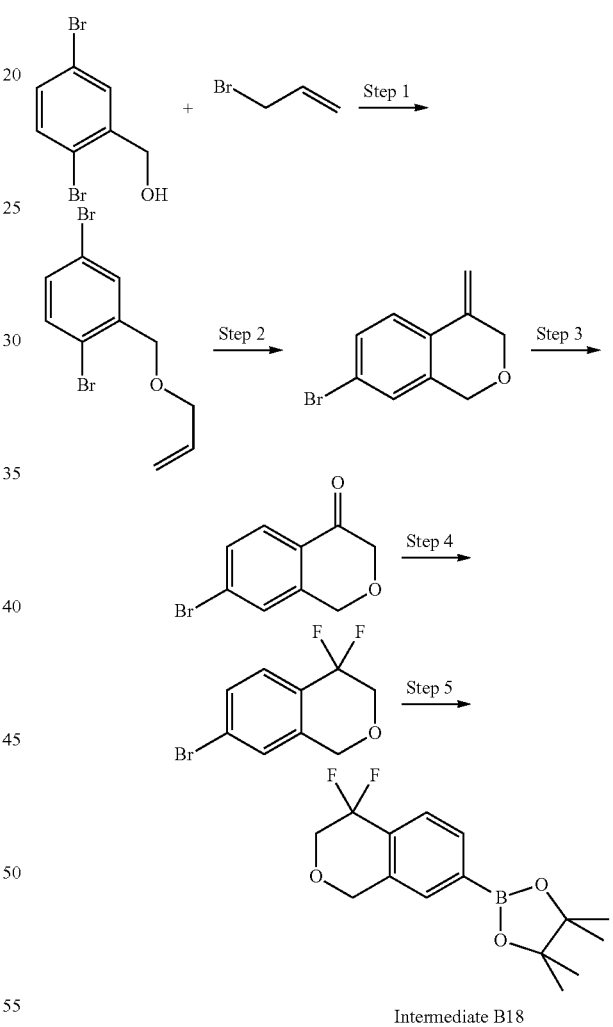

Intermediate B18

To a stirred solution of (2,5-dibromo-phenyl)-methanol (45 g, 170 mmol) in THF (1000 mL) is added 60% NaH in mineral oil (10 g, 250 mmol) at 0° C. The mixture is stirred for 30 min and allyl bromide (25 g, 203 mmol) is added. Then the mixture is warmed up to room temperature for 12 hrs. The reaction is quenched with ice and the mixture is extracted with EtOAc. The organic layers are combined, dried and concentrated to give the crude product. Purification by flash column chromatography affords 45 g of 2-allyloxymethyl-1,4-dibromo-benzene.

To a stirred solution of 2-allyloxymethyl-1,4-dibromo-benzene (14 g, 46 mmol) in DMF (500 mL) are added Cs$_2$CO$_3$ (30 g, 92 mmol) and tetrabutylammonium iodide (17 g, 46 mmol). The reaction mixture is purged with argon gas for 10 min and tetrakis(triphenylphosphine)palladium(0) (5.3 g, 4.6 mmol) is added. The reaction mixture is then heated at 100° C. for 12 hrs and water is then added. The mixture is extracted with EtOAc and organic layers are dried and concentrated to give the crude product. Purification by flash column chromatography affords 5 g of 7-bromo-4-methylene-isochroman.

To a stirred solution of 7-bromo-4-methylene-isochroman (5.0 g, 22 mmol) in THF/water (200 mL, 1:1) are added sodium periodate (10 g, 49 mmol) and osmium tetraoxide (1.1 g, 4.0 mmol) at 0° C. The reaction mixture is warmed up to room temperature for 1 hr. Then water is added and the mixture is extracted with EtOAc. The organic layers are combined, washed with brine, dried and concentrated to give the crude product. Purification by flash column chromatography affords 400 mg of 7-bromo-isochroman-4-one.

To a stirred solution of 7-bromo-isochroman-4-one (400 mg, 1.8 mmol) in DCM (2.0 mL) is added diethylamino-sulfur trifluoride (1.1 g, 6.8 mmol) at room temperature. The mixture is heated at 70° C. for 14 hrs. Then MeOH is added along with saturated aqueous NaHCO$_3$.solution. The aqueous layer is separated and extracted with DCM (2×20 mL). All the organic layers are combined, washed with brine, dried and concentrated to give the crude product. Purification by flash column chromatography affords 200 mg of 7-bromo-4,4-difluoro-isochroman.

To a stirred solution of 7-bromo-4,4-difluoro-isochroman (500 mg, 2.0 mmol) in 1,4-dioxane (20 mL) are added potassium acetate (590 mg, 6.0 mmol) and bis(pinacolato)diboron (560 mg, 2.0 mmol). The reaction mixture is purged with argon for 15 min and dichloro[1,1'-bis(diphenylphosphino)ferrocene]palladium(II) DCM adduct (160 mg, 0.20 mmol) is added. The reaction mixture is then heated at 100° C. for 14 hrs and water is added. The mixture is stirred for 10 min and it is extracted with EtOAc. The organic layers are combined, washed with brine, dried and concentrated to give the crude product. Purification by flash column chromatography affords 300 mg of the titled product.

Example 1: Synthesis of 8-(3-fluoro-1-methyl-1H-indazol-6-yl)-3,4-dihydro-1H-pyrano[4,3-c]pyridin-4-ol, Enantiomer II (Cpd 15, Table 1)

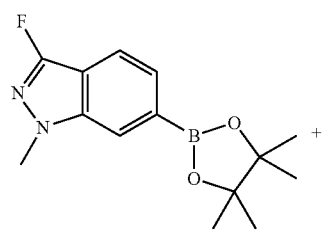

Intermediate B14

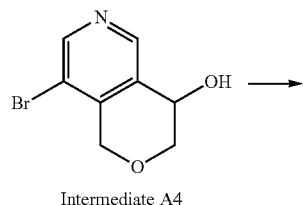

Intermediate A4

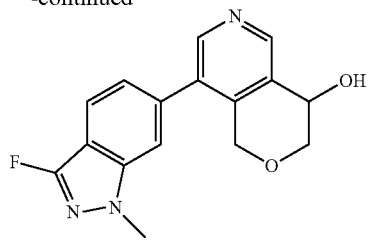

Intermediate B14 (72 mg, 0.26 mmol), Intermediate A4 (50 mg, 0.22 mmol) and 2.0 M aqueous Na$_2$CO$_3$ solution (0.22 mL, 0.44 mmol) are mixed in 1,4-dioxane (2.0 mL). The reaction mixture is purged with argon gas for 5 min. Then [1,1'-bis(diphenylphosphino)ferrocene]palladium(II) dichloride (16 mg, 0.022 mmol) is added and the mixture is heated at 100° C. for 3.5 hr. The solvents are removed and the residue is purified by flash column chromatography to give 38 mg of the title product.

Compounds 1 to 14, 16 to 69, 188 and 193 to 200 in Table 1 are synthesized according to the procedure for Example 1, substituting Intermediate B14 and/or Intermediate A4 with either commercially available reagents or the appropriate intermediates listed below.

| Cpd No | Boronic acid/ester | Bromide |
| --- | --- | --- |
| 1 | Commercial | Intermediate A4 |
| 2 | Commercial | Intermediate A3 |
| 3 | Commercial | Intermediate A3 |
| 4 | Commercial | Intermediate A3 |
| 5 | Commercial | Intermediate A4 |
| 6 | Commercial | Intermediate A4 |
| 7 | Commercial | Intermediate A3 |
| 8 | Commercial | Intermediate A3 |
| 9 | Commercial | Intermediate A6 |
| 10 | Commercial | Intermediate A3 |
| 11 | Commercial | Intermediate A3 |
| 12 | Commercial | Intermediate A4 |
| 13 | Commercial | Intermediate A4 |
| 14 | Commercial | Intermediate A4 |
| 16 | Commercial | Intermediate A7 |
| 17 | Commercial | Intermediate A8 |
| 18 | Commercial | Intermediate A4 |
| 19 | Commercial | Intermediate A3 |
| 20 | Commercial | Intermediate A3 |
| 21 | Commercial | Intermediate A3 |
| 22 | Commercial | Intermediate A3 |
| 23 | Commercial | Intermediate A3 |
| 24 | Commercial | Intermediate A3 |
| 25 | Commercial | Intermediate A3 |
| 26 | Commercial | Intermediate A3 |
| 27 | Commercial | Intermediate A3 |
| 28 | Commercial | Intermediate A3 |
| 29 | Commercial | Intermediate A3 |
| 30 | Commercial | Intermediate A3 |
| 31 | Commercial | Intermediate A3 |
| 32 | Commercial | Intermediate A4 |
| 33 | Commercial | Intermediate A4 |
| 34 | Commercial | Intermediate A4 |
| 35 | Commercial | Intermediate A4 |
| 36 | Commercial | Intermediate A4 |
| 37 | Commercial | Intermediate A4 |
| 38 | Commercial | Intermediate A4 |
| 39 | Commercial | Intermediate A4 |
| 40 | Commercial | Intermediate A4 |
| 41 | Commercial | Intermediate A4 |
| 42 | Commercial | Intermediate A4 |
| 43 | Commercial | Intermediate A4 |
| 44 | Commercial | Intermediate A4 |

-continued

| Cpd No | Boronic acid/ester | Bromide |
|---|---|---|
| 45 | Commercial | Intermediate A4 |
| 46 | Commercial | Intermediate A4 |
| 47 | Commercial | Intermediate A4 |
| 48 | Commercial | Intermediate A4 |
| 49 | Commercial | Intermediate A4 |
| 50 | Commercial | Intermediate A4 |
| 51 | Commercial | Intermediate A4 |
| 52 | Commercial | Intermediate A4 |
| 53 | Commercial | Intermediate A3 |
| 54 | Commercial | Intermediate A3 |
| 55 | Intermediate B14 | Intermediate A3 |
| 56 | Commercial | Intermediate A11 |
| 57 | Commercial | Intermediate A11 |
| 58 | Commercial | Intermediate A11 |
| 59 | Commercial | Intermediate A11 |
| 60 | Commercial | Intermediate A11 |
| 61 | Commercial | Intermediate A11 |
| 62 | Commercial | Intermediate A11 |
| 63 | Commercial | Intermediate A12 |
| 64 | Commercial | Intermediate A12 |
| 65 | Commercial | Intermediate A12 |
| 66 | Commercial | Intermediate A12 |
| 67 | Commercial | Intermediate A12 |
| 68 | Intermediate B14 | Intermediate A12 |
| 69 | Commercial | Intermediate A12 |
| 188 | Commercial | Intermediate A3 |
| 193 | Commercial | Intermediate A11 |
| 194 | Intermediate B18 | Intermediate A11 |
| 195 | Commercial | Intermediate A12 |
| 196 | Intermediate B18 | Intermediate A12 |
| 197 | Commercial | Intermediate A7 |
| 198 | Commercial | Intermediate A8 |
| 199 | Intermediate B18 | intermediate A4 |
| 200 | Intermediate B18 | intermediate A3 |

Example 2: Synthesis 8-(1-methyl-1H-indazol-6-yl)-3,4-dihydro-1H-pyrano[4,3-c]pyridin-4-ylamine, Enantiomer II (Cpd 71, Table 1)

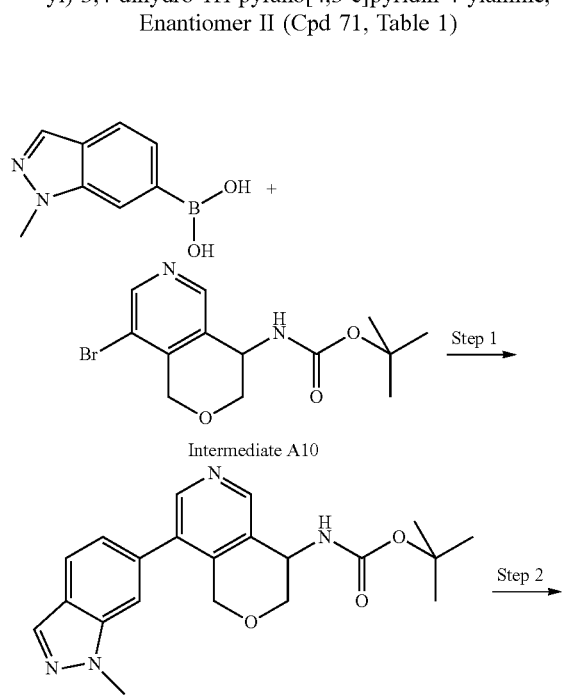

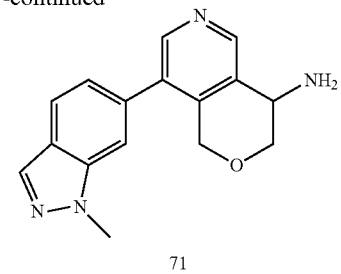

71

Intermediate A10 is coupled with (1-methylindazol-6-yl) boronic acid according to the procedure for Example 1 to give [8-(1-methyl-1H-indazol-6-yl)-3,4-dihydro-1H-pyrano[4,3-c]pyridin-4-yl]-carbamic acid tert-butyl ester in Step 1.

[8-(1-Methyl-1H-indazol-6-yl)-3,4-dihydro-1H-pyrano[4,3-c]pyridin-4-yl]-carbamic acid tert-butyl ester (410 mg, 1.1 mmol) is dissolved in DCM (2.0 mL) and trifluoroacetic acid (0.5 mL) is added. The mixture is stirred for 16 hr at room temperature and saturated aqueous $NaHCO_3$ solution (5 mL) is added along with 10 mL of water. The mixture is stirred for 10 min and the aqueous layer is separated and extracted with DCM (3×15 mL) and EtOAc (3×15 mL). All the organic layers are combined and concentrated to give the crude product. Purification by flash column chromatography affords 303 mg of the title product.

Compound 70 in Table 1 is synthesized according to the procedures for Example 2, substituting (1-methylindazol-6-yl)boronic acid with commercially available (1,5-dimethylindazol-6-yl)boronic acid in Step 1.

Example 3: Synthesis of N-[8-(1-methyl-1H-indazol-6-yl)-3,4-dihydro-1H-pyrano[4,3-c]pyridin-4-yl]-isobutyramide, Enantiomer II (Cpd 77, Table 1)

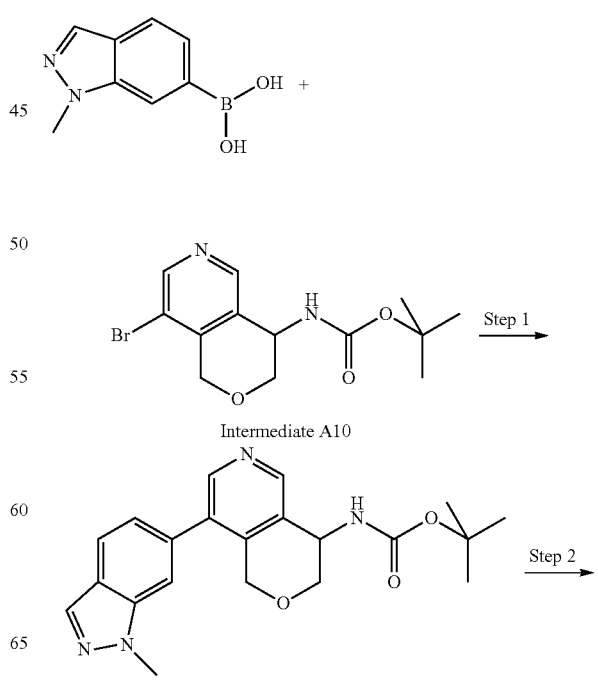

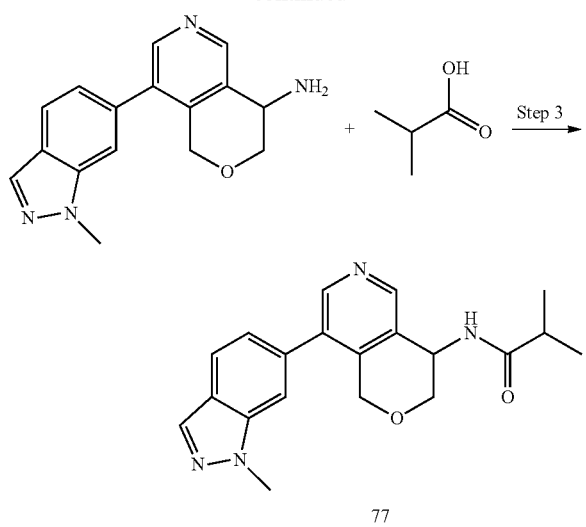

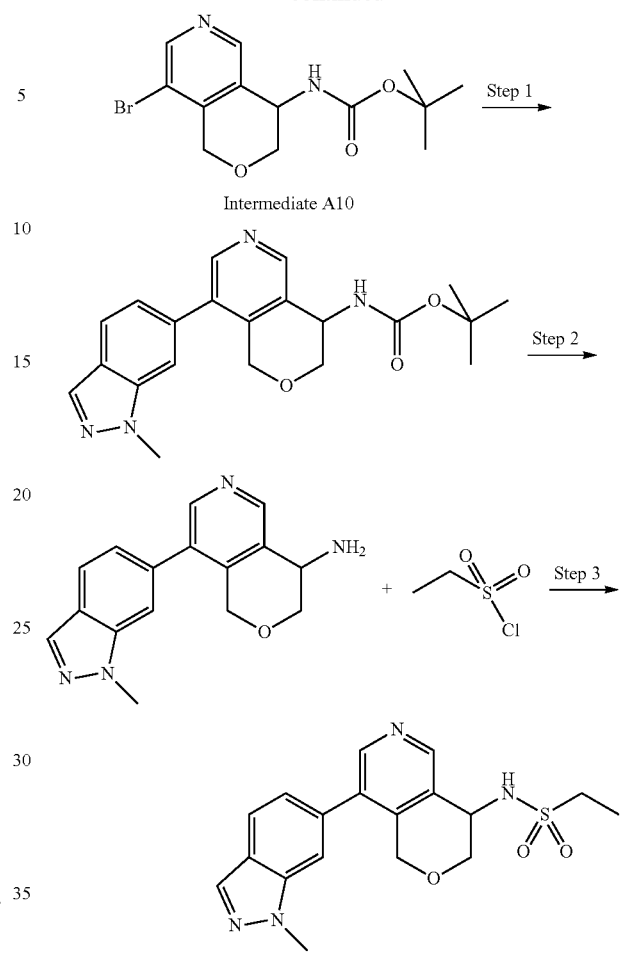

Intermediate A10 and (1-methylindazol-6-yl)boronic acid are converted to 8-(1-methyl-1H-indazol-6-yl)-3,4-dihydro-1H-pyrano[4,3-c]pyridin-4-ylamine according to the procedures for Example 2 in Step 1 and Step 2.

8-(1-Methyl-1H-indazol-6-yl)-3,4-dihydro-1H-pyrano[4,3-c]pyridin-4-ylamine (88 mg, 0.31 mmol), isobutyric acid (0.044 mL, 0.47 mmol) and triethyl amine (0.13 mL, 0.94 mmol) are mixed in acetonitrile (2.0 mL). Then 0-(benzotriazol-1-yl)-N,N,N',N'-tetramethyluronium tetrafluoroborate (120 mg, 0.38 mmol) is added and the mixture is stirred for 16 hr. All the solvent is removed and the residue is purified by flash column chromatography to give 40 mg of the title product.

Compounds 72 to 76 in Table 1 are synthesized according to the procedure for Example 3, substituting with either commercially available reagents or the appropriate intermediates listed below.

| Cpd No | Boronic acid/ester | Bromide |
| --- | --- | --- |
| 72 | Commercial | Intermediate A9 |
| 73 | Commercial | Intermediate A10 |
| 74 | Commercial | Intermediate A10 |
| 75 | Commercial | Intermediate A10 |
| 76 | Commercial | Intermediate A10 |

Example 4: Synthesis of Ethanesulfonic Acid [8-(1-methyl-1H-indazol-6-yl)-3,4-dihydro-1H-pyrano[4,3-c]pyridin-4-yl]-amide, Enantiomer II (Cpd 83, Table 1)

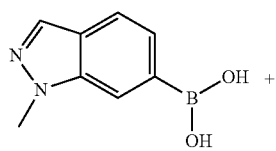

Intermediate A10 and (1-methylindazol-6-yl)boronic acid are converted to 8-(1-methyl-1H-indazol-6-yl)-3,4-dihydro-1H-pyrano[4,3-c]pyridin-4-ylamine according to the procedures for Example 2 in Step 1 and Step 2.

8-(1-Methyl-1H-indazol-6-yl)-3,4-dihydro-1H-pyrano[4,3-c]pyridin-4-ylamine (66 mg, 0.24 mmol) is dissolved in DCM (2.0 mL) and ethanesulfonyl chloride (0.025 mL, 0.26 mmol) is added. Then triethyl amine (0.066 mL, 0.47 mmol) is added and the mixture is stirred for 2 hr. All the solvent is removed to give the crude product. Purification by flash column chromatography affords 26 mg of the title product.

Compounds 78 to 82 in Table 1 are synthesized according to the procedure for Example 4, substituting with either commercially available reagents or the appropriate intermediates listed below.

| Cpd No | Boronic acid/ester | Bromide |
| --- | --- | --- |
| 78 | Commercial | Intermediate A9 |
| 79 | Commercial | Intermediate A10 |
| 80 | Commercial | Intermediate A9 |
| 81 | Commercial | Intermediate A10 |
| 82 | Commercial | Intermediate A10 |

Example 5: Synthesis of 8-(4-fluoro-1-methyl-1H-indazol-6-yl)-3,4-dihydro-1H-pyrano[4,3-c]pyridin-4-ol, Enantiomer II (Cpd 96, Table 1)

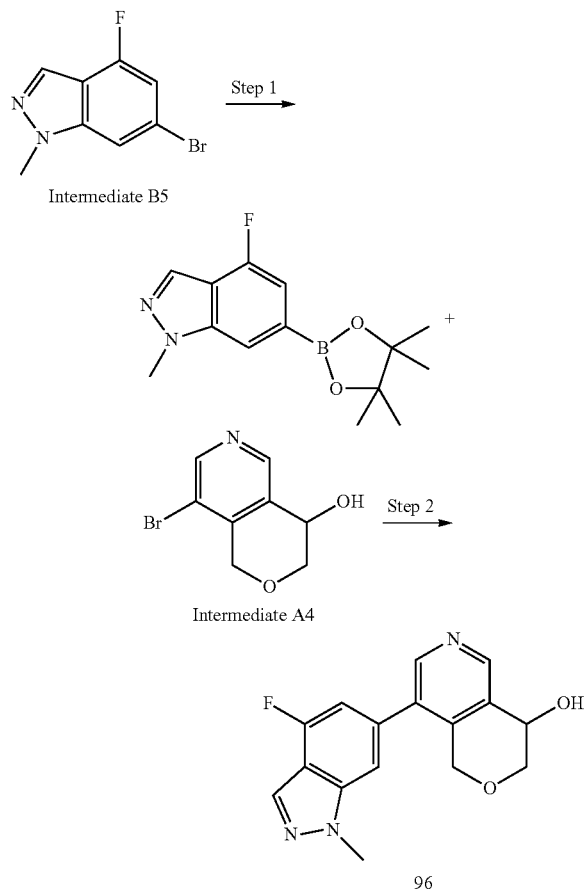

Intermediate B5 (69 mg, 0.30 mmol), bis(pinacolato)diboron (95 mg, 0.38 mmol) and potassium acetate (130 mg, 1.4 mmol) are mixed in 1,4-dioxane (3.0 mL) and the reaction mixture is purged with argon gas for 10 min. Then dichloro[1,1'-bis(diphenylphosphino)ferrocene]palladium (II) (22 mg, 0.030 mmol) is added and the mixture is heated at 90° C. for 16 hr. The reaction crude is cooled down to room temperature and it is used in the next step without workup and purification.

Intermediate A4 (50 mg, 0.22 mmol) and 2.0 M aqueous $Na_2CO_3$ solution (0.22 mL, 0.44 mmol) are added into the reaction crude obtained from the previous step. The mixture is purged with argon gas for 10 min. Then dichloro[1,1'-bis(diphenylphosphino)ferrocene]palladium(II) (16 mg, 0.022 mmol) is added and the mixture is heated at 100° C. for 3.5 hr. The reaction mixture is concentrated to give the crude product. Purification by flash column chromatography affords 27 mg of the title product.

Compound 84 to 95, Compound 97 to 148, Compound 163 to 164 and Compound 183 in Table 1 are synthesized according to the procedures for Example 5, substituting Intermediate B5 and/or Intermediate A4 with either commercially available reagents or the appropriate intermediates listed below.

| Cpd No | Bromide for Boronic ester | Bromide |
|---|---|---|
| 84 | Commercial | Intermediate A7 |
| 85 | Commercial | Intermediate A8 |
| 86 | Commercial | Intermediate A3 |
| 87 | Commercial | Intermediate A4 |
| 88 | Commercial | Intermediate A7 |
| 89 | Commercial | Intermediate A8 |
| 90 | Commercial | Intermediate A4 |
| 91 | Commercial | Intermediate A7 |
| 92 | Intermediate B5 | Intermediate A8 |
| 93 | Commercial | Intermediate A8 |
| 94 | Commercial | Intermediate A3 |
| 95 | Commercial | Intermediate A3 |
| 97 | Commercial | Intermediate A4 |
| 98 | Commercial | Intermediate A4 |
| 99 | Commercial | Intermediate A3 |
| 100 | Commercial | Intermediate A3 |
| 101 | Commercial | Intermediate A4 |
| 102 | Intermediate B15 | Intermediate A2 |
| 103 | Commercial | Intermediate A4 |
| 104 | Intermediate B1 | Intermediate A3 |
| 105 | Intermediate B1 | Intermediate A4 |
| 106 | Intermediate B4 | Intermediate A4 |
| 107 | Intermediate B6 | Intermediate A4 |
| 108 | Intermediate B6 | Intermediate A3 |
| 109 | Intermediate B2 | Intermediate A4 |
| 110 | Commercial | Intermediate A4 |
| 111 | Intermediate B6 | Intermediate A7 |
| 112 | Intermediate B6 | Intermediate A8 |
| 113 | Intermediate B3 | Intermediate A4 |
| 114 | Commercial | Intermediate A8 |
| 115 | Commercial | Intermediate A3 |
| 116 | Commercial | Intermediate A4 |
| 117 | Commercial | Intermediate A3 |
| 118 | Commercial | Intermediate A4 |
| 119 | Commercial | Intermediate A4 |
| 120 | Commercial | Intermediate A3 |
| 121 | Commercial | Intermediate A4 |
| 122 | Commercial | Intermediate A3 |
| 123 | Commercial | Intermediate A4 |
| 124 | Commercial | Intermediate A4 |
| 125 | Commercial | Intermediate A3 |
| 126 | Commercial | Intermediate A4 |
| 127 | Commercial | Intermediate A4 |
| 128 | Commercial | Intermediate A11 |
| 129 | Commercial | Intermediate A12 |
| 130 | Commercial | Intermediate A3 |
| 131 | Intermediate B7 | Intermediate A3 |
| 132 | Intermediate B7 | Intermediate A11 |
| 133 | Intermediate B7 | Intermediate A12 |
| 134 | Intermediate B8 | Intermediate A4 |
| 135 | Intermediate B8 | Intermediate A11 |
| 136 | Intermediate B8 | Intermediate A12 |
| 137 | Intermediate B9 | Intermediate A4 |
| 138 | Intermediate B9 | Intermediate A3 |
| 139 | Intermediate B10 | Intermediate A4 |
| 140 | Intermediate B10 | Intermediate A3 |
| 141 | Intermediate B11 | Intermediate A4 |
| 142 | Intermediate B11 | Intermediate A3 |
| 143 | Intermediate B11 | Intermediate A11 |
| 144 | Intermediate B11 | Intermediate A12 |
| 145 | Intermediate B12 | Intermediate A4 |
| 146 | Intermediate B12 | Intermediate A3 |
| 147 | Intermediate B12 | Intermediate A11 |
| 148 | Intermediate B13 | Intermediate A4 |
| 163 | Intermediate B15 | Intermediate A3 |
| 164 | Intermediate B15 | Intermediate A4 |
| 183 | Commercial | Intermediate A3 |

Example 6: Synthesis of 8-(4-fluoro-1-methyl-1H-indazol-6-yl)-3,4-dihydro-1H-pyrano[4,3-c]pyridin-4-ylamine, Enantiomer II (Cpd 149, Table 1)

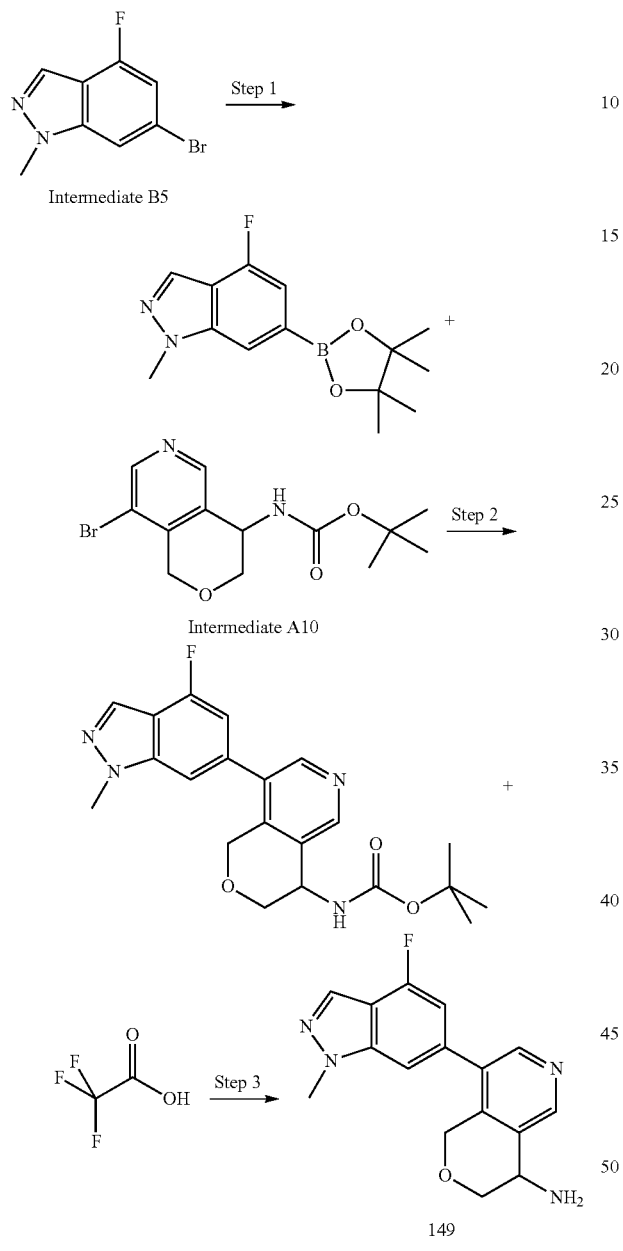

Intermediate B5 and Intermediate A10 are converted to [8-(4-fluoro-1-methyl-1H-indazol-6-yl)-3,4-dihydro-1H-pyrano[4,3-c]pyridin-4-yl]-carbamic acid tert-butyl ester according to the procedures for Example 5 in Step 1 and Step 2.

[8-(4-Fluoro-1-methyl-1H-indazol-6-yl)-3,4-dihydro-1H-pyrano[4,3-c]pyridin-4-yl]-carbamic acid tert-butyl ester (72 mg, 0.18 mmol) is dissolved in DCM (5.0 mL) and trifluoroacetic acid (0.3 mL) is added. The mixture is stirred for 3 hr and saturated aqueous NaHCO₃ (5 mL) is added along with 10 mL of water. The mixture is stirred for 10 min and the aqueous layer is separated and extracted with DCM (3×15 mL) and EtOAc (3×15 mL). All the organic layers are combined and concentrated to give the crude product. Purification by flash column chromatography affords 25 mg of the title product.

Example 7: Synthesis of N-[8-(4-fluoro-1-methyl-1H-indazol-6-yl)-3,4-dihydro-1H-pyrano[4,3-c]pyridin-4-yl]-propionamide, Enantiomer II (Cpd 150, Table 1)

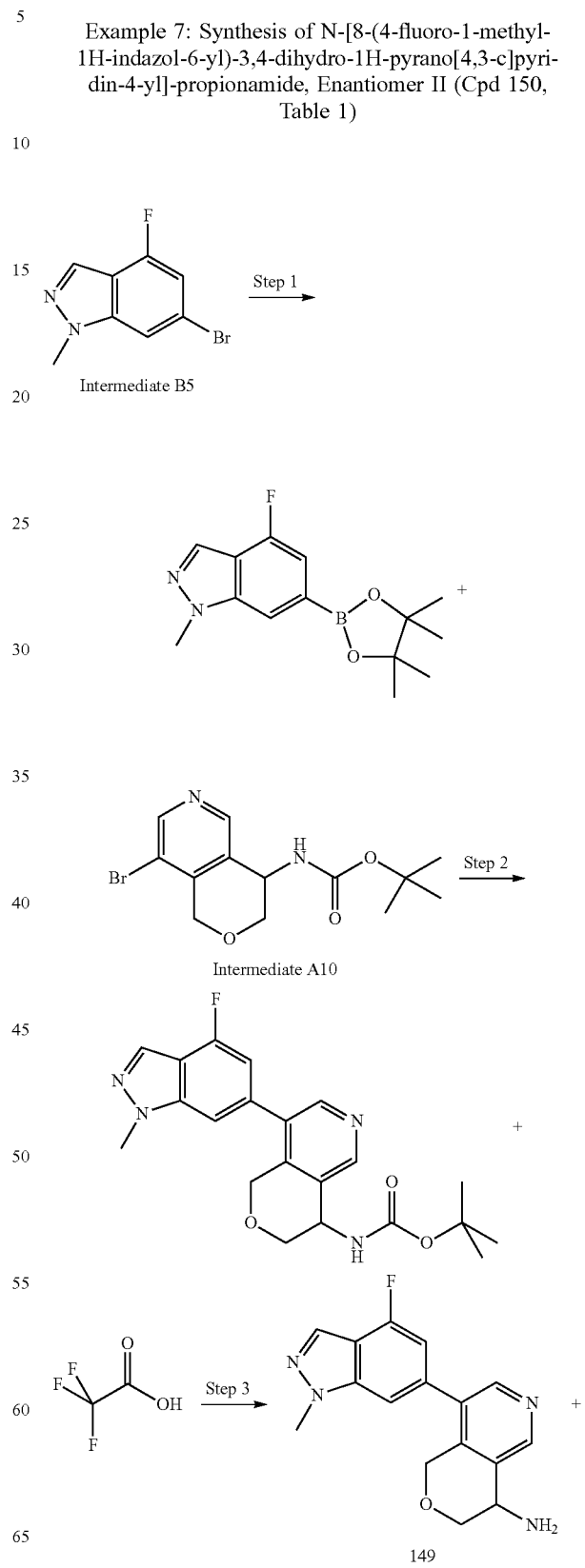

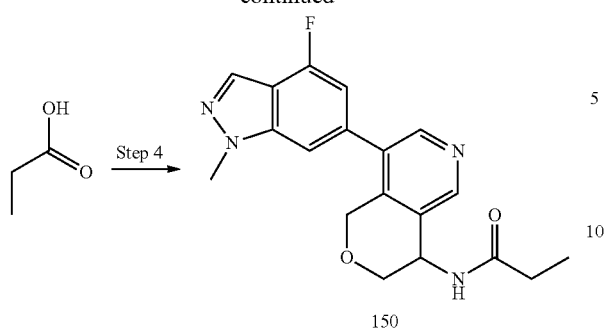

150

Compound 149 is prepared according to the procedures for Example 6 in Step 1 to Step 3.

Compound 149 (51 mg, 0.17 mmol), propionic acid (0.019 mL) and triethyl amine (0.071 mL, 0.51 mmol) are mixed in acetonitrile (2.0 mL). Then O-(benzotriazol-1-yl)-N,N,N',N'-tetramethyluronium tetrafluoroborate (66 mg, 0.21 mmol) is added and the mixture is stirred for 3 hr. The solvent is removed to give the crude product. Purification by flash column chromatography affords 32 mg of the title product.

Compounds 151 to 156 in Table 1 are synthesized according to the procedures for Example 7, substituting with either commercially available reagents or the appropriate intermediates listed below.

| Cpd No | Bromide for Boronic ester | Bromide |
|---|---|---|
| 151 | Commercial | Intermediate A9 |
| 152 | Commercial | Intermediate A10 |
| 153 | Commercial | Intermediate A10 |
| 154 | Commercial | Intermediate A10 |
| 155 | Commercial | Intermediate A9 |
| 156 | Commercial | Intermediate A9 |

Example 8: Synthesis of ethanesulfonic acid [8-(1-oxo-indan-5-yl)-3,4-dihydro-1H-pyrano[4,3-c]pyridin-4-yl]-amide, Enantiomer II (Cpd 157, Table 1)

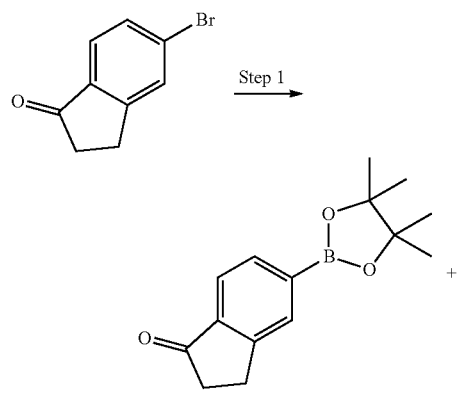

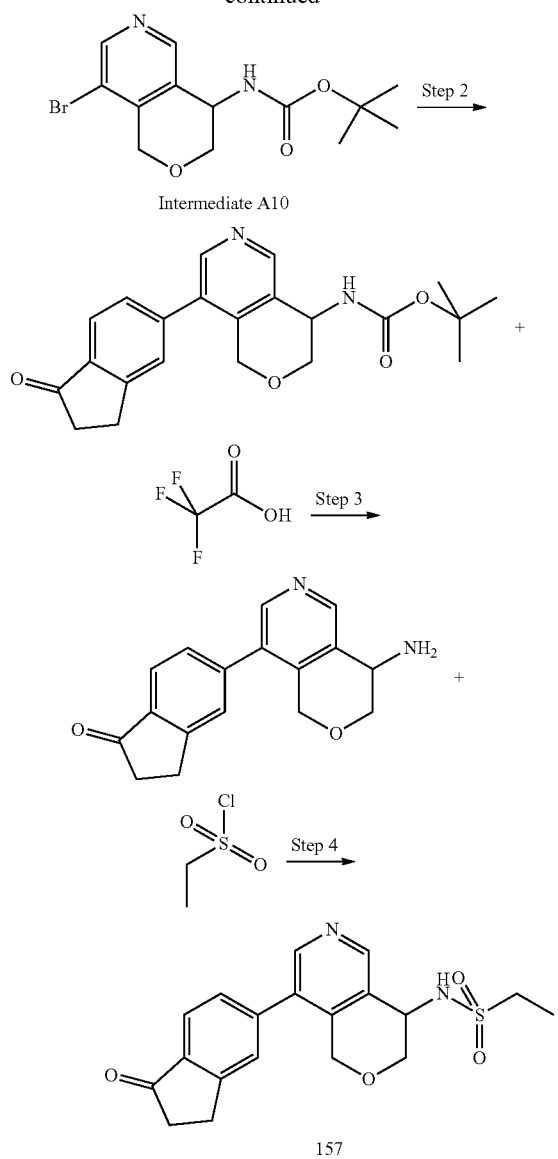

157

5-Bromo-indan-1-one and Intermediate A10 are converted to 5-(4-amino-3,4-dihydro-1H-pyrano[4,3-c]pyridin-8-yl)-indan-1-one according to the procedures for Example 6 in Step 1 to Step 3.

5-(4-Amino-3,4-dihydro-1H-pyrano[4,3-c]pyridin-8-yl)-indan-1-one (31 mg, 0.11 mmol) is dissolved in DCM (1.0 mL) and ethanesulfonyl chloride (0.012 mL, 0.12 mmol) is added followed by the addition of triethyl amine (0.031 mL, 0.22 mmol). The mixture is stirred for 1 hr and DCM (20 mL) is added along with saturated aqueous NaHCO$_3$ solution (10 mL) and water (15 mL). The mixture is stirred for 10 min and the aqueous layer is separated and extracted with DCM (2×20 mL). All the organic layers are combined and concentrated to give the crude product. Purification by flash column chromatography affords 17 mg of the title product.

Compound 158 and 159 in Table 1 are synthesized according to the procedures for Example 8, substituting with either commercially available reagents or the appropriate intermediates listed below.

| Cpd No | Bromide for Boronic ester | Bromide |
|---|---|---|
| 158 | Commercial | Intermediate A10 |
| 159 | Commercial | Intermediate A9 |

Example 9: Syntheses of 6-(4-hydroxy-3,4-dihydro-1H-pyrano[3,4-c]pyridin-5-yl)-3,4-dihydro-2H-[1,8]naphthyridine-1-Carboxylic Acid Amide and its Enantiomers (Cpd 160, 161 and 162, Table 1)

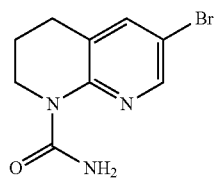

Intermediate B15

Step 1

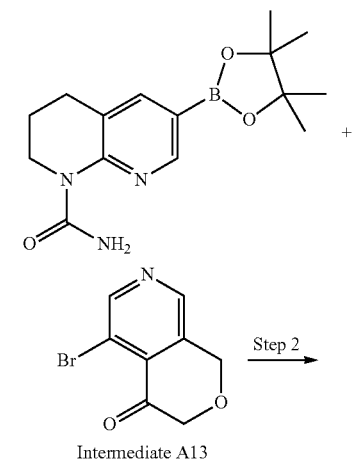

Intermediate A13

Step 2

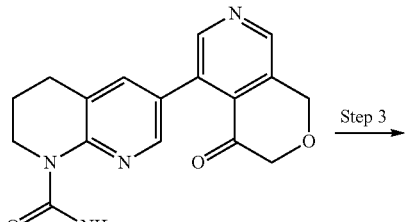

Step 3

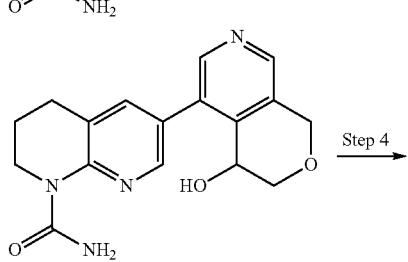

160

Step 4

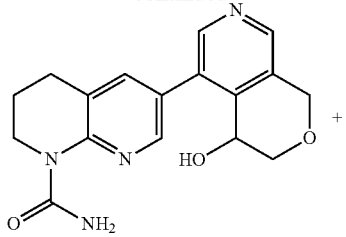

Enantiomer I
161

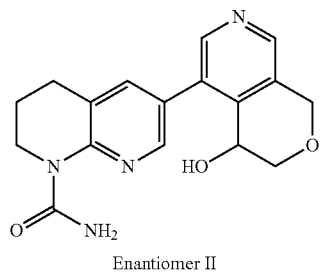

Enantiomer II
162

Intermediate B15 and Intermediate A13 are coupled to give 6-(4-oxo-3,4-dihydro-1H-pyrano[3,4-c]pyridin-5-yl)-3,4-dihydro-2H-[1,8]naphthyridine-1-carboxylic acid amide according to the procedures for Example 5 in Step 1 and Step 2.

6-(4-Oxo-3,4-dihydro-1H-pyrano[3,4-c]pyridin-5-yl)-3,4-dihydro-2H-[1,8]naphthyridine-1-carboxylic acid amide (110 mg, 0.33 mmol) is suspended in MeOH (26 mL) and sodium borohydride (250 mg, 6.6 mmol) is added. The mixture is stirred for 2 hr and saturated aqueous $NH_4Cl$ solution (40 mL) is added slowly. The mixture is extracted with EtOAc (4×125 mL) and the combined organic layers are dried and concentrated to give the crude product. Purification by flash column chromatography affords 86 mg of the racemic tilted product.

Chiral separation of the racemic 6-(4-hydroxy-3,4-dihydro-1H-pyrano[3,4-c]pyridin-5-yl)-3,4-dihydro-2H-[1,8]naphthyridine-1-carboxylic acid amide (81 mg) using Supercritical Fluid Chromatography affords 26 mg of Enantiomer I (Compound 161, 2.37 min) and 27 mg of Enantiomer II (Compound 162, 3.24 min). The retention times are measured using the following conditions: LUX 5u Cellulose 3 Analytical column, Mobile phase 25% (1:1:1 MeOH:iPA:EtOH+1% DEA):CO2 @ 3 mL/min, 40° C., 200 bars.

Compounds 165 to 168 in Table 1 are synthesized according to the procedures for Example 9, substituting Intermediate B15 with commercially available reagents.

The chiral separation of racemic material using Supercritical Fluid Chromatography affords Compound 165 (retention time, 1.76 min) and 166 (retention time, 2.42 min). The retention times are measured using the following conditions: LUX 5u Cellulose 1 Analytical column, Mobile phase 20% (1:1:1 MeOH:EtOH:IPA):CO2 @ 3 mL/min, 200 bar, 40° C.

The chiral separation of racemic material using Supercritical Fluid Chromatography affords Compound 167 (retention time, 4.21 min) and Compound 168 (retention time, 8.57). The retention times are measured using the following conditions: LUX 5u Cellulose 4 Analytical column, Mobile phase 20% (1:1:1 MeOH:EtOH:IPA):CO2 @ 3 mL/min, 200 bar, 40° C.

Example 10: Syntheses of Both Enantiomers of 6-(4-hydroxy-4-methyl-3,4-dihydro-1H-pyrano[4,3-c]pyridin-8-yl)-1-methyl-1H-indazole-4-carbonitrile (Cpd 173 and 174, Table 1)

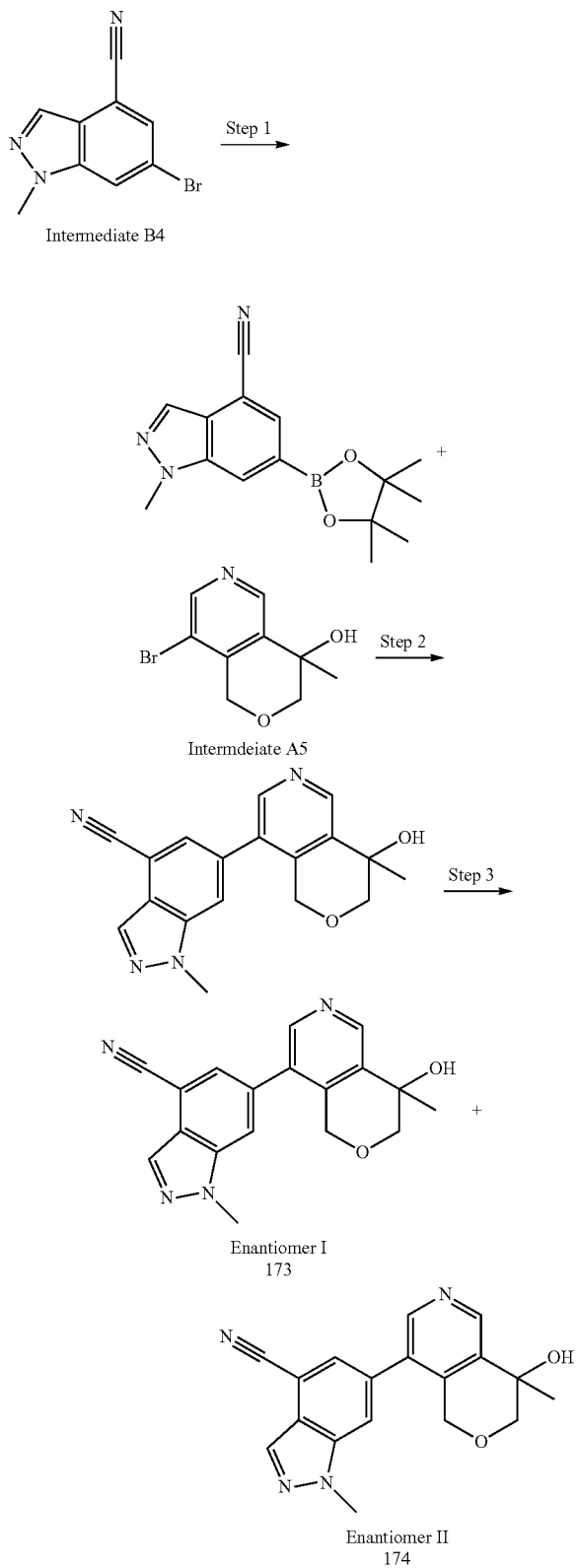

Intermediate B4 and Intermediate A5 are coupled to give racemic 6-(4-hydroxy-4-methyl-3,4-dihydro-1H-pyrano[4,3-c]pyridin-8-yl)-1-methyl-1H-indazole-4-carbonitrile according to the procedures for Example 5 in Step 1 and 2.

Chiral separation of the racemic 6-(4-hydroxy-4-methyl-3,4-dihydro-1H-pyrano[4,3-c]pyridin-8-yl)-1-methyl-1H-indazole-4-carbonitrile (126 mg) using Supercritical Fluid Chromatography affords 43 mg of Enantiomer I (Compound 173, 2.84 min) and 42 mg of Enantiomer II (Compound 174, 3.75 min). The retention times are measured using the following conditions: Regis RegisPack Analytical column, Mobile phase 12% (1:1:1 MeOH:iPA:EtOH):CO2 @ 3 mL/min, 40° C., 200 bars.

Compound 169 to 172 and Compound 175 to 178 in Table 1 are synthesized according to the procedures for Example 10, substituting Intermediate B4 with either commercially available reagents or the appropriate intermediates listed below.

| Cpd No | Bromide for Boronic ester | Bromide |
|---|---|---|
| 169 | commercial | Intermediate A5 |
| 170 | commercial | Intermediate A5 |
| 171 | Intermediate B14 | Intermediate A5 |
| 172 | Intermediate B14 | Intermediate A5 |
| 175 | Intermediate B5 | Intermediate A5 |
| 176 | Intermediate B5 | Intermediate A5 |
| 177 | Intermediate B3 | Intermediate A5 |
| 178 | Intermediate B3 | Intermediate A5 |

The chiral separation of racemic material using Supercritical Fluid Chromatography affords Compound 169 (retention time, 2.67 min) and 170 (retention time, 3.49 min). The retention times are measured using the following conditions: Regis RegisPack Analytical column, Mobile phase 20% (1:1:1 MeOH:EtOH:IPA):CO2 @ 3 mL/min, 200 bar, 40° C.

The chiral separation of racemic material using Supercritical Fluid Chromatography affords Compound 171 (retention time, 9.28 min) and 172 (retention time, 13.54 min). The retention times are measured using the following conditions: ES Chromega CC4 analytical column, Mobile phase 20% (1:1:1 MeOH:EtOH:IPA):CO2 @ 3 mL/min, 200 bar, 40° C.

The chiral separation of racemic material using Supercritical Fluid Chromatography affords Compound 176 (retention time, 3.83 min) and 175 (retention time, 5.53 min). The retention times are measured using the following conditions: Regis RegisPack Analytical column, Mobile phase 10% (1:1:1 MeOH:EtOH:IPA):CO2 @ 3 mL/min, 200 bar, 40° C.

The chiral separation of racemic material using Supercritical Fluid Chromatography affords Compound 177 (retention time, 4.79 min) and 178 (retention time, 7.93 min). The retention times are measured using the following conditions: ES Chromega CC4 analytical column, Mobile phase 20% (1:1:1 MeOH:EtOH:IPA):CO2 @ 3 mL/min, 200 bar, 40° C.

Example 11: Syntheses of Both Enantiomers of 4-methyl-5-(1-methyl-1H-indazol-6-yl)-3,4-dihydro-1H-pyrano[3,4-c]pyridin-4-ol (Cpd 179 and 180, Table 1)

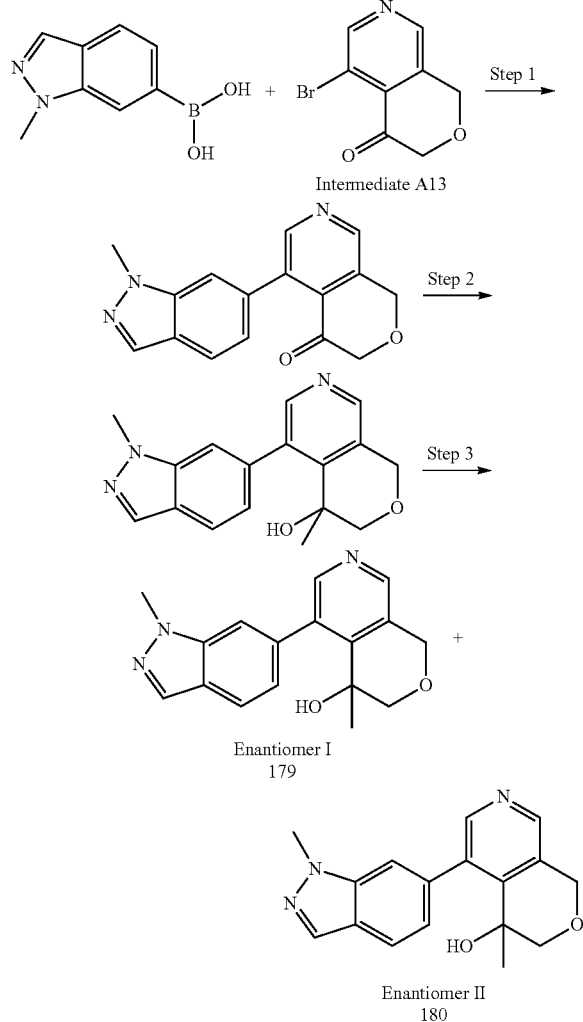

Intermediate A13 is coupled with (1-methylindazol-6-yl) boronic acid to give 5-(1-methyl-1H-indazol-6-yl)-1H-pyrano[3,4-c]pyridin-4-one according to the procedure for Example 1 in Step 1.

To a solution of 5-(1-methyl-1H-indazol-6-yl)-1H-pyrano[3,4-c]pyridin-4-one (110 mg, 0.39 mmol) in THF (5.0 mL) cooled at 0° C. is added 3.0 M methyl magnesium bromide solution (0.26 mL, 0.79 mmol). The reaction is stirred for 2 hr and allowed to warm to room temperature. Water is added and the mixture is extracted with EtAOc. The organic layer is separated and concentrated to give the crude product. Purification by flash column chromatography affords 30 mg of the racemic 4-methyl-5-(1-methyl-1H-indazol-6-yl)-3,4-dihydro-1H-pyrano[3,4-c]pyridin-4-ol.

Chiral separation of the racemic 4-methyl-5-(1-methyl-1H-indazol-6-yl)-3,4-dihydro-1H-pyrano[3,4-c]pyridin-4-ol (30 mg) using Supercritical Fluid Chromatography affords 9 mg of Enantiomer I (Compound 179, 2.70 min) and 8 mg of Enantiomer II (Compound 180, 4.47 min). The retention times are measured using the following conditions: LUX 5u Cellulose 3 Analytical column, Mobile phase 5% (1:1:1 MeOH:EtOH:IPA):CO2 @ 3 mL/min, 40° C., 200 bars.

Example 12: Synthesis of 2-(4-hydroxy-3,4-dihydro-1H-pyrano[4,3-c]pyridin-8-yl)-6,7-dihydro-[1]pyrindin-5-one, Enantiomer I (Cpd 181, Table 1)

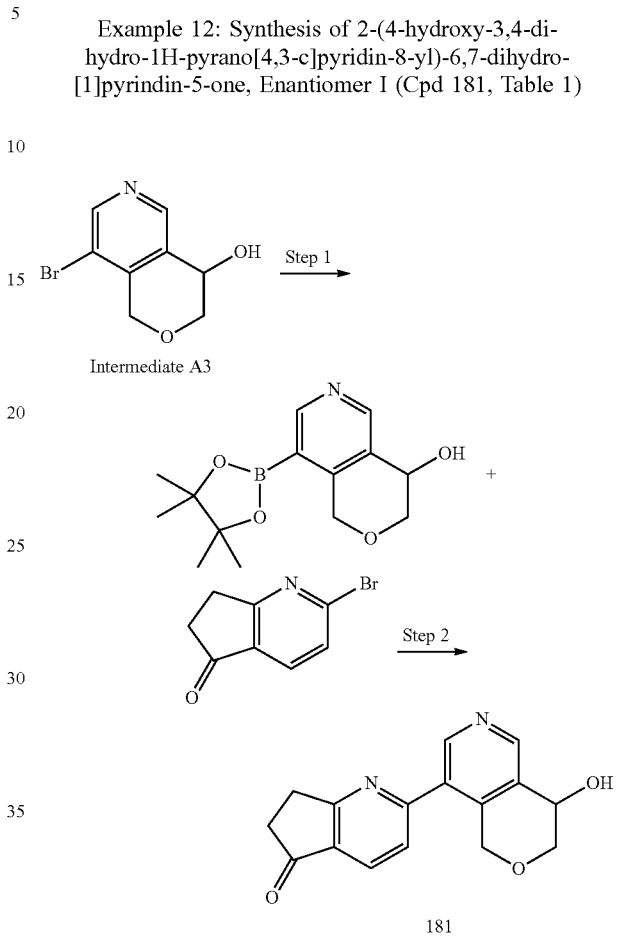

Intermediate A3 (40 mg, 0.17 mmol), bis(pinacolato)diboron (66 mg, 0.26 mmol), potassium acetate (68 mg, 0.70 mmol) and [1,1'-bis(diphenylphosphino)ferrocene)dichloropalladium(II) (13 mg, 0.017 mmol) are mixed in 1,4-dioxane (2.0 mL). The reaction mixture is heated at 120° C. under Argon for 18 hr. After the mixture is cooled down to room temperature, it is used in the next step without workup or purification.

2-Bromo-6,7-dihydro-[1]pyrindin-5-one (31 mg, 0.15 mmol), 2.0 M Na$_2$CO$_3$ aqueous solution (0.22 mL, 0.44 mmol), [1,1'-bis(diphenylphosphino)ferrocene)dichloropalladium(II) (5.3 mg, 0.007 mmol) and 1.0 mL of 1,4-dioxane are added into the reaction crude obtained from the previous step. The mixture is then heated at 100° C. under Argon for 4 hr. After cooling down to room temperature, the mixture is concentrated and the residue is diluted with EtOAc. The organic layer is washed with water, brine, dried over Na$_2$SO$_4$ and concentrated to give the crude product. Purification by flash column chromatography affords 18 mg of the title product.

Compound 182 in Table 1 is synthesized according to the procedures for Example 12, substituting 2-bromo-6,7-dihydro-[1]pyrindin-5-one with commercially available reagent.

Example 13: Synthesis of Ethanesulfonic Acid [8-(1-hydroxy-indan-5-yl)-3,4-dihydro-1H-pyrano[4,3-c]pyridin-4-yl]-amide, Mixture of Diastereomers (Cpd 184, Table 1)

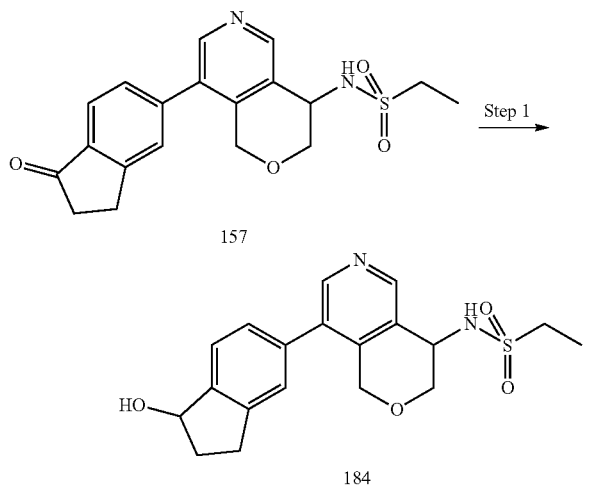

Compound 157 (18 mg, 0.048 mmol) is dissolved in MeOH (1.0 mL) and sodium borohydride (10 mg, 0.26 mmol) is added. The mixture is stirred for 1 hr and the solvent is removed. Then saturated aqueous NH$_4$Cl solution (5.0 mL) is added along with water (5.0 mL) and EtOAc (15 mL). The mixture is stirred for 10 min and the aqueous layer is separated and extracted with EtOAc (2×10 mL). The organic layers are combined and concentrated to give the crude product. Purification by flash column chromatography affords 15 mg of the title product.

Example 14: Synthesis of dimethyl-[8-(1-methyl-1H-indazol-6-yl)-3,4-dihydro-1H-pyrano[4,3-c]pyridin-4-yl]-amine, Enantiomer II (Cpd 185, Table 1)

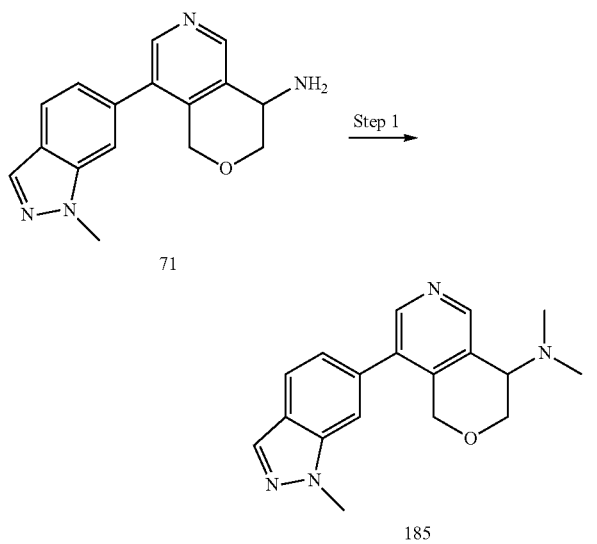

To a solution of Compound 71 (31 mg, 0.11 mmol) in MeOH (1.0 mL) are added 37% formaldehyde aqueous solution (33 mg, 1.1 mmol) and sodium cyanoborohydride (35 mg, 0.55 mmol). The reaction mixture is stirred at room temperature for 3 hr and the solvent is removed to give the crude product. Purification by flash column chromatography affords 10 mg of the title product.

Example 15: Synthesis of 4-(4-hydroxy-3,4-dihydro-1H-pyrano[4,3-c]pyridin-8-yl)-cyclohex-3-enecarbonitrile, Enantiomer I (Cpd 186, Table 1)

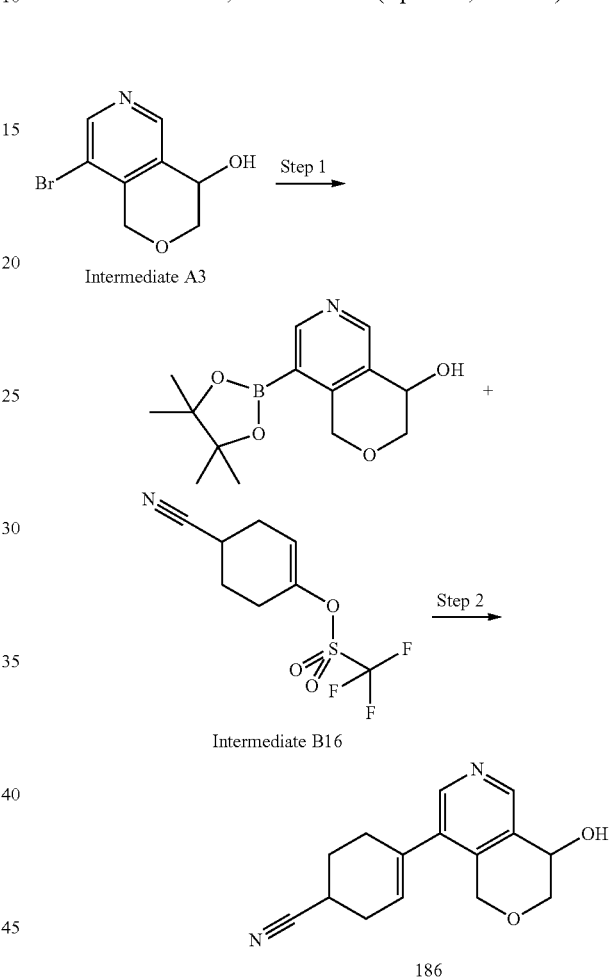

Intermediate A3 is converted to 8-(4,4,5,5-tetramethyl-[1,3,2]dioxaborolan-2-yl)-3,4-dihydro-1H-pyrano[4,3-c]pyridin-4-ol according to the procedure for Step 1 in Example 12.

Intermediate B16 (94 mg, 0.37 mmol), 3.0 M Na$_2$CO$_3$ aqueous solution (0.1 mL, 0.30 mmol) and [1,1'-bis(diphenylphosphino)ferrocene)dichloropalladium(II) (27 mg, 0.037 mmol) are added into the crude 8-(4,4,5,5-tetramethyl-[1,3,2]dioxaborolan-2-yl)-3,4-dihydro-1H-pyrano[4,3-c]pyridin-4-ol (0.37 mmol) obtained from the previous step. The mixture is heated at 90° C. for 18 hr before it is concentrated to give the crude product. Purification by flash column chromatography affords 30 mg of the titled product.

Compound 187, 189 and 192 in Table 1 are synthesized according to the procedures for Example 15, substituting Intermediate A3 and Intermediate B16 with the appropriate intermediates listed below.

| Cpd No | Bromide for Boronic ester | Triflate |
|---|---|---|
| 187 | Intermediate A4 | Intermediate B17 |
| 189 | Intermediate A3 | Intermediate B17 |
| 192 | Intermediate A4 | Intermdeiate B16 |

Example 16: Syntheses of Diastereomers of 8-(1-methyl-4,5,6,7-tetrahydro-1H-indazol-6-yl)-3,4-dihydro-1H-pyrano[4,3-c]pyridin-4-ol (Cpd 190 and 191, Table 1)

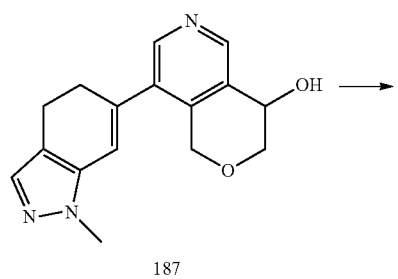

187

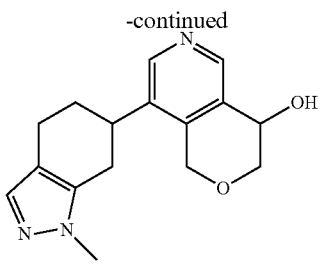

Diastereomer I
190

+

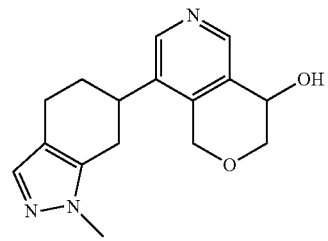

Diastereomer II
191

To the solution of Compound 187 (50 mg, 0.18 mmol) in EtOH (3.0 mL) are added ammonium formate (50 mg, 0.79 mmol) and 10% Pd on activated carbon (28 mg, 0.026 mmol). The mixture is stirred at 90° C. for 30 hrs before it is filtered and concentrated. The residue is dissolved in EtOAc (15 mL) and it is washed with water (2×10 mL). The organic layer is dried and concentrated to give the crude products. Purification by flash column chromatography affords 8 mg of Compound 190 and 7 mg of Compound 191.

LCMS Data for Compounds in Table 1 are shown in Table 2, which are measured using the methods set forth in the following Table.

| | | | LC Methods | | | | |
|---|---|---|---|---|---|---|---|
| | | Mobile | Gradient | | | Flow | |
| Method | Mobile Phase A | Phase B | Time (min) | % A | % B | (mL/min.) | Column |
| A | 0.1% Formic Acid in Water | 0.1% Formic Acid in Acetonitrile | 0<br>0.5<br>1.5<br>2.5<br>3.3<br>4.0 | 90.0<br>90.0<br>1.0<br>1.0<br>90.0<br>90.0 | 10.0<br>10.0<br>99.0<br>99.0<br>10.0<br>10.0 | 0.5 | Thermo Scientific, Aquasil C18, 50 × 2.1 mm, 5μ |
| B | 0.1% Formic Acid in Water | 0.1% Formic Acid in Acetonitrile | 0<br>1.0<br>1.3<br>1.4<br>1.7 | 95<br>5<br>5<br>95<br>95 | 5<br>95<br>95<br>5<br>5 | 0.8 | BEH 2.5 × 50 mm C18, 1.7 μm particle diameter |
| C | 5% Acetonitrile in 2.5 mM aqueous Ammonium Bicarbonate | 100% Acetonitrile | 0<br>1.19<br>1.77<br>1.78 | 90.0<br>5.0<br>5.0<br>90.0 | 10.0<br>95.0<br>95.0<br>10.0 | 0.8 | BEH 2.1 × 50 mm C18, 1.7 μm particle diameter |
| D | 5% Acetonitrile in 2.5 mM aqueous Ammonium Bicarbonate | 100% Acetonitrile | 90% A to 100% B in 1.19 minutes hold at 100% B to 1.70 minutes | | | 0.8 | BEH 2.1 × 50 mm C18, 1.7 um particle diameter |
| E | 95% Water 5% Acetonitrile 0.05% Formic Acid | 0.05% Formic Acid in Acetonitrile | 90% A to 100% B in 1.19 minutes hold at 100% B to 1.70 minutes | | | 0.8 | CSH 2.1 × 50 mm C18, 1.7 um particle diameter |

| Method | Mobile Phase A | Mobile Phase B | Gradient Time (min) | % A | % B | Flow (mL/min.) | Column |
|---|---|---|---|---|---|---|---|
| F | 95% Water 5% Acetonitrile 0.05% Formic Acid | 0.05% Formic Acid in Acetonitrile | 95% A to 100% B in 3.65 minutes, hold at 100% B to 4.95 minutes | | | 0.6 | HSS T3 2.1 × 100 mm C18, 1.8 um particle diameter |

TABLE 2

| Cpd No. | Mass Found | Retention Time (min) | LC Method |
|---|---|---|---|
| 1 | 296.7 | 0.28 | A |
| 2 | 296.7 | 0.27 | A |
| 3 | 227.1 | 0.45 | B |
| 4 | 252.6 | 1.72 | A |
| 5 | 227.1 | 0.46 | B |
| 6 | 252.5 | 1.72 | A |
| 7 | 286.1 | 0.56 | B |
| 8 | 292.9 | 1.24 | A |
| 9 | 291.3 | 2.69 | A |
| 10 | 281.7 | 0.97 | A |
| 11 | 281.1 | 0.49 | B |
| 12 | 281.1 | 0.43 | B |
| 13 | 281.1 | 0.49 | B |
| 14 | 282.7 | 0.97 | A |
| 15 | 299.1 | 0.54 | B |
| 16 | 307.1 | 0.69 | B |
| 17 | 307.1 | 0.78 | B |
| 18 | 299.1 | 0.55 | B |
| 19 | 299.1 | 0.55 | B |
| 20 | 285.1 | 1.19 | A |
| 21 | 267.2 | 1.19 | A |
| 22 | 278.8 | 1.23 | A |
| 23 | 282.1 | 1.19 | A |
| 24 | 268.3 | 1.2 | A |
| 25 | 286.2 | 1.2 | A |
| 26 | 260.2 | 1.19 | A |
| 27 | 268.3 | 1.2 | A |
| 28 | 300.2 | 1.19 | A |
| 29 | 281.7 | 1.2 | A |
| 30 | 279.2 | 1.2 | A |
| 31 | 267.2 | 1.19 | A |
| 32 | 232.3 | 1.19 | A |
| 33 | 285.1 | 1.19 | A |
| 34 | 267.2 | 1.2 | A |
| 35 | 279.3 | 1.2 | A |
| 36 | 282.2 | 1.19 | A |
| 37 | 268.3 | 1.2 | A |
| 38 | 286.2 | 1.2 | A |
| 39 | 260.2 | 1.2 | A |
| 40 | 268.3 | 1.21 | A |
| 41 | 246.2 | 1.18 | A |
| 42 | 299.1 | 0.6 | B |
| 43 | 299.1 | 0.5 | B |
| 44 | 281.6 | 1.2 | A |
| 45 | 279.2 | 1.2 | A |
| 46 | 257.7 | 1.21 | A |
| 47 | 267.7 | 1.21 | A |
| 48 | 267.2 | 1.19 | A |
| 49 | 268.1 | 0.47 | B |
| 50 | 281.1 | 0.46 | B |
| 51 | 296.1 | 0.45 | B |
| 52 | 282.1 | 0.39 | B |
| 53 | 268.1 | 0.47 | B |
| 54 | 296.1 | 0.45 | B |
| 55 | 299.1 | 0.56 | B |
| 56 | 323.1 | 0.52 | B |
| 57 | 336.2 | 0.39 | B |
| 58 | 351.2 | 0.49 | B |
| 59 | 337.1 | 0.44 | B |
| 60 | 337.2 | 0.51 | B |
| 61 | 336.2 | 0.5 | B |
| 62 | 336.2 | 0.55 | B |
| 63 | 387.1 | 0.53 | B |
| 64 | 373.1 | 0.48 | B |
| 65 | 373.1 | 0.55 | B |
| 66 | 372.1 | 0.59 | B |
| 67 | 373.2 | 0.49 | C |
| 68 | 391.3 | 1.01 | A |
| 69 | 373.3 | 0.96 | A |
| 70 | 294.1 | 0.46 | B |
| 71 | 281.3 | 1.27 | A |
| 72 | 336.2 | 0.47 | B |
| 73 | 336.2 | 0.47 | B |
| 74 | 323.3 | 1.3 | A |
| 75 | 349.3 | 1.3 | A |
| 76 | 336.7 | 1.33 | A |
| 77 | 350.2 | 0.59 | B |
| 78 | 387.2 | 0.65 | E |
| 79 | 386.8 | 2.07 | A |
| 80 | 358.1 | 0.5 | B |
| 81 | 358.1 | 0.5 | B |
| 82 | 372.1 | 0.51 | B |
| 83 | 372.1 | 0.57 | B |
| 84 | 323.3 | 1.14 | A |
| 85 | 323.3 | 1.14 | A |
| 86 | 281.7 | 1.29 | A |
| 87 | 281.7 | 1.27 | A |
| 88 | 307.7 | 0.21 | A |
| 89 | 307.1 | 0.36 | B |
| 90 | 282.1 | 0.5 | B |
| 91 | 309.2 | 0.38 | D |
| 92 | 326.3 | 1 | A |
| 93 | 308.1 | 0.4 | B |
| 94 | 282.1 | 0.5 | B |
| 95 | 282.1 | 0.33 | B |
| 96 | 299.1 | 0.52 | B |
| 97 | 282.1 | 0.33 | B |
| 98 | 268.6 | 0.27 | A |
| 99 | 267.7 | 0.23 | A |
| 100 | 268.6 | 0.27 | A |
| 101 | 267.7 | 0.27 | A |
| 102 | 326.1 | 0.38 | B |
| 103 | 281.7 | 1.69 | A |
| 104 | 321.7 | 1.17 | A |
| 105 | 321.1 | 0.4 | B |
| 106 | 307.2 | 0.53 | E |
| 107 | 299.1 | 0.45 | B |
| 108 | 299.1 | 0.45 | B |
| 109 | 310.1 | 0.45 | B |
| 110 | 295.1 | 0.49 | B |
| 111 | 326.3 | 1.27 | A |
| 112 | 326.3 | 1.26 | A |
| 113 | 306.1 | 0.58 | B |
| 114 | 308.1 | 0.63 | B |
| 115 | 295.1 | 0.5 | B |
| 116 | 295.1 | 0.5 | B |
| 117 | 295.1 | 0.5 | B |
| 118 | 295.1 | 0.5 | B |
| 119 | 296.1 | 0.38 | B |
| 120 | 296.7 | 1.18 | A |

TABLE 2-continued

| Cpd No. | Mass Found | Retention Time (min) | LC Method |
|---|---|---|---|
| 121 | 296.7 | 1.17 | A |
| 122 | 297.1 | 0.46 | B |
| 123 | 297.1 | 0.45 | B |
| 124 | 310.1 | 0.41 | B |
| 125 | 296.1 | 1.19 | A |
| 126 | 295.6 | 1.25 | A |
| 127 | 302.1 | 0.97 | A |
| 128 | 357.3 | 1.02 | A |
| 129 | 393.2 | 1 | A |
| 130 | 302.1 | 0.97 | A |
| 131 | 300.3 | 0.96 | A |
| 132 | 355.2 | 0.95 | A |
| 133 | 391.3 | 0.96 | A |
| 134 | 300.2 | 0.96 | A |
| 135 | 355.2 | 0.95 | A |
| 136 | 391.2 | 0.96 | A |
| 137 | 314.3 | 0.95 | A |
| 138 | 314.3 | 0.96 | A |
| 139 | 314.3 | 0.95 | A |
| 140 | 314.3 | 0.96 | A |
| 141 | 320.2 | 1 | A |
| 142 | 320.2 | 1 | A |
| 143 | 375.4 | 1.05 | A |
| 144 | 411.3 | 1.03 | A |
| 145 | 313.1 | 0.36 | C |
| 146 | 313.1 | 0.36 | C |
| 147 | 368.3 | 0.96 | A |
| 148 | 334.3 | 1 | A |
| 149 | 298.1 | 0.48 | B |
| 150 | 354.1 | 0.59 | B |
| 151 | 322.1 | 0.46 | B |
| 152 | 322.1 | 0.46 | B |
| 153 | 380.7 | 1.17 | A |
| 154 | 336.1 | 0.45 | B |
| 155 | 336.2 | 0.52 | B |
| 156 | 337.1 | 0.63 | B |
| 157 | 372.1 | 0.55 | B |
| 158 | 387.2 | 1.28 | A |
| 159 | 373.1 | 0.68 | B |
| 160 | 326.7 | 1.64 | A |
| 161 | 326.1 | 0.38 | B |
| 162 | 326.1 | 0.38 | B |
| 163 | 327.4 | 1.6 | A |
| 164 | 327.4 | 1.6 | A |
| 165 | 281.1 | 0.45 | B |
| 166 | 281.6 | 1.29 | A |
| 167 | 278.1 | 0.57 | B |
| 168 | 278.1 | 0.8 | B |
| 169 | 296.2 | 1.26 | A |
| 170 | 296.2 | 1.26 | A |
| 171 | 313.1 | 0.59 | B |
| 172 | 313.1 | 0.6 | B |
| 173 | 320.1 | 0.58 | B |
| 174 | 320.1 | 0.58 | B |
| 175 | 313.1 | 0.59 | B |
| 176 | 313.1 | 0.59 | B |
| 177 | 320.1 | 0.64 | B |
| 178 | 320.1 | 0.64 | B |
| 179 | 295.1 | 0.46 | B |
| 180 | 295.1 | 0.46 | B |
| 181 | 283.2 | 1.16 | A |
| 182 | 297.1 | 0.58 | B |
| 183 | 281.7 | 1.12 | A |
| 184 | 374.1 | 0.51 | B |
| 185 | 309.3 | 1.26 | A |
| 186 | 256.1 | 0.42 | B |
| 187 | 283.7 | 1.12 | A |
| 188 | 283.0 | 0.30 | E |
| 189 | 284.4 | 0.35 | E |
| 190 | 286.3 | 0.91 | F |
| 191 | 286.3 | 0.83 | F |
| 192 | 257.5 | 0.26 | E |
| 193 | 355.2 | 0.63 | C |
| 194 | 375.2 | 0.73 | C |
| 195 | 391.2 | 0.66 | C |
| 196 | 411.2 | 0.76 | C |
| 197 | 309.3 | 0.52 | C |
| 198 | 309.3 | 0.52 | C |
| 199 | 320.4 | 1.92 | A |
| 200 | 320.4 | 1.92 | A |

Assessment of Biological Activity

Inhibition of Aldosterone Synthase

The compounds of the invention may be evaluated for aldosterone synthase inhibition by the following assay:

The aldosterone synthase inhibition assay employs cynomolgus adrenal gland mitochondria as the source of aldosterone synthase (CYP11B2). Mitochondria are prepared from frozen cynomolgus monkey adrenal glands according to Method A described in by J. D. McGarry et al. (Biochem. J., 1983, 214, 21-28), with a final resuspension in the AT buffer described in R. Yamaguchi et al. (Cell Death and Differentiation, 2007, 14, 616-624), frozen as aliquots in liquid nitrogen and stored at −80° C. until use.

Assays are performed in 96-well format in a final volume of 60 μL/well, containing 100 mM potassium phosphate, pH 7.4, 1% (v/v) DMSO, and additionally, 2 μM of corticosterone and 6 mg of mitochondrial protein. Reactions are started by the addition of NADPH to 1 mM and allowed to proceed for 60-90 minutes at 37° C. Reactions are terminated by the addition of 60 of acetonitrile. One hundred microliters are then transferred to a glass filter plate and centrifuged at 570×g for 5 minutes and the filtrate is collected. Reaction product aldosterone is quantified by mass spectrometry. To determine the assay blank value (0% activity), NADPH is omitted from some reactions.

Dose dependent inhibition is quantified by the inclusion of compound at various concentrations. Maximum activity (100%) is defined by reactions containing NADPH, but without compound. Activities at each concentration are expressed as a percentage of the maximum activity (y-axis) and plotted against concentration of compound (x-axis) and the concentration corresponding to 50% activity (IC50) determined using the XLFit curve-fitting program using a 4-parameter logistic model.

Representative compounds of the present invention were tested for activity in the above assay. Preferred compounds have an $IC_{50}<1,000$ nM and more preferred compounds have an $IC_{50}<100$ nM in this assay. As examples, data for representative compounds from Table 1 are shown in Table 3.

TABLE 3

| Cpd No. | $IC_{50}$ (nM) |
|---|---|
| 1 | 28.9 |
| 2 | 100.7 |
| 3 | 483.7 |
| 4 | 42 |
| 5 | 55 |
| 6 | 9.8 |
| 7 | 6.1 |
| 8 | 3700 |
| 9 | 5.7 |
| 10 | 114.9 |
| 11 | 689.6 |
| 12 | 21 |
| 13 | 81 |
| 14 | 15.7 |

TABLE 3-continued

| Cpd No. | IC$_{50}$ (nM) |
|---|---|
| 15 | 7.8 |
| 16 | 12.5 |
| 17 | 8 |
| 18 | 20.1 |
| 19 | 153 |
| 20 | 681.2 |
| 21 | 194.9 |
| 22 | 64.1 |
| 23 | 194.9 |
| 24 | 480 |
| 25 | 158.7 |
| 26 | 1500 |
| 27 | 1300 |
| 28 | 333.2 |
| 29 | 48.6 |
| 30 | 54 |
| 31 | 159.7 |
| 32 | 2700 |
| 33 | 40.5 |
| 34 | 17.3 |
| 35 | 9.7 |
| 36 | 17.5 |
| 37 | 94.4 |
| 38 | 12 |
| 39 | 437.5 |
| 40 | 185.7 |
| 41 | 1000 |
| 42 | 367.4 |
| 43 | 22 |
| 44 | 8.5 |
| 45 | 5.8 |
| 46 | 301.7 |
| 47 | 50 |
| 48 | 17.4 |
| 49 | 55.7 |
| 50 | 1200 |
| 51 | 24.2 |
| 52 | 64.1 |
| 53 | 807.8 |
| 54 | 148.7 |
| 55 | 7.6 |
| 56 | 85.8 |
| 57 | 219.1 |
| 58 | 129.6 |
| 59 | 178.9 |
| 60 | 75.5 |
| 61 | 36.2 |
| 62 | 138.6 |
| 63 | 85.2 |
| 64 | 610.8 |
| 65 | 36.1 |
| 66 | 1000 |
| 67 | 109.7 |
| 68 | 15.9 |
| 69 | 84.6 |
| 70 | 166.1 |
| 71 | 22.2 |
| 72 | 2300 |
| 73 | 34.6 |
| 74 | 25.6 |
| 75 | 26.4 |
| 76 | 17.9 |
| 77 | 32.6 |
| 78 | 2800 |
| 79 | 652.7 |
| 80 | 2100 |
| 81 | 28.5 |
| 82 | 215.4 |
| 83 | 31.3 |
| 84 | 255 |
| 85 | 90.9 |
| 86 | 494.4 |
| 87 | 123.3 |
| 88 | 128.5 |
| 89 | 73 |
| 90 | 8.5 |
| 91 | 220.5 |
| 92 | 11.5 |
| 93 | 271.3 |
| 94 | 10.1 |
| 95 | 766.4 |
| 96 | 8.1 |
| 97 | 204.9 |
| 98 | 1300 |
| 99 | 5000 |
| 100 | 2300 |
| 101 | 224.9 |
| 102 | 64.9 |
| 103 | 10 |
| 104 | 81 |
| 105 | 51.1 |
| 106 | 599 |
| 107 | 79.9 |
| 108 | 771.4 |
| 109 | 544.4 |
| 110 | 13 |
| 111 | 114 |
| 112 | 40.9 |
| 113 | 14.5 |
| 114 | 18.8 |
| 115 | 579.7 |
| 116 | 26.3 |
| 117 | 103.2 |
| 118 | 12.5 |
| 119 | 960 |
| 120 | 789.9 |
| 121 | 95 |
| 122 | 193.6 |
| 123 | 16.3 |
| 124 | 1006.8 |
| 125 | 22.8 |
| 126 | 14 |
| 127 | 6.7 |
| 128 | 11.2 |
| 129 | 45.9 |
| 130 | 238.1 |
| 131 | 1469.7 |
| 132 | 518.1 |
| 133 | 1469.7 |
| 134 | 252.6 |
| 135 | 340.7 |
| 136 | 10000 |
| 137 | 1873.5 |
| 138 | 1555.6 |
| 139 | 2800 |
| 140 | 12000 |
| 141 | 339.4 |
| 142 | 117.7 |
| 143 | 27.9 |
| 144 | 470.1 |
| 145 | 737.7 |
| 146 | 9726.3 |
| 147 | 1688.2 |
| 148 | 83.7 |
| 149 | 17.3 |
| 150 | 17.4 |
| 151 | 4875.5 |
| 152 | 50.2 |
| 153 | 70 |
| 154 | 26.3 |
| 155 | 3800 |
| 156 | 311.8 |
| 157 | 46 |
| 158 | 13 |
| 159 | 797.5 |
| 160 | 51.1 |
| 161 | 35.3 |
| 162 | 71.4 |
| 163 | 44.3 |
| 164 | 41.5 |
| 165 | 223.6 |
| 166 | 36.5 |
| 167 | 155.6 |
| 168 | 40.5 |
| 169 | 13.9 |
| 170 | 7.8 |

TABLE 3-continued

| Cpd No. | IC$_{50}$ (nM) |
| --- | --- |
| 171 | 19.1 |
| 172 | 10.2 |
| 173 | 340 |
| 174 | 4400 |
| 175 | 21.6 |
| 176 | 13.4 |
| 177 | 42.8 |
| 178 | 15 |
| 179 | 38.9 |
| 180 | 281.4 |
| 181 | 149.7 |
| 182 | 496 |
| 183 | 52 |
| 184 | 124.1 |
| 185 | 18 |
| 186 | 67 |
| 187 | 12.9 |
| 188 | 21 |
| 189 | 67 |
| 190 | 340 |
| 191 | 48 |
| 192 | 14 |
| 193 | 38 |
| 194 | 38 |
| 195 | 140 |
| 196 | 330 |
| 197 | 18 |
| 198 | 19 |
| 199 | 22 |
| 200 | 279 |

Methods of Therapeutic Use

In accordance with the invention, there are provided novel methods of using the compounds of formula (I). The compounds disclosed herein effectively inhibit aldosterone synthase. The inhibition of aldosterone synthase is an attractive means for preventing and treating a variety of diseases or conditions that can be alleviated by lowering levels of aldosterone. Thus, the compounds are useful for the treatment of diseases and conditions as described in the Background section, including the following conditions and diseases:

Diabetic kidney disease including diabetic nephropathy;

Non-diabetic kidney disease including glomerulosclerosis, glomerulonephritis, IGA nephropathy, nephritic syndrome and focal segmental glomerulosclerosis (FSGS);

Cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism;

Adrenal hyperplasia and primary and secondary hyperaldosteronism.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of formula IA or IB

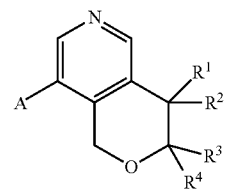

IA

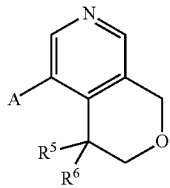

wherein:
A is selected from the group consisting of
benzoimidazolyl, benzo[d]isoxazolyl, benzooxazolyl, benzothiazolyl, benzotriazolyl, chromanyl, chromenyl, cyclohexen-1-yl, 2,3-dihydro-benzo[1,4]dioxinyl, 2,3-dihydro-5H-benzo[e][1,4]dioxepinyl, 3,4-dihydro-2H-benzo[b][1,4]dioxepinyl, 3,4-dihydro-2H-benzo[f][1,4]oxazepin-5-onyl, 2,3-dihydro-benzofuranyl, 4,5-dihydro-1H-indazolyl, 1,3-dihydroindol-2-onyl, 1,3-dihydro-isoindolyl, 3,4-dihydro-2H-isoquinolin-1-onyl, 3,4-dihydro-2H-naphthalen-1-onyl, 3,4-dihydro-2H-[1,8]napthyridinyl, 7,8-dihydro-5H-pyrano[4,3-b]pyridinyl, 6,7-dihydro-[1]pyridin-5-onyl, 3,4-dihydro-1H-quinolin-2-onyl, imidazo[1,2-a]pyridinyl, imidazo[1,5-a]pyridinyl, indanyl, indazolyl, indolyl, isochromanyl, isoquinolinyl, phenyl, pyrazolyl, pyrrolo[2,3-b]pyridinyl, quinolinyl, 1,3,4,5-tetrahydro-benzo[c]oxepinyl, 4, 5, 6, 7-tetrahydroindazolyl, thiazolyl and [1,2,4]triazolo[4,3-a]pyridinyl;
wherein A is optionally substituted with one to three groups selected from $C_{1-6}$alkyl, $C_{3-5}$cycloalkyl, —OH, oxo, $C_{1-6}$alkoxy, halogen, —CF$_3$, —CN, —C(O)C$_{1-3}$alkyl and —C(O)NH$_2$;
$R^1$ is selected from H and —C$_{1-3}$alkyl;
$R^2$ is selected from —OH, —CN, —NH$_2$, —N(C$_{1-3}$alkyl)$_2$, —NHC(O)C$_{1-3}$alkyl, —NHC(O)C$_{3-5}$cycloalkyl, —NHSO$_2$C$_{1-3}$alkyl and —NHC(O)CH$_2$C(CH$_3$)$_2$—OH;
$R^3$ is H;
$R^4$ is H; or
$R^3$ and $R^4$ together form a spiro cyclopropyl group;
$R^5$ is H or —C$_{1-3}$alkyl; and
$R^6$ is —OH;
or a salt thereof.

2. The compound of the formula IA according to claim 1, or a salt thereof.

3. The compounds of the formula IB according to claim 1, wherein
A is selected from the group consisting of benzo[d]isoxazol-5-yl, benzotriazol-5-yl, chromen-6- or -7-yl, cyclohexen-1-yl, 4,5-dihydro-1H-indazol-6-yl, 3,4-dihydro-2H-[1,8]napthyridin-6-yl, imidazo[1,5-a]pyridine-6-yl, indan-5-yl, indazol-5- or -6-yl, isochroman-7-yl, 2,3-dihydro-benzo[1,4]dioxin-6-yl, 3,4-dihydro-2H-benzo[b][1,4]dioxepin-7-yl, 2,3-dihydro-5H-benzo[e][1,4]dioxepin-7-yl, 3,4-dihydro-2H-naphthalen-1-on-6- or -7-yl, chroman-6- or -7-yl, 1,3,4,5-tetrahydrobenzo[c]oxepin-8-yl and 4, 5, 6, 7-tetrahydroindazol-6-yl;
$R^5$ is H or —CH$_3$; and
$R^6$ is OH;
or a salt thereof.

4. The compound of the formula IA according to claim 1, wherein
A is selected from the group consisting of benzoimidazol-5-yl, benzo[d]isoxazol-5-yl, benzooxazol-5-yl, benzothiazol-5-yl, benzotriazol-5-yl, chroman-6- or -7-yl, chromen-6- or -7-yl, cyclohexen-1-yl, 2,3-dihydrobenzo[1,4]dioxin-6-yl, 2,3-dihydro-5H-benzo[e][1,4]dioxepin-7-yl, 3,4-dihydro-2H-benzo[b][1,4]dioxepin-7-yl, 4,5-dihydro-1H-indazol-6-yl, 1,3-dihydroindol-2-on-5-yl, 3,4-dihydro-2H-isoquinolin-1-on-6-yl, 3,4-dihydro-2H-naphthalen-1-on-6- or -7-yl, 3,4-dihydro-2H-[1,8]napthyridin-6-yl, 3,4-dihydro-1H-quinolin-2-on-6-yl, imidazo[1,2-a]pyridine-7-yl, imidazo[1,5-a]pyridine-6-yl, indan-5-yl, indazol-5- or -6-yl, isochroman-7-yl, isoquinolin-6-yl, phenyl, quinolin-3- or -6-yl and 4, 5, 6, 7-tetrahydroindazol-6-yl, indol-5 or 6-yl, 1,3,4,5-tetrahydro-benzo[c]oxepin-8-yl;
wherein A is optionally substituted with one to three groups selected from $C_{1-3}$alkyl, $C_{3-5}$cycloalkyl, —OH, oxo, $C_{1-3}$alkoxy, Cl, F, —CF$_3$, —CN, —C(O)CH$_3$ and —C(O)NH$_2$;
$R^1$ is selected from H and —CH$_3$; and
$R^2$ is selected from —OH, —CN, —NH$_2$, —N(CH$_3$)$_2$, —NHC(O)C$_{1-3}$alkyl, —NHC(O)cyclopropyl, —NHSO$_2$C$_{1-3}$alkyl and —NHC(O)CH$_2$C(CH$_3$)$_2$—OH;
or a salt thereof.

5. The compound of the formula IA according to claim 1, wherein
A is selected from the group consisting of benzo[d]isoxazol-5-yl, benzotriazol-5-yl, chromen-6- or -7-yl, cyclohexen-1-yl, 4,5-dihydro-1H-indazol-6-yl, 3,4-dihydro-2H-[1,8]napthyridin-6-yl, imidazo[1,5-a]pyridine-6-yl, indan-5-yl, indazol-5- or -6-yl, isochroman-7-yl, 2,3-dihydro-benzo[1,4]dioxin-6-yl, 3,4-dihydro-2H-benzo[b][1,4]dioxepin-7-yl, 2,3-dihydro-5H-benzo[e][1,4]dioxepin-7-yl, 3,4-dihydro-2H-naphthalen-1-on-6- or -7-yl, chroman-6- or -7-yl, 1,3,4,5-tetrahydrobenzo[c]oxepin-8-yl and 4, 5, 6, 7-tetrahydroindazol-6-yl;
wherein A is optionally substituted with one to three groups selected from $C_{1-3}$alkyl, $C_{3-5}$cycloalkyl, —OH, oxo, $C_{1-3}$alkoxy, Cl, F, —CF$_3$, —CN, —C(O)CH$_3$ and —C(O)NH$_2$;
and
$R^2$ is selected from —OH, —CN, —NHC(O)C$_{1-3}$alkyl, —NHC(O)cyclopropyl, —NHSO$_2$C$_{1-3}$alkyl and —NHC(O)CH$_2$C(CH$_3$)$_2$—OH;
or a salt thereof.

6. The compound according to claim 1 selected from the group consisting of

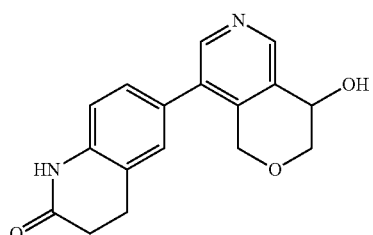

1

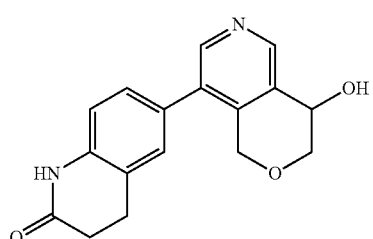

2

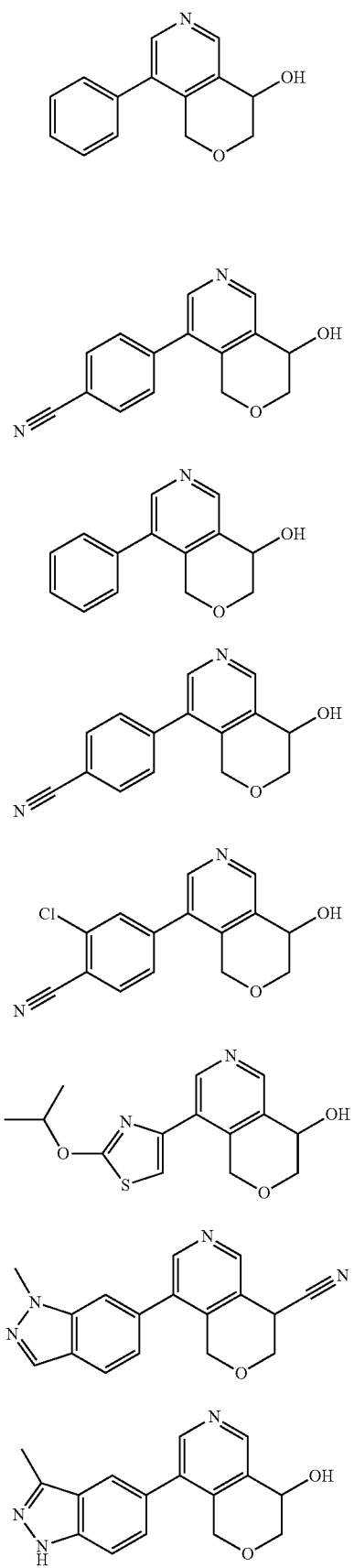
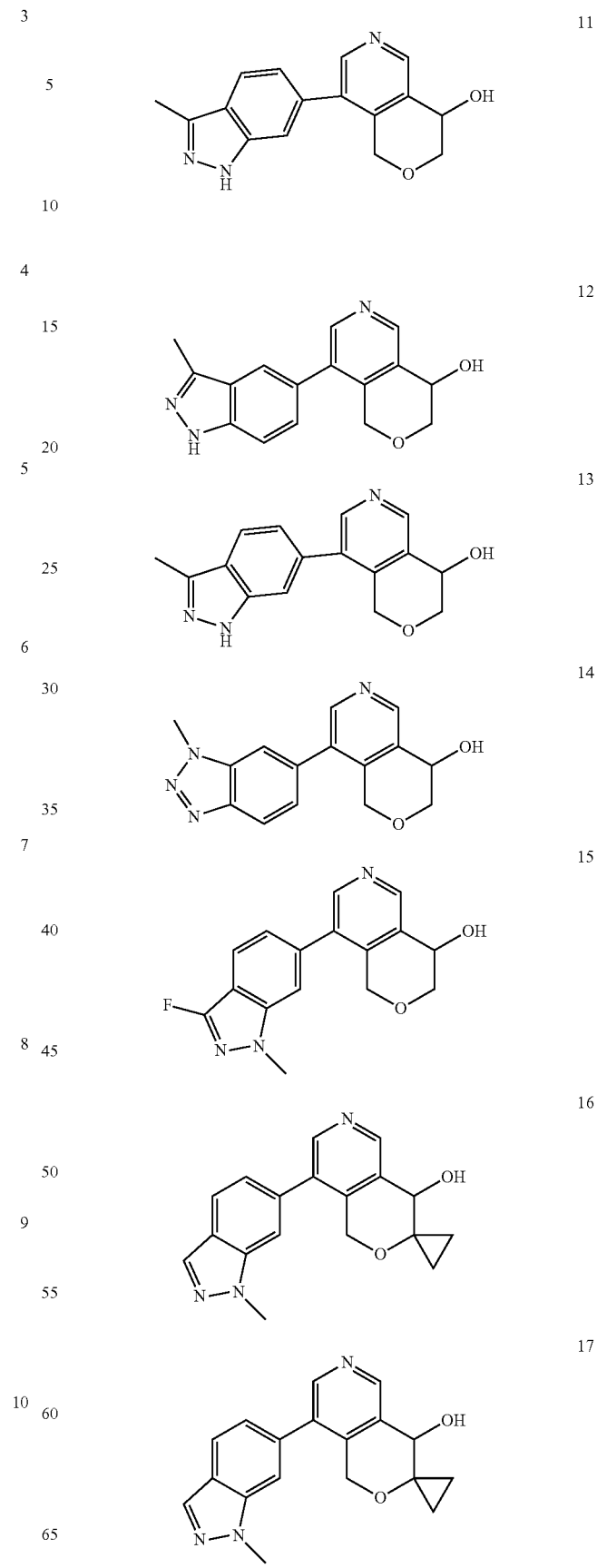

123
-continued

18

19

20

21

22

23

24

25

124
-continued

26

27

28

29

30

31

32

33

34
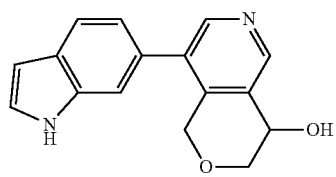
35
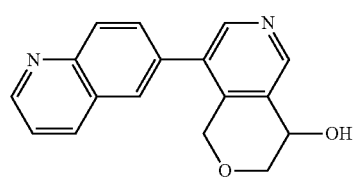
36
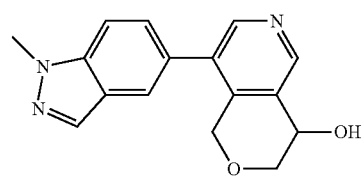
37
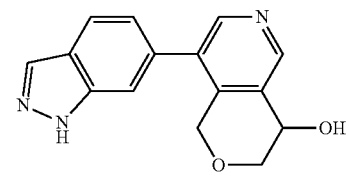
38
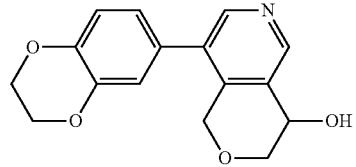
39
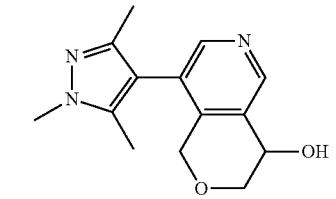
40
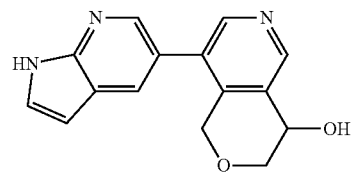
41
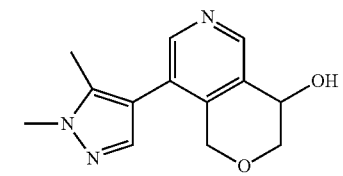
42
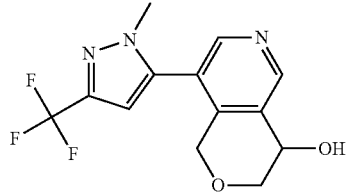
43
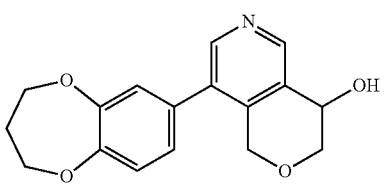
44
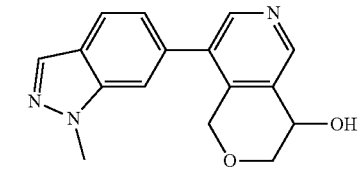
45
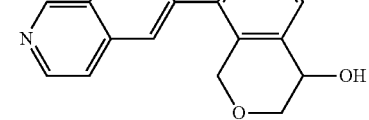
46
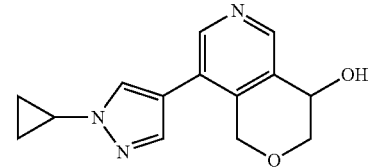
47
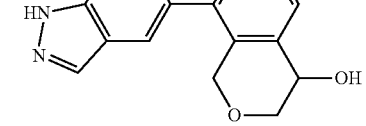
48
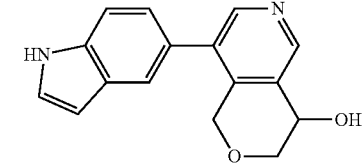
49
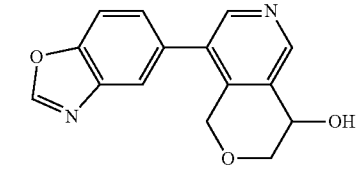

| 127 -continued | | 128 -continued | |
|---|---|---|---|
| 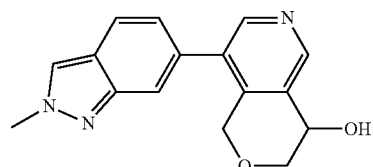 | 50 | 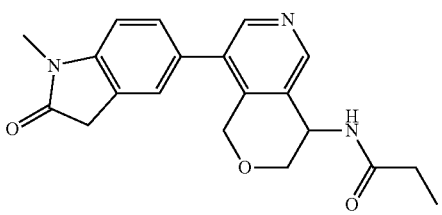 | 58 |
| 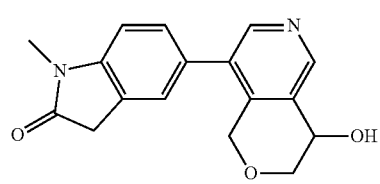 | 51 | 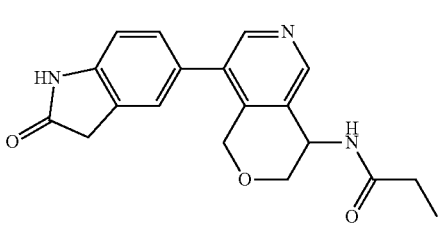 | 59 |
| 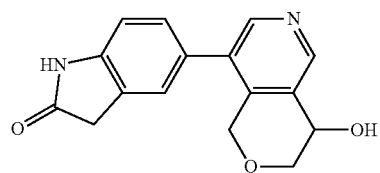 | 52 | 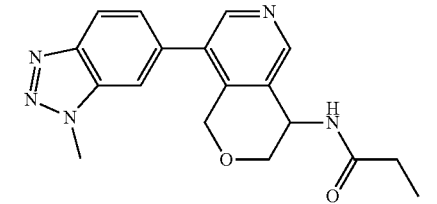 | 60 |
| 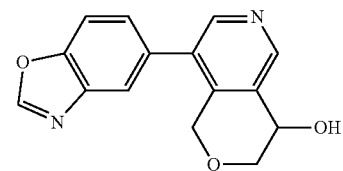 | 53 | 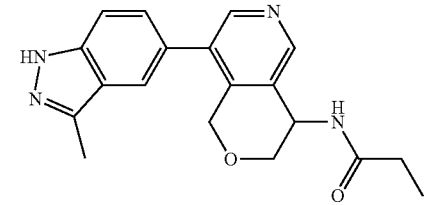 | 61 |
| 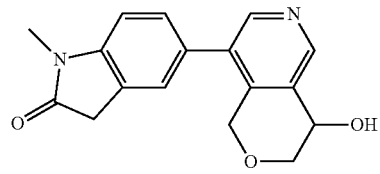 | 54 | 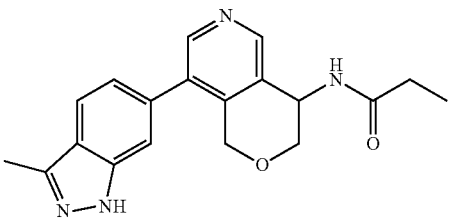 | 62 |
| 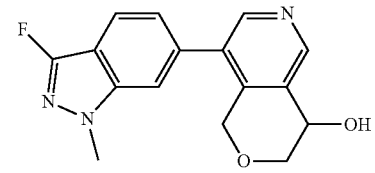 | 55 | 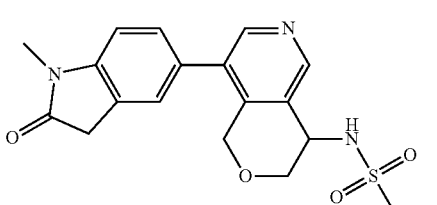 | 63 |
| 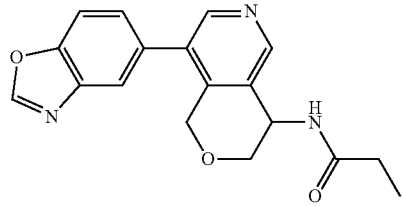 | 56 | 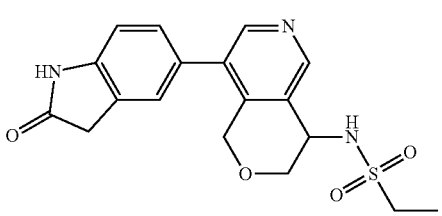 | 64 |
| 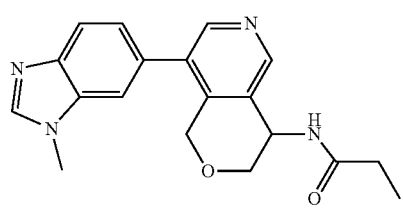 | 57 | | |

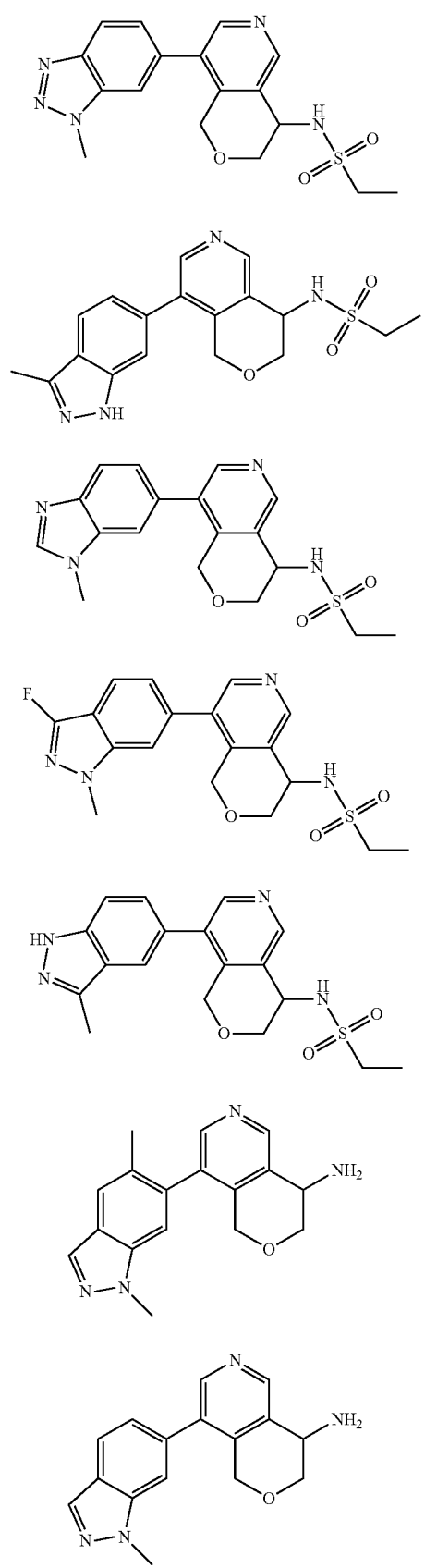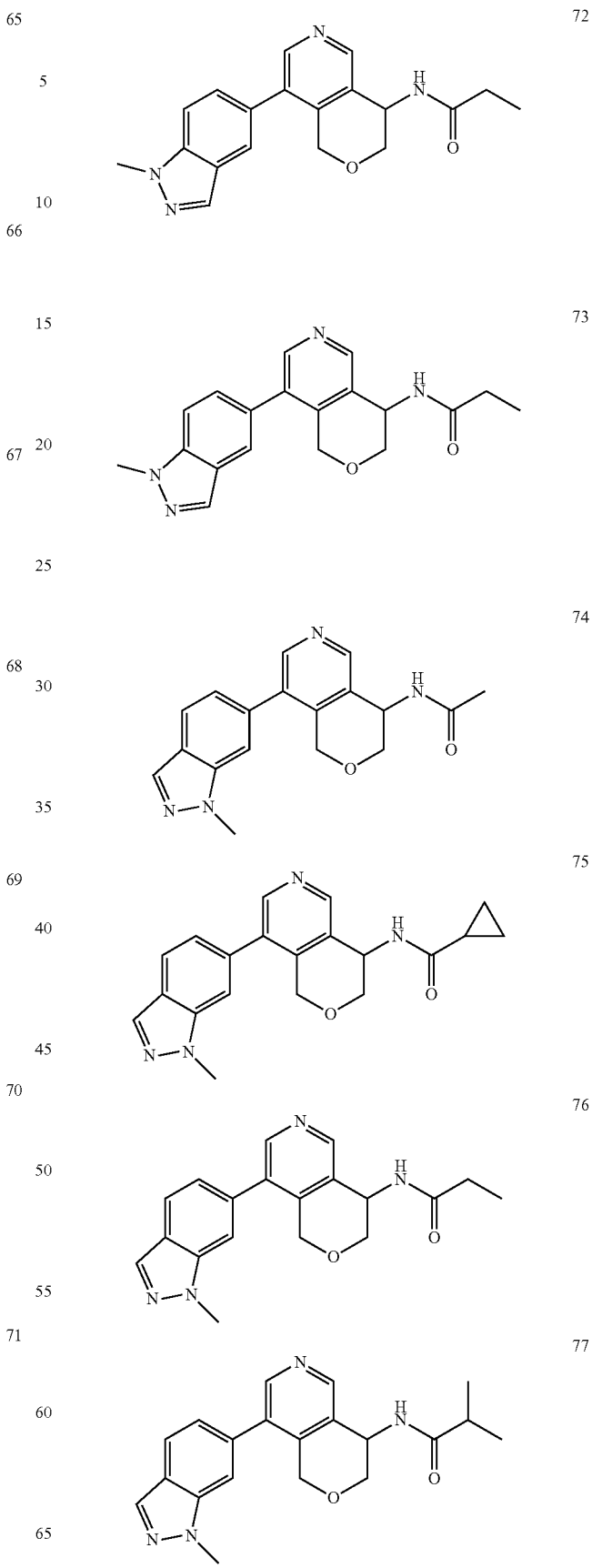

78 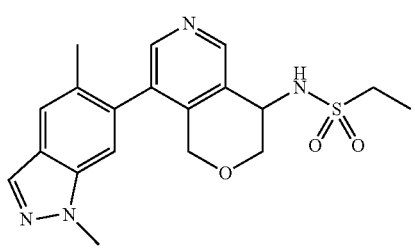
79 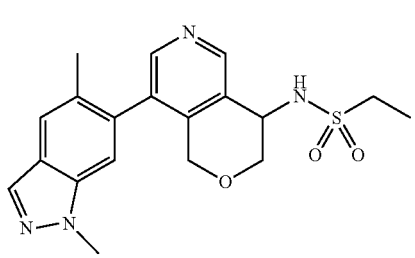
80 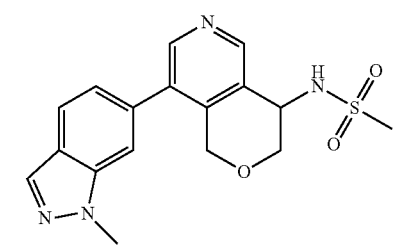
81 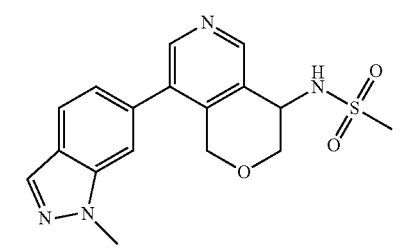
82 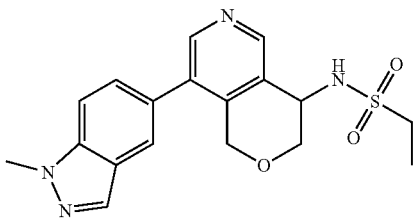
83 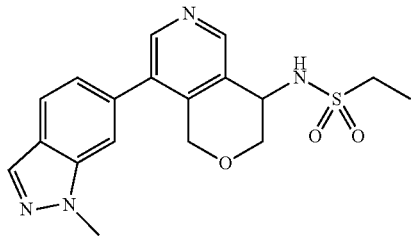
84 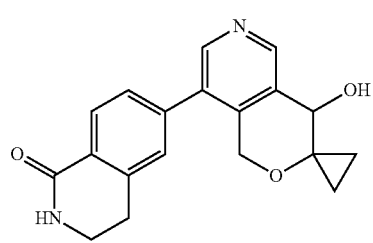
85 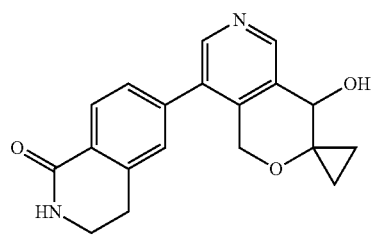
86 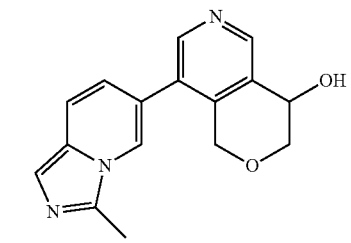
87 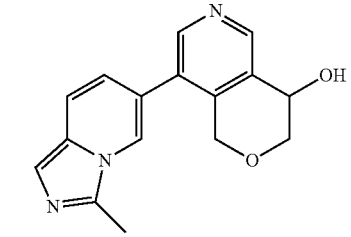
88 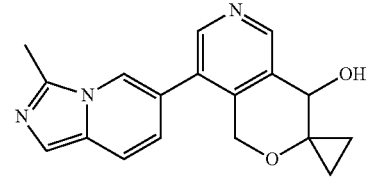
89 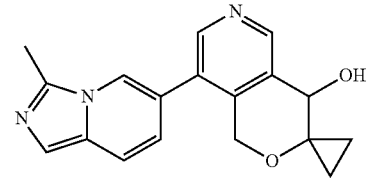
90 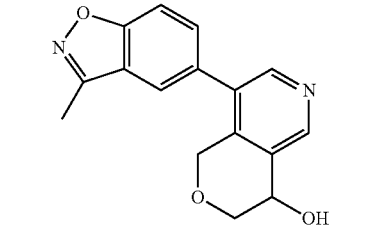

| 133 -continued | | 134 -continued | |
|---|---|---|---|
| 91 | 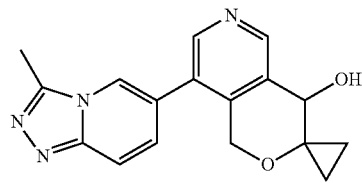 | 98 | 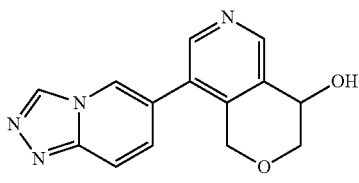 |
| 92 | 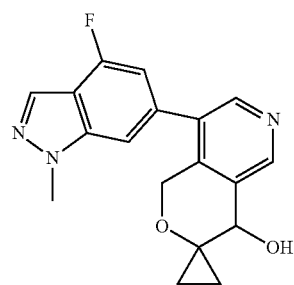 | 99 | 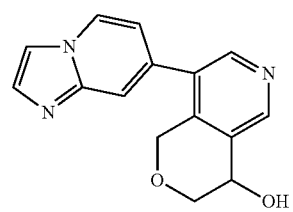 |
| 93 | 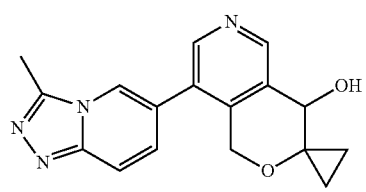 | 100 | 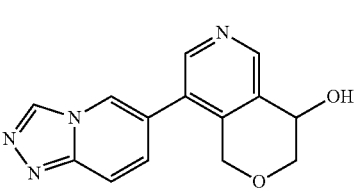 |
| 94 | 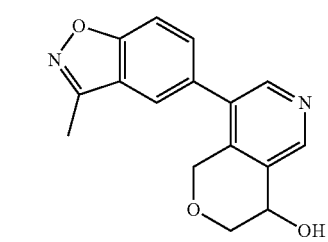 | 101 | 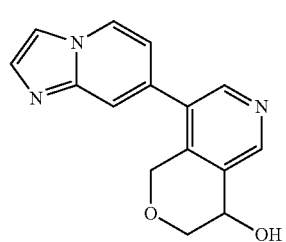 |
| 95 | 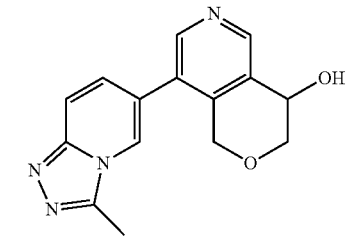 | 102 | 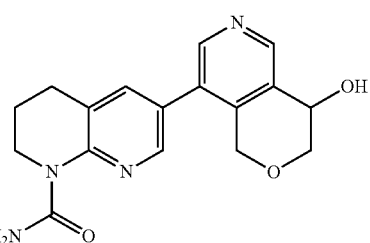 |
| 96 | 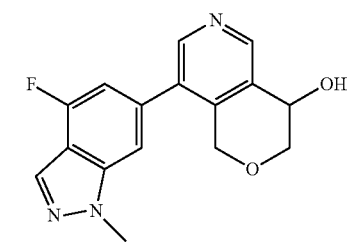 | 103 | 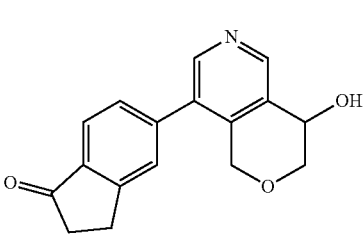 |
| 97 | 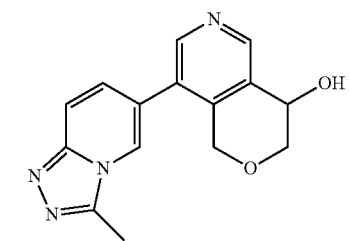 | 104 | 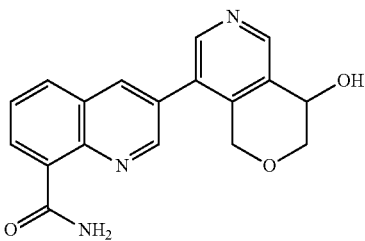 |

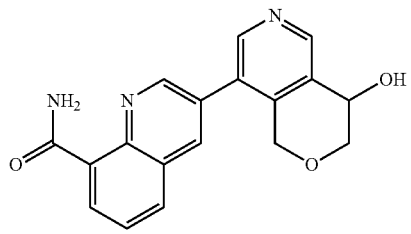
105
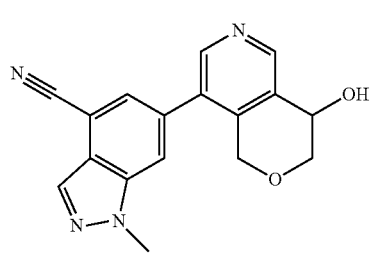
106
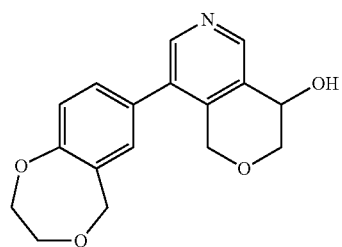
107
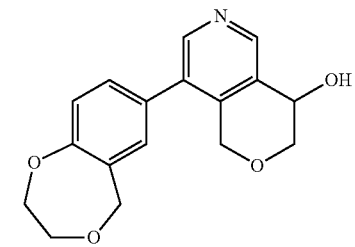
108
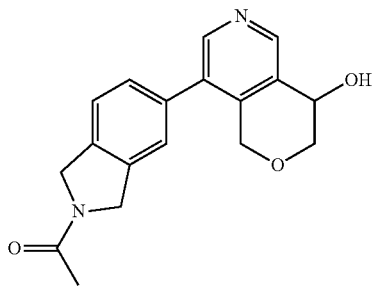
109
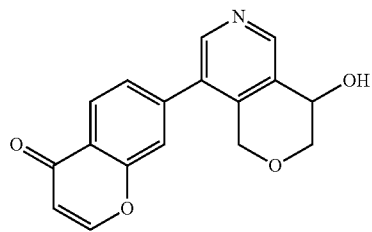
110
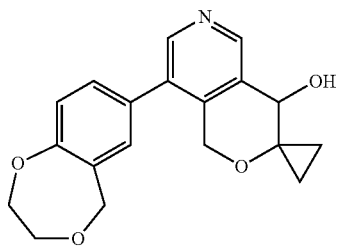
111
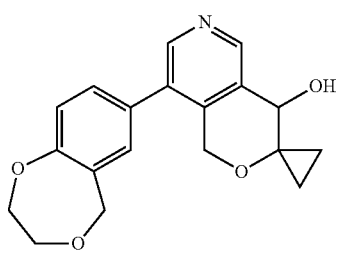
112
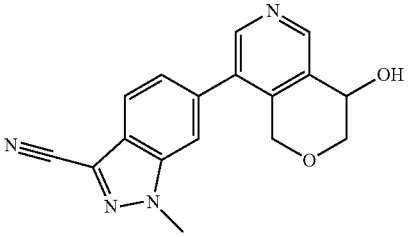
113
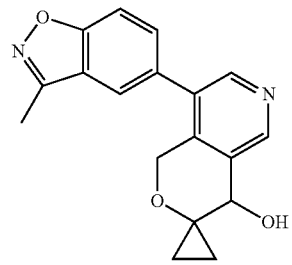
114
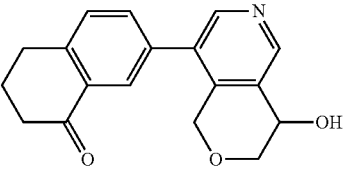
115
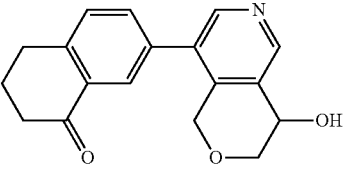
116
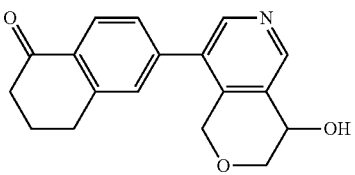
117

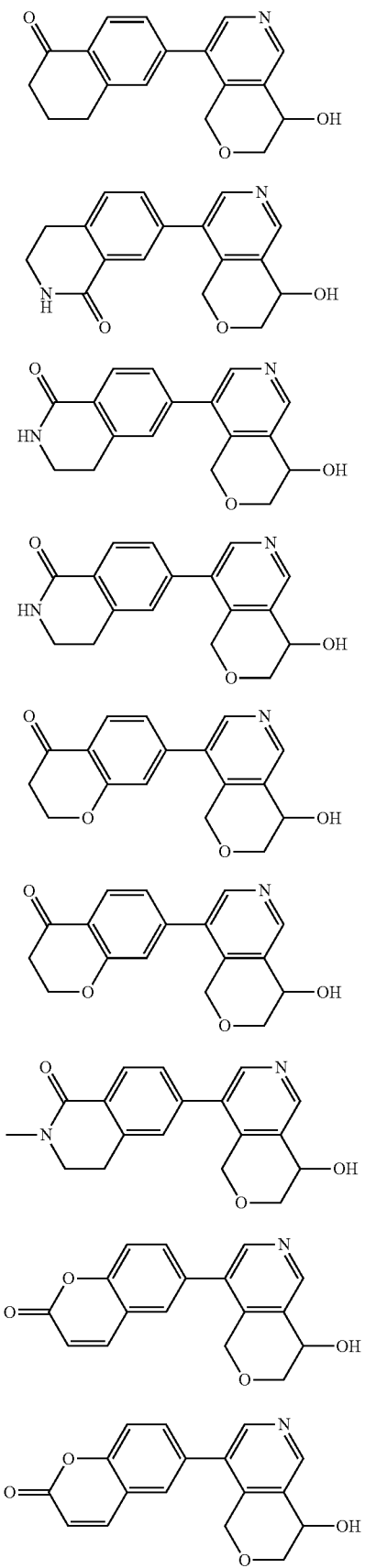
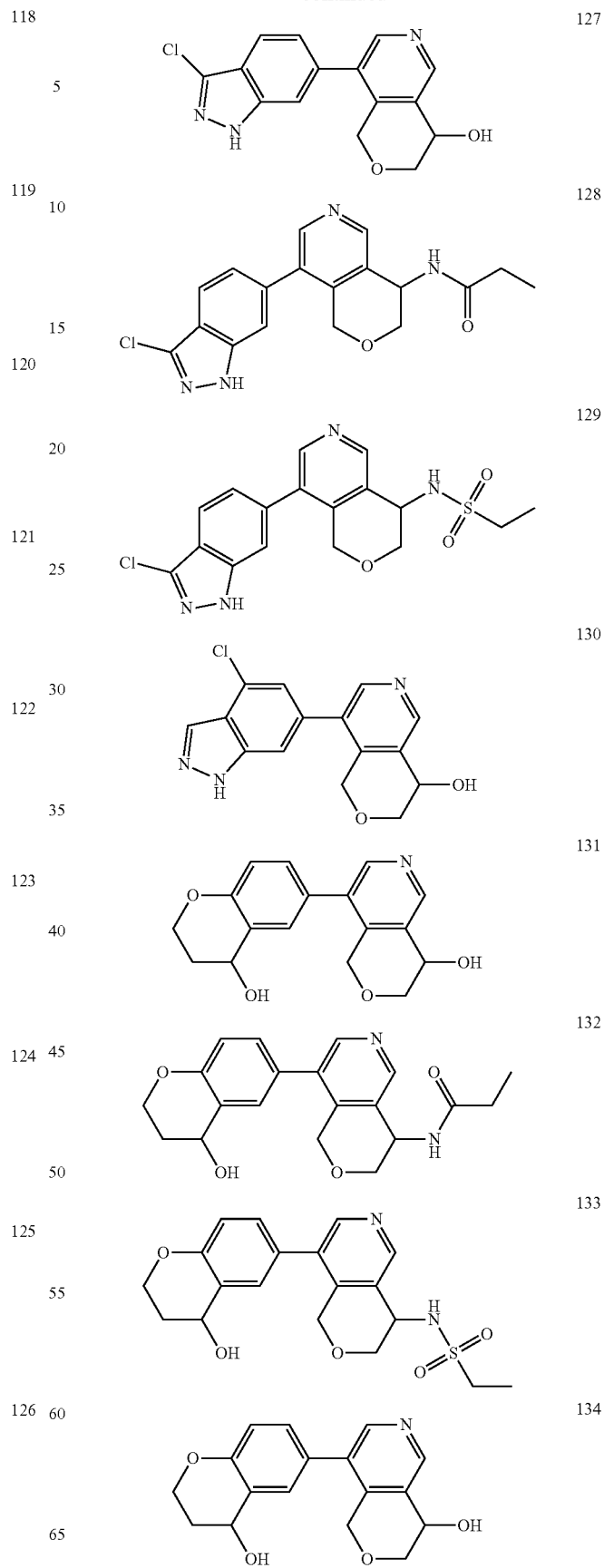

135 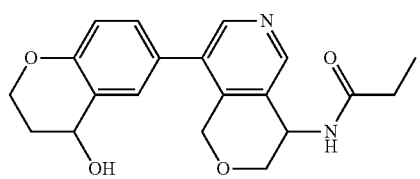
136 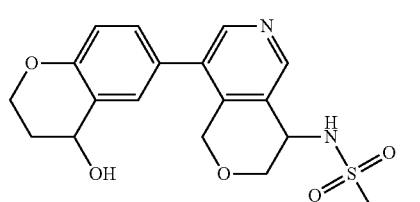
137 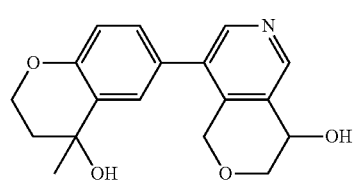
138 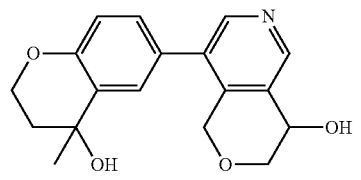
139 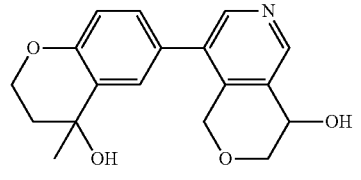
140 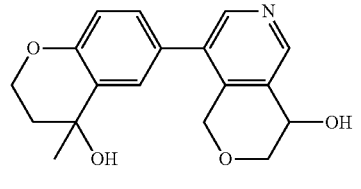
141 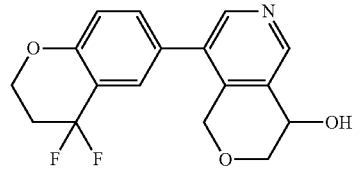
142 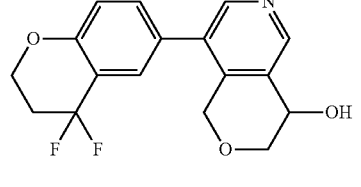
143 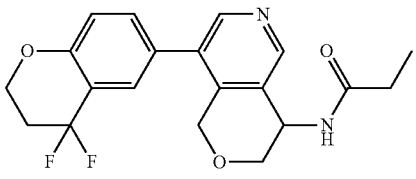
144 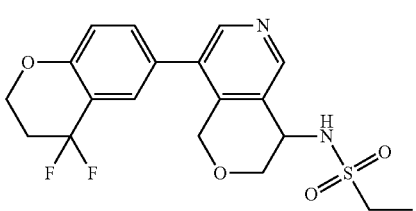
145 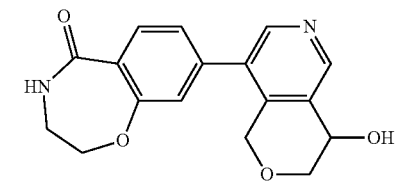
146 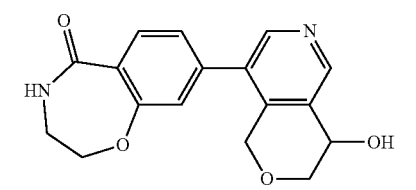
147 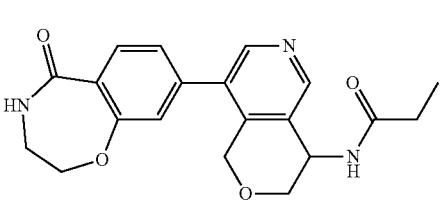
148 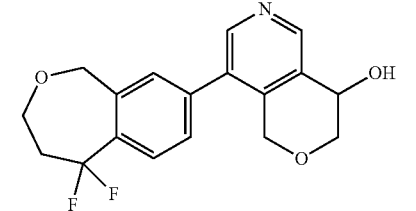
149 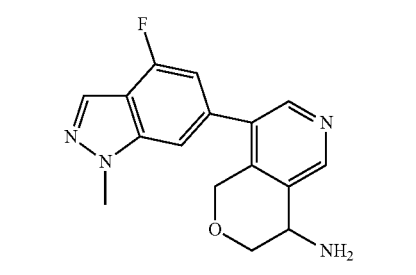

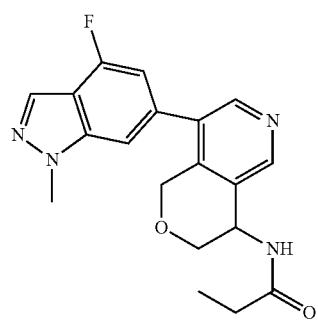
150
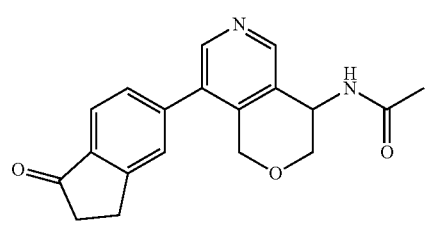
151
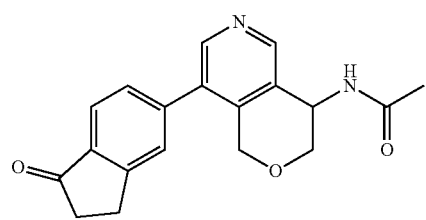
152
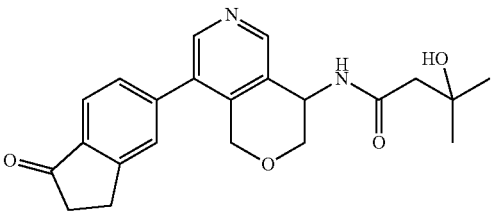
153
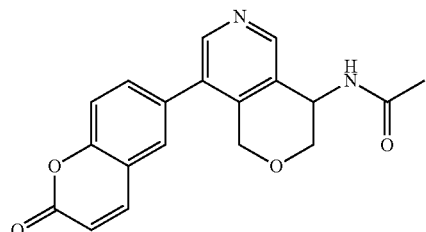
154
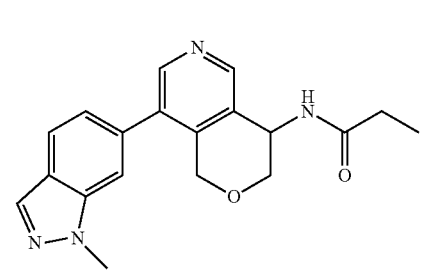
155
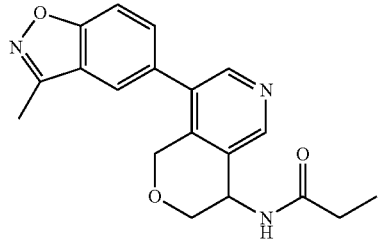
156
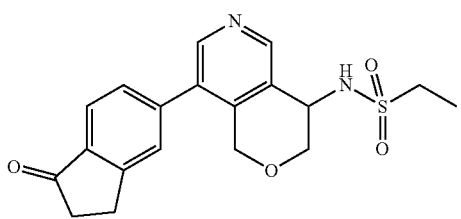
157
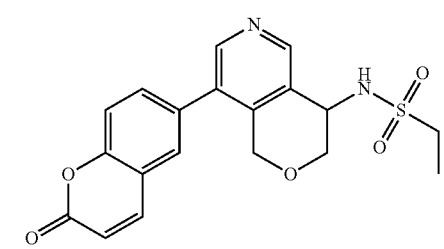
158
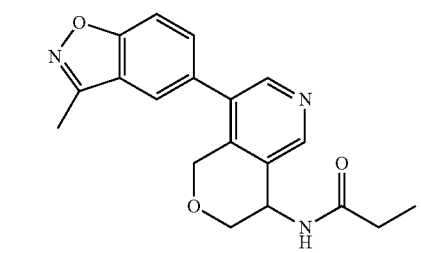
159
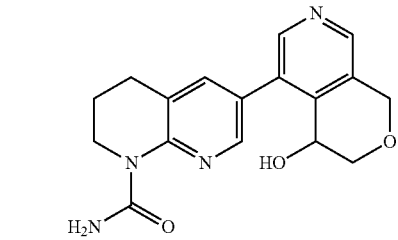
160
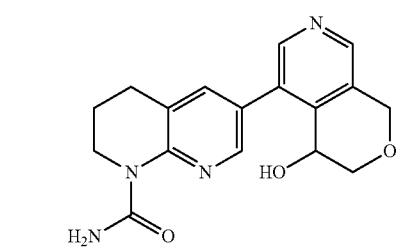
161

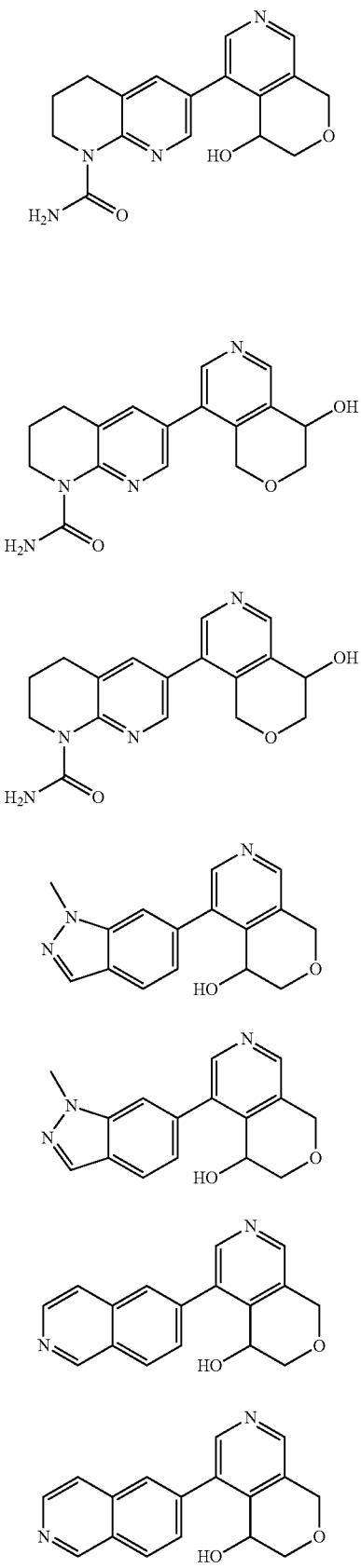
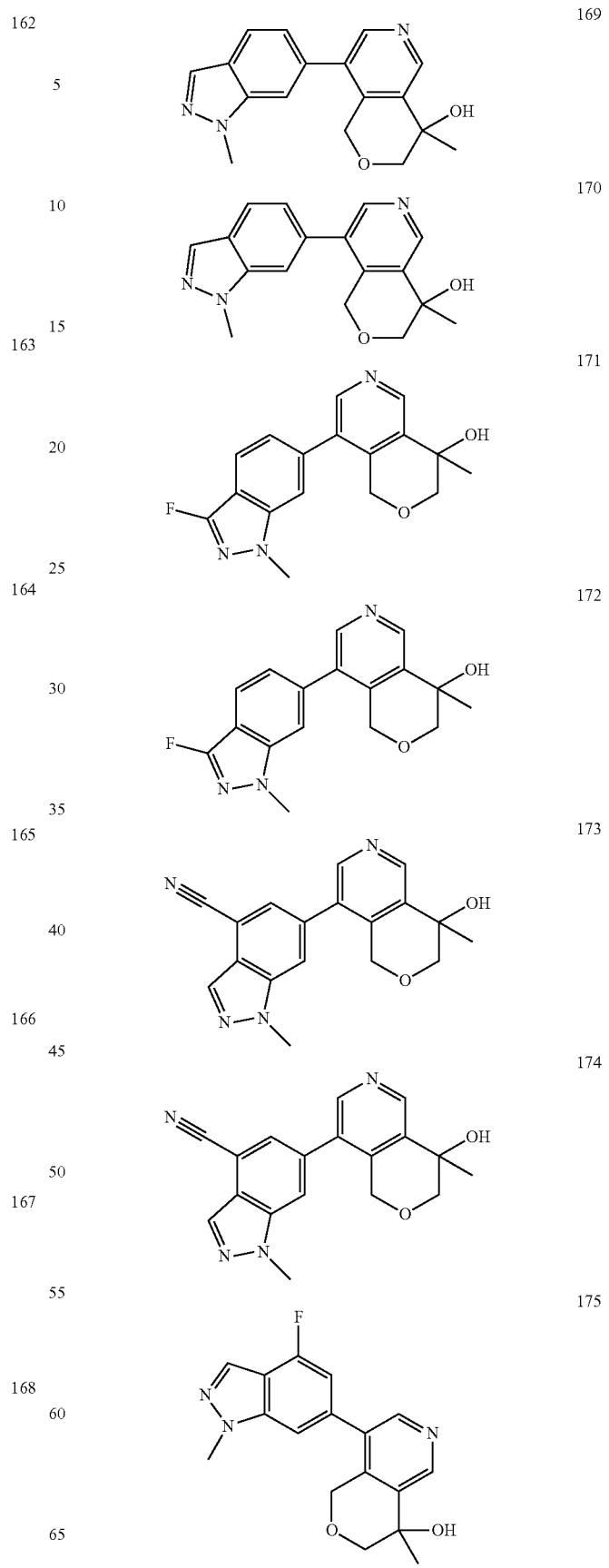

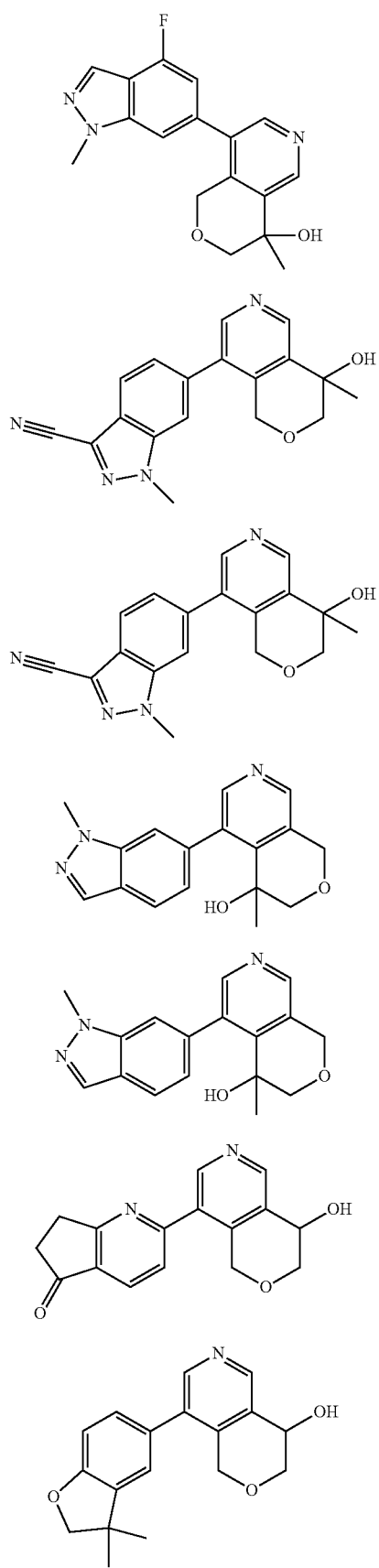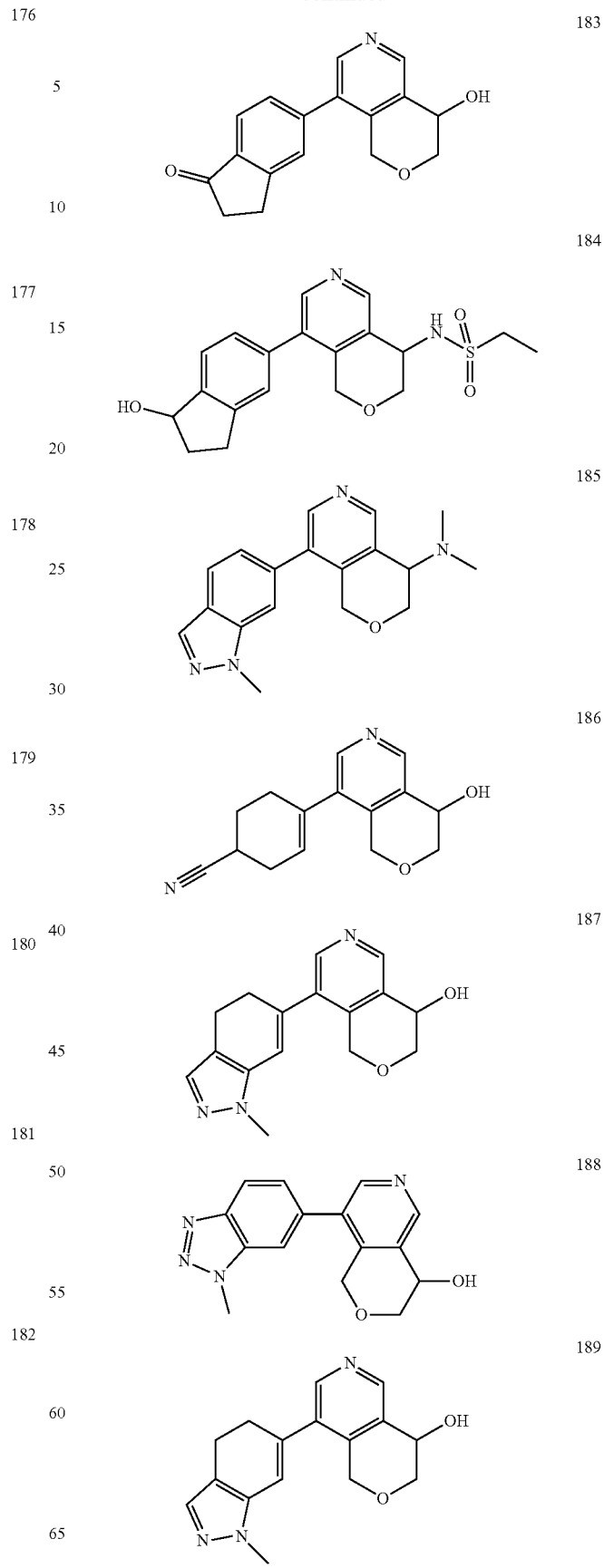

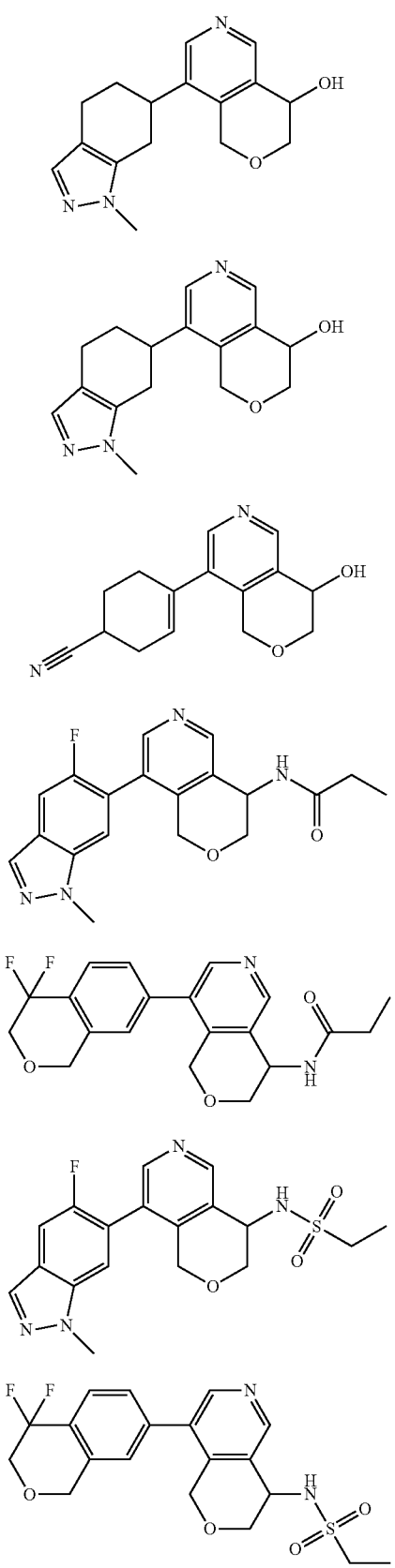
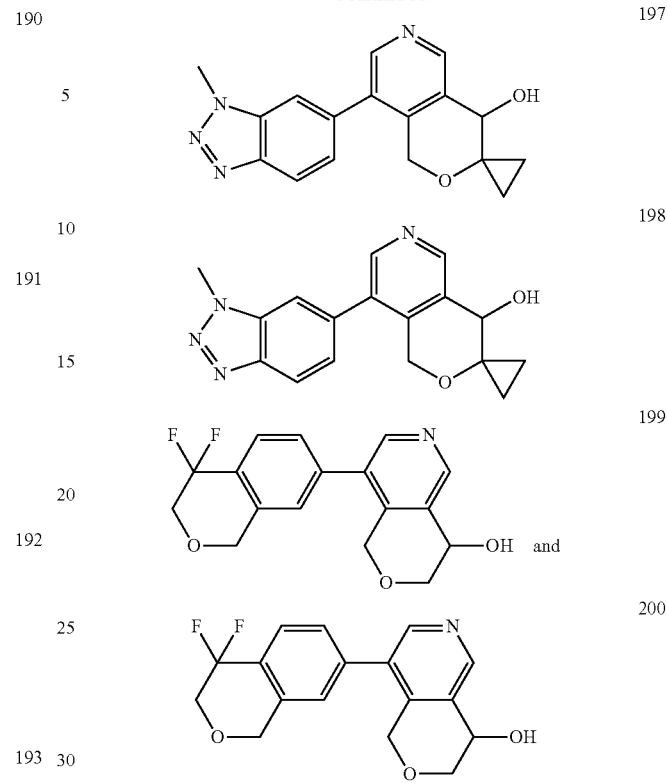

and the pharmaceutically acceptable salts thereof.

7. The compound according to claim 6 selected from the group consisting of compound numbers 9, 12-18, 29, 34, 36-38, 43-45, 47, 48, 55, 60, 61, 65, 68, 69, 71, 73-77, 81, 83, 85, 89, 90, 92, 94, 96, 102-105, 107, 110, 112-114, 116, 118, 121, 123, 125-129, 131-133, 136, 142, 143, 148-150, 152-154, 157, 158, 160-164, 166, 168-172, 175-179, 183 and 185-199 and the pharmaceutically acceptable salts thereof.

8. A pharmaceutical composition comprising a compound according to claim 1 and a pharmaceutically acceptable excipient or carrier.

9. A method of treating a disease or disorder that can be alleviated by inhibition of aldosterone synthase selected from diabetic nephropathy, glomerulosclerosis, glomerulonephritis, IGA nephropathy, nephritic syndrome focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filling abnormalities, arterial stiffness, atherosclerosis and cardiovascular morbidity associated with primary or secondary hyperaldosteronism, adrenal hyperplasia and primary and secondary hyperaldosteronism comprising administering a therapeutically effective amount of a compound according to claim 1, or a pharmaceutically acceptable salt thereof, to patient in need thereof.

10. The method according to claim 9, wherein the disease or disorder is selected from diabetic nephropathy, glomerulosclerosis, glomerulonephritis, IGA nephropathy, nephritic syndrome and focal segmental glomerulosclerosis (FSGS).

11. The method according to claim 9 wherein the disease is diabetic nephropathy.

* * * * *